United States Patent
Brunner-Schwarz et al.

(10) Patent No.: US 9,707,176 B2
(45) Date of Patent: *Jul. 18, 2017

(54) PHARMACEUTICAL COMPOSITION COMPRISING A GLP-1 AGONIST AND METHIONINE

(75) Inventors: Anette Brunner-Schwarz, Frankfurt (DE); Werner Mueller, Frankfurt am Main (DE); Verena Siefke-Henzler, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/509,507

(22) PCT Filed: Nov. 11, 2010

(86) PCT No.: PCT/EP2010/067249
§ 371 (c)(1),
(2), (4) Date: Jul. 30, 2012

(87) PCT Pub. No.: WO2011/058082
PCT Pub. Date: May 19, 2011

(65) Prior Publication Data
US 2012/0283179 A1    Nov. 8, 2012

(30) Foreign Application Priority Data

Nov. 13, 2009  (DE) .................. 10 2009 052 832
Mar. 18, 2010  (DE) .................. 10 2010 011 919

(51) Int. Cl.
| | |
|---|---|
| A61K 38/26 | (2006.01) |
| A61P 3/10 | (2006.01) |
| A61K 9/08 | (2006.01) |
| A61K 9/00 | (2006.01) |
| A61K 38/22 | (2006.01) |
| A61K 47/18 | (2017.01) |
| A61K 47/10 | (2017.01) |

(52) U.S. Cl.
CPC .............. *A61K 9/08* (2013.01); *A61K 9/0019* (2013.01); *A61K 38/2278* (2013.01); *A61K 38/26* (2013.01); *A61K 47/10* (2013.01); *A61K 47/183* (2013.01)

(58) Field of Classification Search
CPC ...................................................... A61K 38/26
See application file for complete search history.

(56) References Cited

U.S. PATENT DOCUMENTS

| | | | |
|---|---|---|---|
| 3,758,683 A | 9/1973 | Jackson | |
| 3,868,358 A | 2/1975 | Jackson | |
| 3,984,696 A | 10/1976 | Collica et al. | |
| 4,153,689 A | 5/1979 | Hirai et al. | |
| 4,258,134 A | 3/1981 | Yoshida et al. | |
| 4,367,737 A | 1/1983 | Kozam et al. | |
| 4,608,364 A | 8/1986 | Grau | |
| 4,614,730 A | 9/1986 | Hansen et al. | |
| 4,644,057 A | 2/1987 | Bicker et al. | |
| 4,689,042 A | 8/1987 | Sarnoff et al. | |
| 4,701,440 A | 10/1987 | Grau | |
| 4,731,405 A | 3/1988 | Kirsch et al. | |
| 4,783,441 A | 11/1988 | Thurow | |
| 4,839,341 A | 6/1989 | Massey et al. | |
| 4,863,902 A | 9/1989 | Amagase et al. | |
| 4,885,164 A | 12/1989 | Thurow | |
| 4,923,162 A | 5/1990 | Fleming et al. | |
| 4,959,351 A | 9/1990 | Grau | |
| 4,960,702 A | 10/1990 | Rice et al. | |
| 4,994,439 A | 2/1991 | Longenecker et al. | |
| 5,006,718 A | 4/1991 | Lenhart | |
| 5,008,241 A | 4/1991 | Markussen et al. | |
| 5,034,415 A | 7/1991 | Rubin | |
| 5,070,186 A | 12/1991 | Joergensen | |
| 5,101,013 A | 3/1992 | Dorschug et al. | |
| 5,177,058 A | 1/1993 | Dorschug | |
| 5,187,177 A | 2/1993 | Garzaran | |
| 5,227,293 A | 7/1993 | Stengelin et al. | |
| 5,253,785 A | 10/1993 | Haber et al. | |
| 5,272,135 A * | 12/1993 | Takruri ................ | A61K 9/0014 514/15.2 |
| 5,358,708 A | 10/1994 | Patel | |
| 5,358,857 A | 10/1994 | Stengelin et al. | |
| 5,370,629 A | 12/1994 | Michel et al. | |
| 5,397,771 A | 3/1995 | Bechgaard et al. | |

(Continued)

FOREIGN PATENT DOCUMENTS

| | | |
|---|---|---|
| AU | 593274 B2 | 2/1990 |
| AU | 612324 B2 | 7/1991 |

(Continued)

OTHER PUBLICATIONS

International Preliminary Report on Patentability and Written Opinion issued in PCT/EP2010/067249 dated Jun. 12, 2012.
International Search Report dated Feb. 4, 2011 issued in PCT/EP2010/067249.
English Translation of Office Action dated Aug. 26, 2013 issued in parallel Korean Patent Application No. 10-2012-7014976.
Arnolds, S. et al., "Insulin Glargine (GLAR) plus Metformin (MET): An Efficacious and Safe Regimen That Can Be Combined with Exenatide (EXE) or Sitagliptin (SITA)," Diabetes, American Diabetes Association (2009), vol. 58.

(Continued)

*Primary Examiner* — Gyan Chandra
(74) *Attorney, Agent, or Firm* — McDonnell Boehnen Hulbert & Berghoff LLP

(57) ABSTRACT

A liquid composition comprising a GLP-1 agonist or/and a pharmacologically tolerable salt thereof and, optionally, at least one pharmaceutically acceptable excipient, wherein the composition comprises methionine, as add-on therapy with metformin and/or with long-acting insulin/insulin derivates where appropriate.

30 Claims, 6 Drawing Sheets

(56) References Cited

U.S. PATENT DOCUMENTS

| | | |
|---|---|---|
| 5,407,609 A | 4/1995 | Tice et al. |
| 5,424,286 A | 6/1995 | Eng |
| 5,428,006 A | 6/1995 | Bechgaard et al. |
| 5,473,049 A | 12/1995 | Obermeier et al. |
| 5,474,978 A | 12/1995 | Bakaysa et al. |
| 5,478,323 A | 12/1995 | Westwood et al. |
| 5,496,924 A | 3/1996 | Habermann et al. |
| 5,506,203 A | 4/1996 | Backstrom et al. |
| 5,509,905 A | 4/1996 | Michel |
| 5,514,646 A | 5/1996 | Chance et al. |
| 5,524,286 A | 6/1996 | Chiesa et al. |
| 5,534,488 A | 7/1996 | Hoffmann |
| 5,545,618 A | 8/1996 | Buckley et al. |
| 5,547,929 A | 8/1996 | Anderson, Jr. et al. |
| 5,559,094 A | 9/1996 | Brems et al. |
| 5,595,756 A | 1/1997 | Bally et al. |
| 5,597,796 A | 1/1997 | Brange |
| 5,614,219 A | 3/1997 | Wunderlich et al. |
| 5,614,492 A | 3/1997 | Habener |
| 5,631,224 A | 5/1997 | Efendic et al. |
| 5,654,008 A | 8/1997 | Herbert et al. |
| 5,656,722 A | 8/1997 | Dorschug |
| 5,663,291 A | 9/1997 | Obermeier et al. |
| 5,670,360 A | 9/1997 | Thorens |
| 5,693,608 A | 12/1997 | Bechgaard et al. |
| 5,700,662 A | 12/1997 | Chance et al. |
| 5,707,641 A | 1/1998 | Gertner et al. |
| 5,783,556 A | 7/1998 | Clark et al. |
| 5,824,638 A | 10/1998 | Burnside et al. |
| 5,846,747 A | 12/1998 | Thorens et al. |
| 5,846,937 A | 12/1998 | Drucker |
| 5,948,751 A | 9/1999 | Kimer et al. |
| 5,952,297 A | 9/1999 | De Felippis et al. |
| 5,981,964 A | 11/1999 | McAuley et al. |
| 5,985,309 A | 11/1999 | Edwards et al. |
| 5,986,048 A | 11/1999 | Rubroder et al. |
| 6,006,753 A | 12/1999 | Efendic |
| 6,034,054 A | 3/2000 | DeFelippis et al. |
| 6,043,214 A | 3/2000 | Jensen et al. |
| 6,051,551 A | 4/2000 | Hughes et al. |
| 6,051,689 A | 4/2000 | Thorens |
| 6,100,376 A | 8/2000 | Dorschug |
| 6,110,703 A | 8/2000 | Egel-Mitani et al. |
| 6,174,856 B1 | 1/2001 | Langballe et al. |
| 6,191,102 B1 | 2/2001 | DiMarchi et al. |
| 6,197,926 B1 | 3/2001 | Gaur et al. |
| 6,211,144 B1 | 4/2001 | Havelund |
| 6,227,819 B1 | 5/2001 | Gettel et al. |
| 6,248,363 B1 | 6/2001 | Patel et al. |
| 6,267,981 B1 | 7/2001 | Okamoto et al. |
| 6,268,335 B1 | 7/2001 | Brader |
| 6,268,343 B1 | 7/2001 | Knudsen et al. |
| 6,271,241 B1 | 8/2001 | DeSimone et al. |
| 6,284,725 B1 | 9/2001 | Coolidge et al. |
| 6,309,663 B1 | 10/2001 | Patel et al. |
| 6,310,038 B1 | 10/2001 | Havelund |
| 6,329,336 B1 | 12/2001 | Bridon et al. |
| 6,335,316 B1 | 1/2002 | Hughes et al. |
| 6,344,180 B1 | 2/2002 | Holst et al. |
| 6,358,924 B1 | 3/2002 | Hoffmann |
| 6,384,016 B1 | 5/2002 | Kaarsholm |
| 6,388,053 B1 | 5/2002 | Galloway et al. |
| 6,395,767 B2 * | 5/2002 | Robl et al. ............... 514/412 |
| 6,410,508 B1 | 6/2002 | Isales et al. |
| 6,417,164 B1 | 7/2002 | Kolterman et al. |
| 6,444,641 B1 | 9/2002 | Flora |
| 6,468,959 B1 | 10/2002 | Wunderlich et al. |
| 6,489,292 B1 | 12/2002 | Havelund et al. |
| 6,528,486 B1 | 3/2003 | Larsen et al. |
| 6,734,162 B2 | 5/2004 | Van Antwerp et al. |
| 6,767,887 B1 | 7/2004 | Hoffmann et al. |
| 6,818,738 B2 | 11/2004 | Havelund |
| 6,852,694 B2 | 2/2005 | Van Antwerp et al. |
| 6,875,589 B1 | 4/2005 | Doerschug et al. |
| 6,908,610 B1 | 6/2005 | Sato |
| 6,908,897 B2 | 6/2005 | Brandenburg et al. |
| 6,960,561 B2 | 11/2005 | Boderke |
| 6,969,702 B2 | 11/2005 | Bertilsson et al. |
| 7,022,674 B2 | 4/2006 | DeFelippis et al. |
| 7,115,563 B2 | 10/2006 | Younis et al. |
| 7,119,086 B2 | 10/2006 | Di et al. |
| 7,192,919 B2 | 3/2007 | Tzannis et al. |
| 7,205,276 B2 | 4/2007 | Boderke |
| 7,205,277 B2 | 4/2007 | Boderke |
| 7,238,663 B2 | 7/2007 | DeFelippis et al. |
| 7,405,196 B2 | 7/2008 | Rosskamp et al. |
| 7,476,652 B2 | 1/2009 | Brunner-Schwarz et al. |
| 7,544,656 B2 | 6/2009 | Sabetsky |
| 7,544,657 B2 | 6/2009 | Ebbehoj et al. |
| 7,576,050 B2 | 8/2009 | Greig et al. |
| 7,713,930 B2 | 5/2010 | Brunner-Schwarz et al. |
| 7,803,763 B2 | 9/2010 | Thurow et al. |
| 7,807,242 B2 | 10/2010 | Soerensen et al. |
| 7,918,833 B2 | 4/2011 | Veasey et al. |
| 7,939,293 B2 | 5/2011 | Habermann et al. |
| 7,977,310 B2 | 7/2011 | Rosskamp et al. |
| 8,048,854 B2 | 11/2011 | Habermann et al. |
| 8,084,420 B2 | 12/2011 | Steiner et al. |
| 8,092,421 B2 | 1/2012 | Seiferlein et al. |
| 8,092,422 B2 | 1/2012 | Seiferlein et al. |
| 8,178,495 B2 | 5/2012 | Chilkoti |
| 8,574,214 B2 | 11/2013 | Kuhn et al. |
| 8,633,156 B2 | 1/2014 | Habermann et al. |
| 8,735,349 B2 | 5/2014 | Silvestre et al. |
| 2001/0012829 A1 | 8/2001 | Anderson et al. |
| 2001/0033868 A1 | 10/2001 | Rossling et al. |
| 2001/0039260 A1 | 11/2001 | Havelund |
| 2001/0047084 A1 | 11/2001 | Knudsen et al. |
| 2002/0107265 A1 | 8/2002 | Chen et al. |
| 2002/0132760 A1 | 9/2002 | Van Antwerp et al. |
| 2002/0177151 A1 | 11/2002 | Gimeno |
| 2002/0198140 A1 | 12/2002 | Havelund |
| 2003/0004096 A1 | 1/2003 | Boderke |
| 2003/0026872 A1 | 2/2003 | Dake et al. |
| 2003/0104983 A1 | 6/2003 | DeFelippis et al. |
| 2003/0170691 A1 | 9/2003 | Gimeno et al. |
| 2004/0037893 A1 | 2/2004 | Hansen et al. |
| 2004/0048783 A1 | 3/2004 | Brunner-Schwarz et al. |
| 2004/0092590 A1 | 5/2004 | Arterburn et al. |
| 2004/0097410 A1 | 5/2004 | Zheng et al. |
| 2004/0106547 A1 | 6/2004 | Larsen et al. |
| 2004/0186046 A1 | 9/2004 | Burgess et al. |
| 2004/0229774 A1 | 11/2004 | Rosskamp et al. |
| 2004/0235710 A1 | 11/2004 | DeFelippis et al. |
| 2004/0242853 A1 | 12/2004 | Greig et al. |
| 2005/0014679 A1 | 1/2005 | Beals et al. |
| 2005/0079996 A1 | 4/2005 | Horiguchi et al. |
| 2005/0106147 A1 | 5/2005 | Jordan et al. |
| 2005/0171009 A1 | 8/2005 | Brunner-Schwarz et al. |
| 2005/0209142 A1 | 9/2005 | Bertilsson et al. |
| 2006/0004049 A1 | 1/2006 | Yao et al. |
| 2006/0014678 A1 | 1/2006 | Cowley et al. |
| 2006/0019347 A1 | 1/2006 | Cho et al. |
| 2006/0057137 A1 | 3/2006 | Steiness |
| 2006/0073213 A1 | 4/2006 | Hotamisligil et al. |
| 2006/0093576 A1 | 5/2006 | Chen et al. |
| 2006/0194719 A1 | 8/2006 | Ebbehoj et al. |
| 2006/0239933 A1 | 10/2006 | Nilsson et al. |
| 2006/0287221 A1 | 12/2006 | Knudsen et al. |
| 2007/0027063 A1 | 2/2007 | Boss et al. |
| 2007/0111940 A1 | 5/2007 | Larsen et al. |
| 2007/0128193 A1 | 6/2007 | O'Neil et al. |
| 2007/0135338 A1 | 6/2007 | O'Neil et al. |
| 2007/0155653 A1 | 7/2007 | Boderke |
| 2007/0191271 A1 * | 8/2007 | Mayhew et al. ............... 514/12 |
| 2007/0237827 A1 | 10/2007 | Sung et al. |
| 2008/0064856 A1 | 3/2008 | Warne et al. |
| 2008/0146490 A1 | 6/2008 | Joabsson et al. |
| 2008/0234200 A1 | 9/2008 | Quay et al. |
| 2008/0248999 A1 | 10/2008 | Steiner |
| 2008/0260840 A1 | 10/2008 | Alessi et al. |
| 2008/0267907 A1 * | 10/2008 | Poulsen ............... 424/85.2 |
| 2009/0082255 A1 | 3/2009 | Brunner-Schwarz et al. |
| 2009/0088369 A1 | 4/2009 | Steiness |

(56) References Cited

U.S. PATENT DOCUMENTS

| | | |
|---|---|---|
| 2009/0099064 A1 | 4/2009 | Lougheed |
| 2009/0142338 A1 | 6/2009 | Levetan |
| 2009/0175840 A1 | 7/2009 | Kashyap et al. |
| 2009/0176692 A1 | 7/2009 | Habermann et al. |
| 2009/0180953 A1 | 7/2009 | Gotthardt et al. |
| 2009/0186819 A1 | 7/2009 | Carrier et al. |
| 2009/0208565 A1 | 8/2009 | Ebbehoj et al. |
| 2009/0214468 A1 | 8/2009 | Lin et al. |
| 2009/0214657 A1 | 8/2009 | Qazi et al. |
| 2009/0304665 A1 | 12/2009 | Frost et al. |
| 2009/0312236 A1 | 12/2009 | Beals et al. |
| 2009/0324701 A1 | 12/2009 | Williams |
| 2010/0029558 A1 | 2/2010 | Bristow |
| 2010/0055049 A1 | 3/2010 | Kuo et al. |
| 2010/0057194 A1 | 3/2010 | Ryan |
| 2010/0069292 A1 | 3/2010 | Pohl et al. |
| 2010/0069293 A1 | 3/2010 | Bolotin et al. |
| 2010/0227816 A1 | 9/2010 | Flatt et al. |
| 2010/0279931 A1 | 11/2010 | Garibay et al. |
| 2010/0311112 A1 | 12/2010 | Rissom et al. |
| 2011/0020294 A1 | 1/2011 | Hammerman |
| 2011/0021423 A1 | 1/2011 | Olsen et al. |
| 2011/0077197 A1 | 3/2011 | Habermann et al. |
| 2011/0118178 A1 | 5/2011 | Silvestre et al. |
| 2011/0118180 A1 | 5/2011 | Silvestre et al. |
| 2011/0144008 A1 | 6/2011 | Larsen et al. |
| 2011/0152185 A1 | 6/2011 | Plum et al. |
| 2011/0173722 A1 | 7/2011 | Habermann et al. |
| 2011/0230402 A1 | 9/2011 | Johansen et al. |
| 2011/0236925 A1 | 9/2011 | Hazra et al. |
| 2011/0245165 A1 | 10/2011 | Larsen et al. |
| 2011/0281790 A1 | 11/2011 | Pohl et al. |
| 2011/0301081 A1 | 12/2011 | Becker et al. |
| 2012/0021978 A1 | 1/2012 | Werner et al. |
| 2012/0121611 A1 | 5/2012 | Lodie et al. |
| 2012/0122774 A1 | 5/2012 | Becker et al. |
| 2012/0183616 A1 | 7/2012 | Sprogoe et al. |
| 2012/0232002 A1 | 9/2012 | Schoettle et al. |
| 2012/0241356 A1 | 9/2012 | Pfenninger et al. |
| 2012/0252724 A1 | 10/2012 | Schoettle et al. |
| 2012/0277147 A1 | 11/2012 | Boka et al. |
| 2012/0283179 A1 | 11/2012 | Brunner-Schwarz et al. |
| 2012/0295846 A1 | 11/2012 | Hagendorf et al. |
| 2012/0316108 A1 | 12/2012 | Chen et al. |
| 2013/0005649 A1 | 1/2013 | Niemoeller et al. |
| 2013/0012433 A1 | 1/2013 | Rosskamp et al. |
| 2013/0023467 A1 | 1/2013 | Silvestre et al. |
| 2013/0040878 A1 | 2/2013 | Silvestre et al. |
| 2013/0065828 A1 | 3/2013 | Ruus et al. |
| 2013/0079279 A1 | 3/2013 | Becker et al. |
| 2013/0085102 A1 | 4/2013 | Silvestre et al. |
| 2013/0096059 A1 | 4/2013 | Stechl et al. |
| 2013/0096060 A1 | 4/2013 | Stechl et al. |
| 2013/0116179 A1 | 5/2013 | Hess et al. |
| 2013/0203666 A1 | 8/2013 | Niemoeller et al. |
| 2013/0284912 A1 | 10/2013 | Vogel et al. |
| 2013/0296236 A1 | 11/2013 | Silvestre et al. |
| 2014/0148384 A1 | 5/2014 | Boka et al. |
| 2014/0206611 A1 | 7/2014 | Becker et al. |
| 2014/0248365 A1 | 9/2014 | Rademacher et al. |
| 2014/0371141 A1 | 12/2014 | Souhami et al. |

FOREIGN PATENT DOCUMENTS

| | | |
|---|---|---|
| CA | 1173388 A | 8/1984 |
| CA | 1258427 A | 8/1989 |
| CA | 1336329 C | 7/1995 |
| CA | 1341203 C | 3/2001 |
| CA | 2662084 A1 | 3/2008 |
| CN | 1276731 A | 12/2000 |
| CN | 1413582 A | 4/2003 |
| CN | 101366692 A | 2/2009 |
| CN | 101444618 A | 6/2009 |
| CN | 101454019 A | 6/2009 |
| CN | 101670096 A | 3/2010 |
| DE | 2219635 A1 | 11/1972 |
| DE | 3240177 A1 | 5/1983 |
| DE | 196 37 230 A1 | 3/1998 |
| DE | 102008003566 A1 | 7/2009 |
| DE | 102008003568 A1 | 7/2009 |
| DE | 102008053048 A1 | 4/2010 |
| EA | 006019 B1 | 8/2005 |
| EP | 0018609 B1 | 9/1983 |
| EP | 0046979 B1 | 9/1983 |
| EP | 0 124 826 A2 | 11/1984 |
| EP | 0132769 A1 | 2/1985 |
| EP | 0140084 A1 | 5/1985 |
| EP | 0 146 055 A1 | 6/1985 |
| EP | 0166529 A1 | 1/1986 |
| EP | 0180920 A2 | 5/1986 |
| EP | 0200383 A2 | 11/1986 |
| EP | 0211299 A2 | 2/1987 |
| EP | 0 214 823 A2 | 3/1987 |
| EP | 0 214 826 A2 | 3/1987 |
| EP | 0 224 885 | 6/1987 |
| EP | 0227938 A2 | 7/1987 |
| EP | 0229956 A1 | 7/1987 |
| EP | 0229998 A2 | 7/1987 |
| EP | 0254516 A2 | 1/1988 |
| EP | 0305760 A2 | 3/1989 |
| EP | 0368187 A2 | 5/1990 |
| EP | 0 375 437 A2 | 6/1990 |
| EP | 0383472 A2 | 8/1990 |
| EP | 0194864 B1 | 6/1992 |
| EP | 0 419 504 | 1/1994 |
| EP | 0600372 A1 | 6/1994 |
| EP | 0668282 A1 | 8/1995 |
| EP | 0668292 A2 | 8/1995 |
| EP | 0 678 522 A1 | 10/1995 |
| EP | 0837072 A2 | 4/1998 |
| EP | 0845265 A1 | 6/1998 |
| EP | 0885961 A1 | 12/1998 |
| EP | 1 076 066 A1 | 2/2001 |
| EP | 1172114 A2 | 1/2002 |
| EP | 1196444 A1 | 4/2002 |
| EP | 1222207 A1 | 7/2002 |
| EP | 1364029 A1 | 11/2003 |
| EP | 1523993 A1 | 4/2005 |
| EP | 1906991 A2 | 4/2008 |
| EP | 2112161 A2 | 10/2009 |
| EP | 2187950 A1 | 5/2010 |
| EP | 2324853 A1 | 5/2011 |
| EP | 2329848 A1 | 6/2011 |
| EP | 2389945 A1 | 11/2011 |
| EP | 0 921 812 B2 | 12/2011 |
| EP | 2387989 B1 | 7/2014 |
| FR | 2456522 A1 | 12/1980 |
| GB | 835 638 | 5/1960 |
| GB | 840 870 | 7/1960 |
| GB | 1527605 A | 10/1978 |
| GB | 1554157 A | 10/1979 |
| JP | S61212598 A | 9/1986 |
| JP | S6399096 A | 4/1988 |
| JP | H02218696 A | 8/1990 |
| JP | H02264798 A | 10/1990 |
| JP | H03540240 A | 9/1991 |
| JP | H06506444 A | 7/1994 |
| JP | 2001521004 A | 11/2001 |
| JP | 2002-516880 | 6/2002 |
| JP | 2003505347 A | 2/2003 |
| JP | 2005508895 A | 4/2005 |
| JP | 2005532365 A | 10/2005 |
| JP | 2006-137678 | 1/2006 |
| JP | 2006515267 A | 5/2006 |
| JP | 2007-204498 | 8/2007 |
| JP | 2009-091363 | 4/2009 |
| JP | 2009519961 A | 5/2009 |
| JP | 2012505852 A | 3/2012 |
| JP | 2012255040 A | 12/2012 |
| RU | 2008116057 A | 10/2009 |
| RU | 2386631 C2 | 4/2010 |
| TW | 157005 B | 5/1991 |
| TW | 562806 B | 11/2003 |
| WO | WO-8300288 A1 | 2/1983 |

(56) References Cited

FOREIGN PATENT DOCUMENTS

| | | |
|---|---|---|
| WO | WO-8806599 A1 | 9/1988 |
| WO | WO 89/10937 A1 | 11/1989 |
| WO | WO-9007522 A1 | 7/1990 |
| WO | WO-9011299 A1 | 10/1990 |
| WO | WO-9103550 A1 | 3/1991 |
| WO | WO-9116929 A1 | 11/1991 |
| WO | WO 92/00321 A1 | 1/1992 |
| WO | WO-9212999 A1 | 8/1992 |
| WO | WO93/18786 A1 | 9/1993 |
| WO | WO-9414461 A1 | 7/1994 |
| WO | WO 95/00550 | 1/1995 |
| WO | WO-9524183 A1 | 9/1995 |
| WO | WO-9604307 A1 | 2/1996 |
| WO | WO-9607399 A1 | 3/1996 |
| WO | WO-9611705 A1 | 4/1996 |
| WO | WO-9632414 A1 | 10/1996 |
| WO | WO-9634882 A1 | 11/1996 |
| WO | WO-9641606 A2 | 12/1996 |
| WO | WO-9701331 A2 | 1/1997 |
| WO | WO 97/48413 | 12/1997 |
| WO | WO 98/05351 A1 | 2/1998 |
| WO | WO 09/08873 A1 | 3/1998 |
| WO | WO 98/08531 A1 | 3/1998 |
| WO | WO 98/08873 A1 | 3/1998 |
| WO | WO-9808871 A1 | 3/1998 |
| WO | WO 98/19698 A1 | 5/1998 |
| WO | WO 98/30231 A1 | 7/1998 |
| WO | WO 98/35033 A1 | 8/1998 |
| WO | WO 98/39022 A1 | 9/1998 |
| WO | WO-9842749 A1 | 10/1998 |
| WO | WO 98/56406 | 12/1998 |
| WO | WO-9856418 A1 | 12/1998 |
| WO | WO 99/07404 A1 | 2/1999 |
| WO | WO 99/21573 | 5/1999 |
| WO | WO 99/21578 | 5/1999 |
| WO | WO 99/25727 A2 | 5/1999 |
| WO | WO 99/25728 A1 | 5/1999 |
| WO | WO-9924071 A1 | 5/1999 |
| WO | WO 99/40788 A1 | 8/1999 |
| WO | WO 99/43708 A1 | 9/1999 |
| WO | WO 99/46283 A1 | 9/1999 |
| WO | WO 99/62558 A1 | 12/1999 |
| WO | WO-0023098 A1 | 4/2000 |
| WO | WO-0023099 A1 | 4/2000 |
| WO | WO-0029013 A1 | 5/2000 |
| WO | WO-0041546 A2 | 7/2000 |
| WO | WO 00/66629 A1 | 11/2000 |
| WO | WO-0074736 A1 | 12/2000 |
| WO | WO 01/04156 A1 | 1/2001 |
| WO | WO-0100223 A2 | 1/2001 |
| WO | WO-0102039 A1 | 1/2001 |
| WO | WO-0112155 A1 | 2/2001 |
| WO | WO-0121154 A2 | 3/2001 |
| WO | WO 01/24814 | 4/2001 |
| WO | WO 01/25278 A1 | 4/2001 |
| WO | WO-0128555 A1 | 4/2001 |
| WO | WO-0137808 A1 | 5/2001 |
| WO | WO-0143762 A2 | 6/2001 |
| WO | 01/51071 A2 | 7/2001 |
| WO | WO-0152937 A1 | 7/2001 |
| WO | WO-0193837 A2 | 12/2001 |
| WO | WO 02/000243 | 1/2002 |
| WO | WO-0224214 A2 | 3/2002 |
| WO | WO-02064115 A1 | 8/2002 |
| WO | WO-02065985 A2 | 8/2002 |
| WO | WO-02066628 A2 | 8/2002 |
| WO | WO-02068660 A1 | 9/2002 |
| WO | WO-02070722 A1 | 9/2002 |
| WO | WO 02/079250 A1 | 10/2002 |
| WO | WO-02076495 A1 | 10/2002 |
| WO | WO 03/002021 | 1/2003 |
| WO | 03020201 A2 | 3/2003 |
| WO | WO-03035028 A1 | 5/2003 |
| WO | WO-03035051 A2 | 5/2003 |
| WO | WO-03044210 A2 | 5/2003 |
| WO | WO 03/053339 A2 | 7/2003 |
| WO | 03066084 A1 | 8/2003 |
| WO | WO 03/094951 | 11/2003 |
| WO | WO 03/094956 | 11/2003 |
| WO | WO 03/101395 | 12/2003 |
| WO | WO-03105888 A1 | 12/2003 |
| WO | WO 2004/005342 A1 | 1/2004 |
| WO | WO2004/035623 A2 | 4/2004 |
| WO | WO-2004045592 A2 | 6/2004 |
| WO | WO 2004050115 | 6/2004 |
| WO | WO-2004064862 A1 | 8/2004 |
| WO | WO 2004/080480 | 9/2004 |
| WO | WO-2004078196 A1 | 9/2004 |
| WO | WO-2004078197 A1 | 9/2004 |
| WO | WO-2004078198 A1 | 9/2004 |
| WO | WO-2004096854 A2 | 11/2004 |
| WO | WO 2004/107979 A1 | 12/2004 |
| WO | WO-2004105781 A2 | 12/2004 |
| WO | WO 2005/021022 A2 | 3/2005 |
| WO | WO2005/028516 A2 | 3/2005 |
| WO | WO-2005023291 A2 | 3/2005 |
| WO | 2005046716 A1 | 5/2005 |
| WO | WO2005048950 A2 | 6/2005 |
| WO | WO2005/112949 A1 | 12/2005 |
| WO | WO 2005/117948 | 12/2005 |
| WO | WO-2006000567 A2 | 1/2006 |
| WO | WO-2006015879 A1 | 2/2006 |
| WO | 2006029634 A | 3/2006 |
| WO | 2006051103 A2 | 5/2006 |
| WO | WO 2006/051110 A2 | 5/2006 |
| WO | WO-2006058620 A2 | 6/2006 |
| WO | WO2006083952 A2 | 8/2006 |
| WO | WO2006/110551 A2 | 10/2006 |
| WO | WO-2007001150 A2 | 1/2007 |
| WO | WO 2007006307 | 1/2007 |
| WO | WO-2007024700 A2 | 3/2007 |
| WO | WO-2007028394 A2 | 3/2007 |
| WO | WO-2007031187 A1 | 3/2007 |
| WO | WO-2007035665 A1 | 3/2007 |
| WO | WO 2007/037607 | 4/2007 |
| WO | WO 2007/044867 A2 | 4/2007 |
| WO | WO-2007036299 A2 | 4/2007 |
| WO | WO-2007050656 A2 | 5/2007 |
| WO | WO 2007/081824 A2 | 7/2007 |
| WO | WO 2007/082381 A1 | 7/2007 |
| WO | WO-2007075534 A2 | 7/2007 |
| WO | WO 2007081792 | 7/2007 |
| WO | WO 2007/095288 A2 | 8/2007 |
| WO | 2007104786 A1 | 9/2007 |
| WO | WO 2007/109221 | 9/2007 |
| WO | 2007/120899 A2 | 10/2007 |
| WO | 2007113205 A1 | 10/2007 |
| WO | WO 2008/006496 | 1/2008 |
| WO | WO 2008/006496 A1 | 1/2008 |
| WO | WO-2008013938 A2 | 1/2008 |
| WO | 2008/021560 | 2/2008 |
| WO | WO-2008023050 A1 | 2/2008 |
| WO | WO 2008/034881 | 3/2008 |
| WO | WO-2008028914 A1 | 3/2008 |
| WO | WO 2008/124522 A2 | 10/2008 |
| WO | WO2008/133908 A2 | 11/2008 |
| WO | WO-2008145323 A1 | 12/2008 |
| WO | WO 2009/004627 | 1/2009 |
| WO | WO-2009030498 A2 | 3/2009 |
| WO | WO-2009030499 A1 | 3/2009 |
| WO | WO 2009/048959 A1 | 4/2009 |
| WO | WO-2009039963 A1 | 4/2009 |
| WO | WO 2009/056569 | 5/2009 |
| WO | WO 2009/063072 | 5/2009 |
| WO | WO 2009/087081 A2 | 7/2009 |
| WO | WO 2009/087082 | 7/2009 |
| WO | WO-2009089181 A1 | 7/2009 |
| WO | WO 2009/098318 | 8/2009 |
| WO | WO2009/102467 A2 | 8/2009 |
| WO | 2009/143014 | 11/2009 |
| WO | WO 2009/134380 A2 | 11/2009 |
| WO | 2010030670 A2 | 3/2010 |
| WO | WO2010/044867 A1 | 4/2010 |
| WO | WO-2010043566 A2 | 4/2010 |

(56) References Cited

FOREIGN PATENT DOCUMENTS

| WO | WO 2010089304 | 8/2010 |
|---|---|---|
| WO | WO-2010092163 A2 | 8/2010 |
| WO | WO 2010/138671 | 12/2010 |
| WO | 2011003822 A2 | 1/2011 |
| WO | 2011003823 A1 | 1/2011 |
| WO | WO-2011017554 A2 | 2/2011 |
| WO | 2011029892 A2 | 3/2011 |
| WO | WO 2011/012719 | 3/2011 |
| WO | WO 2011/058082 A1 | 5/2011 |
| WO | WO 2011/058083 A1 | 5/2011 |
| WO | WO 2011089203 | 7/2011 |
| WO | WO-2011103575 A1 | 8/2011 |
| WO | WO-2011122921 A2 | 10/2011 |
| WO | WO-2011128374 A1 | 10/2011 |
| WO | WO-2011144673 A2 | 11/2011 |
| WO | WO-2011144674 A2 | 11/2011 |
| WO | WO-2011147980 A1 | 12/2011 |
| WO | WO-2011157402 A1 | 12/2011 |
| WO | WO-2011160066 A1 | 12/2011 |
| WO | WO-2012012352 A2 | 1/2012 |
| WO | WO-2012028172 A1 | 3/2012 |
| WO | WO-2012055967 A2 | 5/2012 |
| WO | WO-2012065996 A1 | 5/2012 |
| WO | WO-2012066086 A1 | 5/2012 |
| WO | WO 2012/080320 | 6/2012 |
| WO | WO-2012104342 A1 | 8/2012 |
| WO | WO-2012125569 A2 | 9/2012 |
| WO | WO-2012156296 A1 | 11/2012 |
| WO | WO-2012156299 A1 | 11/2012 |
| WO | WO-2012177929 A2 | 12/2012 |
| WO | WO-2013060850 A1 | 5/2013 |
| WO | WO 2014/017849 | 1/2014 |
| WO | WO 2014/118355 | 8/2014 |
| WO | 2014/202483 | 12/2014 |
| WO | WO 2015/059302 | 4/2015 |

OTHER PUBLICATIONS

English translation of a Notice of Opposition filed against parallel application EC SP-12-11890-PCT, Year 2011.

International Search Report dated Mar. 23, 2011 issued in PCT/EP2010/067250.

U.S. Appl. No. 13/509,507 filed Jul. 30, 2012.

U.S. Appl. No. 13/509,542 filed Aug. 2, 2012.

U.S. Appl. No. 60/143,591 filed Jul. 12, 1999.

English-language translation of International Search Report dated Oct. 4, 2010 received from the European Patent Office from related International Application No. PCT/EP2010/059438 and U.S. Appl. No. 13/382,442.

English-language translation of Official Action dated Feb. 24, 2014 received from the Colombian Patent Office from related Application No. 12 001866.

English-language translations of Bolivian Oppositions dated Oct. 25, 2012 filed by the Chamber of the Pharmaceutical Industry Bolivian a against Application No. SP-0204-201 0.

International Preliminary Examination Report from PCT/DK03/00651 dated Jan. 31, 2005.

International Preliminary Report on Patentability dated Jan. 10, 2012 issued in PCT/EP2010/059438.

International Preliminary Report on Patentability dated Jun. 12, 2012 issued in PCT/EP2010/069184.

International Preliminary Report on Patentability dated Jun. 21, 2012 from related Application No. PCT/ EP2010/069184 and U.S. Appl. No. 13/382,442.

International Search Report and Written Opinion dated Jun. 17, 2011 received from the European Patent Office from related Application No. PCT/EP2010/059436.

International Search Report from PCT/DK03/00651 dated Oct. 2, 2003.

United States Office Action dated May 23, 2013 issued in U.S. Appl. No. 13/509,542.

United States Final Office Action dated Nov. 21, 2013 issued in U.S. Appl. No. 13/509,542.

United States Office Action dated Apr. 2, 2014 issued in U.S. Appl. No. 13/509,542.

Noble, S. L. et al., Insulin Lispro: A Fast-Acting Insulin Analog, Am Fam Physician, (Jan 15, 1998), vol. 57, No. 2, pp. 279-286.

U.S. Appl. No. 14/303,895 filed Jun. 13, 2014 to Souhami et al.

U.S. Appl. No. 14/172,151 filed Feb. 4, 2014 to Bley, et al.

Brange J., "Design of Insulin Analogues for Meal-Related Therapy", J. Diabetes Complications 7(2):106-112 (Apr.-Jun. 1993), Abstract only.

Brange, Jens et al. "Toward Understanding Insulin Fibrillation," Journal of Pharmaceutical Sciences (1997), vol. 86, No. 5, pp. 517-525.

Byrne et al., "Inhibitory Effects of Hyperglycaemia on Fed Jejunal Motility: Potential Role of Hyperinsulinaemia," Euro. J. Clin. Invest. 28:72-78 (1998).

Chen et al., Tissue-specific Expression of Unique mRNAs That Encode Proglucagon-derived Peptides or Exendin 4 in the Lizard, J. Biol. Chem. 272:4108-4115 (1997).

D'Alessio et al., "Glucagon-like Peptide 1 Enhances Glucose Tolerance Both by Stimulation of Insulin Release and by Increasing Insulin-independent Glucose Disposal," J. Clin. Invest. 93:2263-2266 (1994).

Deacon et al., "Dipeptidyl Peptidase IV Inhibition Potentiates the Insulinotropic Effect of Glucagon-Like Peptide 1 in the Anesthetized Pig," Diabetes 47:764-769, 1998.

Deacon et al., "Dipeptidyl Peptidase IV Resistant Analogues of Glucagon-Like Peptide-1 Which Have Extended Metabolic Stability and Improved Biological Activity," Diabetologia 41 :271-278, 1998.

Drucker, "The Biology of Incretin Hormones," Cell Metab. 3:153-165, 2006.

Drucker, D., "Glucagon-Like Peptides," Diabetes 47:159-169 (1998).

Drucker, D., "Mini review: The Glucagon-Like Peptides," Endocrinology 521-527. (2001).

Goke et al., "Distribution of GLP-1 Binding Sites in the Rat Brain: Evidence that Exendin-4 is a Ligand of Brain GLP-1 Binding Sites," Eur. J. Neurosci. 7:2294-3000, 1995.

Goke et al., "Exendin-4 is a High Potency Agonist and Truncated Exendin-(9-39)-amide an Antagonist at the Glucagon-like Peptide 1-(7-36)-amide Receptor of Insulin-secreting beta-Cells," J. Biol. Chem. 268:19650-19655 (1993).

Greig et al., "Once Daily Injection of Exendin-4 to Diabetic Mice Achieves Long-Term Beneficial Effects on Blood Glucose Concentrations." Diabetologia 42:45-50 (1999).

Gutniak et al., "Antidiabetogenic Effect of Glucagon-Like Peptide-1 (7-36) Amide in Normal Subjects and Patients with Diabetes Mellitus," N. Engl. J. Med. 326:1316-1322, 1992.

Heinrich et al., "Pre-proglucagon messenger ribonucleic acid: nucleotide and encoded amino acid sequences of the rat pancreatic complementary deoxyribonucleic acid," Endocrinol. 115(6):2176-2181, 1984.

Hoist (1999), Curr. Med. Chem 6:1005.

Kleinman et al., "Isolation and characterization of exendin-4, an exendin-3 analogue, from Heloderma suspectum venom. Further evidence for an exendin receptor on dispersed acini from guinea pig pancreas," J. Bio. Chem., 267:7402-7405, 1992.

Knudsen L.B. et al., "Potent Derivatives of Glucagon-Like Peptide-1 With Pharmacokinetic Properties Suitable for Once Daily Administration", J. Med. Chem. 43:1664-1669 (2000).

Kolterman et al., "Synthetic Exendin-4 (Exenatide) Significantly Reduces Postprandial and Fasting Plasma Glucose in Subjects with Type 2 Diabetes," J. Clin. Endocrine/. Metab. 88:3082-3089, 2003.

Larsen et al., "Sequence-Assisted Peptide Synthesis (SAPS)," J. Pept. Res. 52:470-476, 1998.

Lopez-Delgado et al., Endocrinology 139:2811, 1998.

Merrifield, B., "Solid Phase Synthesis." Science 232:341-347 (1986).

Nathan et al., "Insulinotropic Action of Glucagonlike Peptide-1-(7-37) in Diabetic and Nondiabetic Subjects," Diabetes Care 15:270-276, 1992.

(56) References Cited

OTHER PUBLICATIONS

Nauck et al., "Effects of Subcutaneous Glucagon-Like Peptide 1 (GLP-1 [7-36 Amide]) in Patients with NIDDM," Diabetologia 39:1546-1553, 1996.
Nauck et al. (1997) Exp Clin Endocrinol Diabetes 105: 187.
Nauck et al., "Glucagon-Like Peptide 1 and its Potential in the Treatment of Non-Insulin-Dependent Diaetes Mellitus," Horm. Metab. Res. 29:411-416 (1997).
Needleman et al., "A General Method Applicable to the Search for Similarities in the Amino Acid Sequence of Two Proteins," J. Mol. Biol. 48:443-453 (1970).
Nielsen et al., "Pharmacology of Exenatide (Synthetic Exendin-4): A Potential Therapeutic for Improved Glycemic of Control of Type 2 Diabetes," Regul. Pept. 117:77-88, 2004.
Orskov, C., "Glucagon-like Peptide-1, a New Hormone of the Entero-insular Axis," Diabetologia 35:701-711 (1992).
Pederson et al., "Improved Glucose Tolerance in Zucker Fatty Rats by Oral Administration of the Dipeptidyl Peptidase IV Inhibitor Isoleucine Thiazolidide." Diabetes 47:1253-1258 (1998).
Pohl et al., "Molecular Cloning of the Heloderman and Exendin-4 cDNAs in the Lizard," J. Biol. Chem. 273:9778-9784 (1998).
Raufman, "Bioactive Peptides from Lizard Venoms," Regul. Pept. 61:1-18, 1996.
Ritzel et al., "A Synthetic Glucagon-Like Peptide-1 Analog with Improved Plasma Stability," J. Endocrine/. 159:93-102, 1998.
Schubert-Zsilavecz, Manfred et al., "Better blood sugar control in diabetics. Insulin glargin—a long acting insulin D analogue," Pharmazie in Unserer Zeit (2001), pp. 125-130 (With English language Abstract).
Tessari P. et al., "Insulin in Methionine and Homocysteine Kinetics in Healthy Humans: Plasma Vs. Intracellular Models", Am J. Physiol Endocrinol Metab 288(6):E1270-E1276 (Jun. 2005).
Tews, D. et al., "Enhanced Protection against Cytokine- and Fatty Acid-induced Apoptosis in Pancreatic Beta Cells by Combined Treatment with Glucagon-like Peptide-1 Receptor Agonists and Insulin Analogues," Hormone and Metabolic Research (2008), vol. 40, No. 3, pp. 172-180.
The New England Journal of Medicine (1993), vol. 329, No. 14, pp. 977-986.
Uttenthel et al., "Molecular forms of flucagon-like peptide-1 in human pancreas and glucagonomas," J. Clin. Endocrinol. Metabol. 61(3):472-479, 1985.
Wan, Zhuli et al., "Enhancing the Activity of Insulin at the Receptor Interface: Crystal Structure and Photo-Cross-Linking of A8 Analogues," Biochemistry (2004), vol. 43, pp. 16119-16133.
Weiss M.A. et al., "Activities of Monomeric Insulin Analogs at Position A8 Are Uncorrelated With Their Thermodynamic Stabilities", The Journal of Biological Chemistry 276(43):40018-40024 (Oct. 26, 2001).
Yu et al., "Effect of Zinc Sulphate and Zinc Methionine on Growth, Plasma Growth Hormone Concentration, Growth Hormone Receptor and Insulin-Like Growth Factor-1 Gene Expression in Mice", Clin Exp Pharmacal Physiol 32 (4):273-278 (Apr. 2005), Abstract only.
U.S. Final Office Action dated Jul. 17, 2013 issued in related U.S. Appl. No. 13/382,442.
U.S. Office Action dated Apr. 10, 2013 issued in related U.S. Appl. No. 13/382,772.
U.S. Office Action dated Dec. 19, 2013 issued in related U.S. Appl. No. 13/382,442.
U.S. Office Action dated Nov. 21, 2013 issued in related U.S. Appl. No. 13/382,772.
U.S. Office Action dated Nov. 7, 2012 issued in related U.S. Appl. No. 13/382,442.
U.S. Office Action dated Mar. 21, 2011 issued in related U.S. Appl. No. 12/435,295.
U.S. Office Action dated Jun. 13, 2014 issued in related U.S. Appl. No. 13/382,442.
U.S. Office Action dated Jun. 3, 2014 issued in related U.S. Appl. No. 13/382,772.

Arnolds & Rave, "Basal insulin glargine vs prandial insulin lispro in type 2 diabetes," Lancet 378(9636):370-71 (2008).
English translation of Official Notice of an Opposition filed against Venezuelan Patent Application No. 2010-001775, Sep. 26, 2013, pp. 1-6.
English translation of Notice of Reasons for Rejection for Japanese Patent Application No. 2012-538331 dispatched on Feb. 25, 2014, pp. 1-5.
Campbell et al., "Insulin Glargine," Clin. Therapeutics 23(12):1938-57 (2001).
DrugBank, "Insulin glargine," available online at http://www.drugbank.ca/drugs/DB00047, 16 pages (accessed online Sep. 25, 2014).
Eng et al., "Isolation and characterization of exendin-4, an exendin-3 analogue, from Heloderma suspectum venom. Further evidence for an exendin receptor on dispersed acini from guinea pig pancreas," J Biol Chem 267(11):7402-5 (1992).
Nauck et al., "Effects of Subcutaneous Glucagon-Like Peptide 1 (GLP-1 [7-36 Amide]) in Patients with NIDDM," Diabetologia 39(12):1546-53 (1996).
"Suspension" Taber's Cyclopedic Medical Dictionary, 19th Edition, p. 2097 (F.A. Davis Co., Philadelphia 2001).
"Suspension" Stedman's Medical Dictionary, 20th Edition, p. 1450 (Williams & Wilkins Co., Baltimore 1961).
Final Rejection issued in U.S. Appl. No. 13/509,542, mailed Jan. 28, 2015, pp. 1-26.
Non-Final Rejection issued in U.S. Appl. No. 13/382,442; mailed Feb. 5, 2015, pp. 1-31.
Final Rejection issued in U.S. Appl. No. 13/382,772; mailed Feb. 10, 2015, pp. 1-36.
Non-Final Rejection issued in U.S. Appl. No. 13/382,772; mailed Sep. 29, 2014, pp. 1-33.
U.S. Appl. No. 13/382,442; filed Mar. 21, 2012.
U.S. Appl. No. 13/382,772; filed May 29, 2012.
Bhatt et al., "Chemical pathways of peptide degradation. I. Deamidation of adrenocorticotropic hormone," Pharm 7(6):593-9 (1990).
Brange & Langkjeer, "Chemical stability of insulin 3. Influence of excipients, formulation, and pH," Acta Pharma. Nord. 4(3):149-58 (1992).
Brange & Langkjaer, "Insulin Structure and Stability" Chapter 11; Pharm Biotechnol 5:315-50 (1993).
"Buffer"Oxford Dictionary of Biochemistry and Molecular Biology, Oxford University Press, 2001, p. 83.
FDA label of Apidra®, May 2014, pp. 1-35.
FDA label of Humalog®, Mar. 2013, pp. 1-27.
FDA label of Lantus®, Oct. 2013, pp. 1-44.
Actrapid® summary of product characteristics, Apr. 2011, pp. 1-11.
Actrapid® prescribing information, Apr. 2011, pp. 1-4.
Apidra® prescribing information, Apr. 2012, pp. 1-6.
Berlinsulin® H summary of product characteristics, Apr. 2012, pp. 1-11.
Berlinsulin® H prescribing information, Apr. 2012, pp. 1-4.
Humalog® prescribing information, Apr. 2012, pp. 1-6.
Insuman® Comb25 prescribing information, Feb. 2011, pp. 1-4.
Insuman® Infusat prescribing information, Feb. 2011, pp. 1-4.
Lantus® prescribing information, May 2012, pp. 1-6.
Levemir® prescribing information, Dec. 2011, pp. 1-6.
Novolog® product information, Oct. 2009, pp. 1-4.
NovoMix® prescribing information, Feb. 2011, pp. 1-5.
NovoRapid® prescribing infonnation, Jul. 2012, pp. 1-5.
Galloway & Root, "New forms of insulin," Diabetes 21 (2 Suppl):637-48 (1972).
"Insulin Aspart Injection." Formulated Preparations: Specific Monographs. British Pharmacopoeia 3. pp. 1-3 (2012).
Jackson et al., "Neutral regular insulin," Diabetes 21(4):235-45 (1972).
Lens, "The terminal carboxyl groups of insulin," Biochimica et Biophysica Acta 3:367-70 (1949).
Levene & Simms, "Calculation of isoelectric point," J Bioi Chern. 55:801-13 (1923).

(56) References Cited

OTHER PUBLICATIONS

Lill, "Production of fast-acting insulins and delayed-release insulins—how can this problem be solved by technology? Insulin formulations," Pharmazie in unserer Zeit 30(1):56-61 (2001). (English Translation Included).
Mecklenburg & Guinn, "Complications of insulin pump therapy: the effect of insulin preparation," Diabetes Care 8 (4):367-70 (1985).
Muzaffar et al., "The Mechanism of Enhanced Insulin Amyloid Fibril Formation by NaClIs Better Explained by a Conformational Change Model," PLoS One, Nov. 21, 2011, pp. 1-11, 6(11):e27906.
Patel & Borchardt, "Chemical pathways of peptide degradation. II. Kinetics of deamidation of an asparaginyl residue in a model hexapeptide," Pharmaceutical Research 7(7):703-11 (1990).
Tyler-Cross Schirch, "Effects of amino acid sequence, buffers, and ionic strength on the rate and mechanism of deamidation of asparagine residues in small peptides," J Biol Chem. 266(33):22549-56 (1991).
U.S. Appl. No. 14/172,151, filed Feb. 4, 2014 to Bley et al.
Non-Final Rejection issued in U.S. Appl. No. 14/172,151; mailed Mar. 24, 2015, pp. 1-16.
Final Rejection issued in U.S. Appl. No. 14/172,151; mailed Jul. 20, 2015, pp. 1-18.
Extended European Search Report for European Application No. 13 305 126; dated Apr. 11, 2013, pp. 1-7.
International Search Report by the ISA for International Application No. PCT/EP2014/051976; dated Mar. 4, 2014, pp. 1-3.
Non-Final Rejection issued in U.S. Appl. No. 13/509,542; mailed Aug. 11, 2015, pp. 1-30.
Search Report of the Indecopi for Patent Application in Peru No. 000643-2012/DIN, dated Jul. 23, 2015, pp. 1-2.
U.S. Appl. No. 13/123,835, published Sep. 30, 2011, Werner et al.
U.S. Appl. No. 13/633,496, published Oct. 2, 2012, Stechl et al.
U.S. Appl. No. 13/661,476, published Oct. 26, 2012, Silvestre et al.
U.S. Appl. No. 14/303,895, published Jun. 13, 2014, Souhami et al.
U.S. Appl. No. 13/633,563, published Oct. 2, 2012, Stechl et al.
U.S. Appl. No. 12/617,805, published Nov. 13, 2009, Silvestre et al.
U.S. Appl. No. 12/617,811, published Nov. 13, 2009, Silvestre et al.
U.S. Appl. No. 14/220,562, published Mar. 20, 2014, Becker et al.
U.S. Appl. No. 13/700,631, published Nov. 11, 2012, Becker et al.
U.S. Appl. No. 13/819,114, published Apr. 29, 2013, Boka et al.
U.S. Appl. No. 13/363,956, published Feb. 1, 2012, Silverstre et al.
U.S. Appl. No. 13/432,811, published Mar. 28, 2012, Boka et al.
U.S. Appl. No. 13/469,633, published May 11, 2012, Ruus et al.
U.S. Appl. No. 13/467,707, published May 9, 2012, Niemoller et al.
U.S. Appl. No. 13/468,422, published May 10, 2012, Silvestre et al.
U.S. Appl. No. 13/467,757, published May 9, 2012, Silvestre et al.
U.S. Appl. No. 13/595,590, published Aug. 27, 2012, Niemoller et al.
U.S. Appl. No. 13/602,913, published Sep. 4, 2012, Hess et al.
NHSC—National Horizon Scanning Center, "AVE0010 (ZP10) for type 2 diabetes mellitus" University of Birmingham, England; pp. 1-6 (Dec. 2008).
Non-Final Rejection issued in U.S. Appl. No. 13/819,114; mailed Dec. 2, 2015, pp. 1-14.
Search Report of the Intellectual Property Office of Singapore for Patent Application No. 102015008711, dated Nov. 2, 2015, pp. 1-3.
Chi et al., "Excipients and their Effects on the Quality of Biologics" pp. 1-9, (May 2012).
Non-Final Rejection issued in U.S. Appl. No. 13/382,442; mailed Mar. 31, 2016, pp. 1-29.
International Search Report by the ISA for International Application No. PCT/EP2015/079285; dated Mar. 9, 2016, pp. 1-7.
English translation of the TIPO Search Report for ROC Patent Application No. 104116749, dated Feb. 22, 2016, one page.
18th World Health Congress (Helsinki). WMA Declaration of Helsinki—Ethical Principles for Medical Research Involving Human Subjects; WMA; Jun. 1964, pp. 1-8.

Abbas T., et al., "Impairment of Synaptic Plasticity and Memory formation in GLP-1 Receptor Ko Mice: Interaction Between Type 2 Diabetes and Alzheimer's Disease," Behavioural Brain Research, 2009, vol. 205 (1), pp. 265-271.
Action to Control Cardiovascular Risk in Diabetes Study Group, "Effects of Intensive Glucose Lowering in Type 2 Diabetes," The New England Journal of Medicine, 2008, vol. 358 (24), pp. 2545-2559.
Aderinwale O.G., et al., "Current Therapies and New Strategies for the Management of Alzheimer's Disease," American Journal of Alzheimer's Disease and Other Dementias, 2010, vol. 25 (5), pp. 414-424.
Agholme L., et al., "An in Vitro Model for Neuroscience: Differentiation of SH-SY5Y Cells into Cells with Morphological and Biochemical Characteristics of Mature Neurons," Journal of Alzheimer's Disease, 2010, vol. 20, pp. 1069-1082.
Ahren et al., Abstract "Efficacy and Safety of Lixisenatide QD Morning and Evening Injections vs Placebo in T2DM Inadequately Controlled on Metformin (GetGoal-M)" Oral presentation O-0591 presented at the World Diabetes Congress in Dubai, Dec. 5-8, 2011, one page.
Ahualli J., "The Double Duct Sign," Radiology, 2007, vol. 244 (1), pp. 314-315.
Akbar D.H., "Sub-Optimal Postprandial Blood Glucose Level in Diabetics Attending the Outpatient Clinic of a University Hospital," Saudi Med Journal, 2003, vol. 24 (10), pp. 1109-1112.
American Diabetes Association (ADA) Committee Report—The Expert Committee on the Diagnosis and Classification of Diabetes Mellitus—Report of the Expert Committee on the Diagnosis and Classification of Diabetes Mellitus, Diabetes Care, 21(Supplement 1): S5-S19 (Jan. 1998).
Aoki K., et al., "Hydrolysis of Nonionic Surfactants," Annual Report Takeda Research Laboratory, 1968, vol. 27, pp. 172-176.
Arnolds S., et al., "Further Improvement in Postprandial Glucose Control with Addition of Exenatide or Sitagliptin to Combination therapy with Insulin Glargine and Metformin- A Proof-of-Concept Study," Diabetes Care, 2010, vol. 33 (7), pp. 1509-1515.
Auerbach R., et al., "Angiogenesis Assays: Problems and Pitfalls," Cancer Metastasis Reviews, 2000, vol. 19 (1-2), pp. 167-172.
Bakaysa D.L., et al., "Physicochemical Basis for the Rapid Time-Action of Lysb28 Prob29-Insulin: Dissociation of a Protein-Ligand Complex," Protein science, 1996, vol. 5 (12), pp. 2521-2531.
Banks W.A., et al., "Brain Uptake of the Glucagon-Like Peptide-1 Antagonist Exendin(9-39) After intranasal Administration," The Journal of Pharmacology and Experimental Therapeutics, 2004, vol. 309 (2), pp. 469-475.
Barnett A., "Dosing of Insulin Glargine in the Treatment of Type 2 Diabetes," Clinical Therapeutics, 2007, vol. 29 (6), pp. 987-999.
Barnett A.H., et al., "Tolerability and Efficacy of Exenatide and Titrated Insulin Glargine in Adult Patients with Type 2 Diabetes Previously Uncontrolled with Metformin or a Sulfonylurea: A Multinational, Randomized, Open-Label, Two-Period, Crossover Noninferiority Trial," Clinical Therapeutics, 2007, vol. 29 (11), pp. 2333-2348.
Barnett A.H., "Insulin Glargine in the Treatment of Type 1 and Type 2 Diabetes," Vascular Health and Risk Management, 2006, vol. 2 (1), pp. 59-67.
Barnett A.H., "Lixisenatide: Evidence for its Potential Use in the Treatment of Type 2 Diabetes," Core Evidence, 2011, vol. 6, pp. 67-79.
Barnett R.O., et al., "Insulin Analogues," Lancet, 1997, vol. 349 (9044), pp. 47-51.
Behar J., et al., "Functional Gallbladder and Sphincter of Oddi Disorders," Gastroenterology, 2006, vol. 130 (5), pp. 1498-1509.
Beintema J.J., et al., "Molecular Evolution of Rodent Insulins," Molecular Biology and Evolution, 1987, vol. 4 (1), pp. 10-18.
Berger M., "Towards More Physiological Insulin Therapy in the 1990s a Comment," Diabetes Research and Clinical Practice, 1989, vol. 6 (4), pp. S25-S31.
Berlie H., et al., "Glucagon-Like Peptide-1 Receptor Agonists as Add-On therapy to Basal Insulin in Patients with Type 2 Diabetes: A Systematic Review," Diabetes, Metabolic Syndrome and Obesity: Targets and Therapy, 2012, vol. 5, pp. 165-174.

(56) References Cited

OTHER PUBLICATIONS

Bertram L., et al., "The Genetics of Alzheimer Disease: Back to the Future," Neuron, 2010, vol. 68 (2), pp. 270-281.

Best, Mathmatics and Statistics pp. 1-39, 1988.

Bethel M.A., et al., "Basal Insulin Therapy in Type 2 Diabetes," The Journal of the American Board of the Family Practice, 2005, vol. 18 (3), pp. 199-204.

Blanchard V., et al., "Time Sequence of Maturation of Dystrophic Neurites Associated with Abeta Deposits in APP/PS1 Transgenic Mice," Experimental Neurology, 2003, vol. 184, pp. 247-263.

Bland J.M., et al., "Measurement Error," British Medical Journal, 1996, vol. 312 (7047), p. 1654.

Bolen S., et al., "Systematic Review: Comparative Effectiveness and Safety of oral Medications for Type 2 Diabetes Mellitus," Annals of Internal Medicine, 2007, vol. 147 (6), pp. 386-399.

Bolli et al., "Efficacy and safety of lixisenatide once-daily versus placebo in patients with type 2 diabetes mellitus insufficiently controlled on metformin (GetGoal-F1)." Presentation Abstract No. 784, EASD Meeting Sep. 12-16, 2014.

Bolli G.B., et al., "Efficacy and Safety of Lixisenatide once Daily Vs Placebo in People with Type 2 Diabetes Insufficiently Controlled on Metformin (Getgoal-F1)," Diabetic Medicine, 2014, vol. 31 ( 2), pp. 176-184.

Bolli G.B., "The Pharmacokinetic Basis of Insulin Therapy in Diabetes Mellitus," Diabetes Research and Clinical Practice, 1989, vol. 6 (4), pp. S3-15.

Boutajangout A., et al., "Characterisation of Cytoskeletal Abnormalities in Mice Transgenic for Wild-Type Human Tau and Familial Alzheimer's Disease Mutants of APP and Presenilin-1," Neurobiology of Disease, 2004, vol. 15 (1), pp. 47-60.

Boutajangout a., et al., "Increased Tau Phosphorylation But Absence of formation of Neurofibrillary Tangles in Mice Double Transgenic for Human Tau and Alzheimer Mutant (M146L) Presenilin-1," Neuroscience Letters, 2002, vol. 318 (1), pp. 29-33.

Brange "Galenics of Insulin" 1987, p. 35-36.

Brange J., et al., "Monomeric Insulins and their Experimental and Clinical Implications," Diabetes Care, 1990, vol. 13 (9), pp. 923-954.

Brange J., et al., "Neutral Insulin Solutions Physically Stabilized by Addition of Zn2+," Diabetic Medicine, 1986, vol. 3, pp. 532-536.

Brod M., et al., "Adherence Patterns in Patients with Type 2 Diabetes on Basal Insulin Analogues: Missed, Mistimed and Reduced Doses," Current Medical Research and Opinion, 2012, vol. 28 (12), pp. 1933-1946.

Brod M., et al., "Examining Correlates of Treatment Satisfaction for injectable Insulin in Type 2 Diabetes: Lessons Learned from a Clinical Trial Comparing Biphasic and Basal Analogues," Health Quality of Life Outcomes, 2007, vol. 5, pp. 1-10.

Broderick J., et al., "Guidelines for the Management of Spontaneous intracerebral Hemorrhage in Adults," Circulation, 2007, vol. 116 (16), pp. e391-e413.

Brown J.B., et al., "Slow Response to Loss of Glycemic Control in Type 2 Diabetes Mellitus," American Journal of Managed Care, 2003, vol. 9 (3), pp. 213-217.

Burgermeister W., et al., "The Isolation of Insuin from the Pancreas," Insulin, 1975, vol. Part 2, pp. 715-727.

Burke G.T., et al., "Nature of the B10 Amino Acid Residue Requirements for High Biological Activity of Insulin," International Journal of Peptide and Protein Research, 1984, vol. 23 (4), pp. 394-401.

Buse J.B., et al., "Use of Twice-Daily Exenatide in Basal Insulin-Treated Patients with Type 2 Diabetes: A Randomized, Controlled Trial," Annals of Internal Medicine, 2011, vol. 154 (2), pp. 103-112.

Byetta—Summary of Product Characteristics, updated Jan. 27, 2015, last accessed Apr. 18, 2015, pp. 1-12.

Cadario B., "Sitagliptin," Drug Information Perspectives, 2010, vol. 30 (4), pp. 1-6.

Campas C., et al., "Ave-0010 GLP-1 Receptor Agonist Treatment of Diabetes," Drugs of the Future, 2008, vol. 33 (10), pp. 838-840.

Casas C., et al., "Massive CA1/2 Neuronal Loss with Intraneuronal and N-Terminal Truncated Abeta42 Accumulation in a Novel Alzheimer Transgenic Model," American Journal of Pathology, 2004, vol. 165 (4), pp. 1289-1300.

Chancel, "Natixis Conference on Diabetes." Sanofi, Paris, pp. 1-23 (Nov. 8, 2011).

Charles M.A., et al., "Prevention of Type 2 Diabetes: Role of Metformin," Drugs, 1999, vol. 58 (Suppl 1), pp. 71-73.

Chatterjee S., et al., "Insulin Glargine and its Place in the Treatment of Types 1 and 2 Diabetes Mellitus," Expert Opinion on Pharmacotherapy, 2006, vol. 7 (10), pp. 1357-1371.

Cheung Y.T., et al., "Effects of All-Trans-Retinoic Acid on Human SH-SY5Y Neuroblastoma as in Vitro Model in Neurotoxicity Research," Neurotoxicology, 2009, vol. 30 (1), pp. 127-135.

Childs B.P., et al., "Defining and Reporting Hypoglycemia in Diabetes: A Report from the American Diabetes Association Workgroup on Hypoglycemia," Diabetes Care, 2005, vol. 28 (5), pp. 1245-1249.

Cholangiocarcinoma, Johns Hopkins Medicine Webstite, https://gi.jhsps.org/GDLDisease.aspx?CurrentUDV=31&GDLCat_ID=AF793A59-B736-42CB-9E1FE79D2B9FC358&GDL_Disease_ID=A6D1OE80-887D-49A7-B3BB-0517D38CE757, accessed on May 14, 2014, pp. 1-12.

Christensen M., et al., "Lixisenatide, a Novel GLP-1 Receptor Agonist for the Treatment of Type 2 Diabetes Mellitus," IDrugs: The Investigational Drugs Journal, 2009, vol. 12 (8), pp. 503-513.

Christensen M., et al., "Lixisenatide for Type 2 Diabetes Mellitus," Expert Opinion on Investigational Drugs, 2011, vol. 20 (4), pp. 549-557.

Cochran E., et al., "The Use of U-500 in Patients with Extreme Insulin Resistance," Diabetes Care, 2005, vol. 28 (5), pp. 1240-1244.

Colclough et al., Abstract "Levels of FPG and HbA1c Control and the Relationship to BMI in T2D Patients Treated with Basal Insulin and OAD Therapy." Abstract 2416-PO; Presented at the 72nd Scientific Session at the American Diabetes Association Meeting, 2012, A609, one page.

Colino E., et al., "Therapy with Insulin Glargine (Lantus) in toddlers, Children and Adolescents with Type 1 Diabetes," Diabetes Research and Clinical Practice, 2005, vol. 70 (1), pp. 1-7.

Correa, "Pautas para el examen de patentes farmaceuticas. Una perspectiva desde la Salud Publica. Documento de Trabajo" Universidad de Buenos Aires, Mar. 2008, see English on pp. 19-20, pp. 1-66.

Craig et al., "ISPAD Clinical Practice Consensus Guidelines 2014 Compendium—Definition, epidemiology, and classification of diabetes in children and adolescents." Pediatric Diabetes, 15(Suppl. 20):4-17 (2014).

Crapo P.A., et al., "Postprandial Plasma-Glucose and -Insulin Responses to Different Complex Carbohydrates," Diabetes, 1977, vol. 26 (12), pp. 1178-1183.

Croom K.F., et al., "Liraglutide a Review of its Use in Type 2 Diabetes Mellitus," Drugs, 2009, vol. 69 (14), pp. 1985-2004.

Cryer P.E., "Hypoglycemia Is the Limiting Factor in the Management of Diabetes," Diabetes/Metabolism Research and Reviews, 1999, vol. 15 (1), pp. 42-46.

Cvetkovic R.S., et al., "Exenatide A Review of its Use in Patients with Type 2 Diabetes Mellitus (As an Adjunct to Metformin and/or A Sulfonylurea)," Drugs, 2007, vol. 67 (6), pp. 935-954.

Czech C., et al., "Proteolytical Processing of Mutated Human Amyloid Precursor Protein in Transgenic Mice," Brain Research Molecular Brain Research, 1997, vol. 47 (1-2), pp. 108-116.

D'Alessio D., "GLP-1 Receptor Agonists: Strategies for PPG Control," Medical Nursing Education, 2011, vol. 3, pp. 1-26.

Database, ADISCTI, "A randomized, 4-sequence, cross-over, double bind, dose response study of 0.4, 0.6 and 0.09 U/kg insluin glarine U300 compared to 0.4 U/kg Lantus U100 in patients with diabetes mellitus type I using euglycemic clamp technique" last updated Dec. 16, 2010, pp. 1-4.

Davis How to Convert mg to mmol/L, available online at http://www.ehow.com/how_8498850_convert mg-mmoll.html (accessed on Nov. 11, 2015).

(56) References Cited

OTHER PUBLICATIONS

De Arriba S.G., et al., "Carbonyl Stress and Nmda Receptor Activation Contribute to Methylglyoxal Neurotoxicity," Free Radical Biology and Medicine, 2006, vol. 40 (5), pp. 779-790.

De La Pena A., et al., "Pharmacokinetics and Pharmacodynamics of High-Dose Human Regular U-500 Insulin Versus Human Regular U-100 Insulin in Healthy Obese Subjects," Diabetes Care, 2011, vol. 34 (12), pp. 2496-2501.

De Rosa R., et al., "Intranasal Administration of Nerve Growth Factor (Ngf) Rescues Recognition Memory Deficits in Ad11 Anti-Ngf Transgenic Mice," Proceedings of the National Academy of Sciences of the United States of America, 2005, vol. 102 (10), pp. 3811-3816.

Definition of indication, Merriam-Webster online, accessed Oct. 22, 2015, 2 pages.

Definition of palliative, http://medicaldictionary.thefreedictionary.com/, accessed on Nov. 6, 2014, pp. 1-2.

Definition of sphincter of pancreatic duct in the Medical Dictionary, http://medicaldictionary.thefreedictionary.com/, accessed on May 22, 2014, pp. 1-2.

Defronzo R.A., et al., "Effects of Exenatide (Exendin-4) on Glycemic Control and Weight Over 30 Weeks in Metformin-Treated Patients with Type 2 Diabetes," Diabetes care, 2005, vol. 28 (5), pp. 1092-1100.

Defronzo R.A., "Pathogenesis of Type 2 Diabetes: Implications for Metformin," Drugs, 1999, vol. 58 (Suppl 1), pp. 29-30.

Defronzo R.A., "Pharmacologic therapy for Type 2 Diabetes Mellitus," Annals of Internal Medicine, 1999, vol. 131 (4), pp. 281-303.

Delatour B., et al., "Alzheimer Pathology Disorganizes Cortico-Cortical Circuitry: Direct Evidence from a Transgenic Animal Model," Neurobiology of Disease, 2004, vol. 16 (1), pp. 41-47.

Devries J.H., et al., "Sequential intensification of Metformin Treatment in Type 2 Diabetes with Liraglutide Followed by Randomized Addition of Basal Insulin Prompted by A1C Targets," Diabetes Care, 2012, vol. 35 (7), pp. 1446-1454.

Dewitt D.E., "Case Study: Treating New on-Set Catabolic Type 2 Diabetes with Glargine and Lispro," Clinical Diabetes, 2006, vol. 24 (4), pp. 180-181.

Diabetes Prevention Program Research Group, "Reduction in the incidence of Type 2 Diabetes with Lifestyle intervention or Metformin," The New England Journal of Medicine, 2002, vol. 346 (6), pp. 393-403.

Distiller et al., Poster: "Pharmacokinetics and Pharmacodynamics of a New GLP-1 Agonist AVE0010 in Type 2 Diabetes Patients" Meeting: 68th Scientific Sessions (Jun. 2008) Poster No. 520-P.

Dixon G.H., et al., "Regeneration of Insulin Activity from the Separated and inactive A and B Chains," Nature, 1960, vol. 188 (4752), pp. 721-724.

Donelli G., et al., "Plastic Biliary Stent Occlusion: Factors Involved and Possible Preventive Approaches," Clinical Medicine & Research, 2007, vol. 5 (1), pp. 53-60.

Dormandy J.A., et al., "Secondary Prevention of Macrovascular Events in Patients with Type 2 Diabetes in the Proactive Study (Prospective Pioglitazone Clinical Trial in Macrovascular Events): A Randomised Controlled Trial," Lancet, 2005, vol. 366 (9493), pp. 1279-1289.

Doyle M.E. et al., "Mechanisms of Action of Glucagon-Like Peptide 1 in the Pancreas," Pharmacology & Therapeutics, 2007, vol. 113 (3), pp. 546-593.

Drucker D.J. et al., "The incretin System: Glucagon-Like Peptide-1 Receptor Agonists and Dipeptidyl Peptidase-4 inhibitors in Type 2 Diabetes," Lancet, 2006, vol. 368 (9548), pp. 1696-1705.

Drury P.L., et al., "Diabetic Nephropathy," British Medical Bulletin, 1989, vol. 45 (1), pp. 127-147.

Dubois B., et al., "Revising the Definition of Alzheimer's Disease: A New Lexicon," Lancet Neurology, 2010, vol. 9 (11), pp. 1118-1127.

Dunn C.J., et al., "Insulin Glargine: An Updated Review of its Use in the Management of Diabetes Mellitus," Drugs, 2003, vol. 63 (16), pp. 1743-1778.

During M.J., et al., "Glucagon-Like Peptide-1 Receptor is involved in Learning and Neuroprotection," Nature Medicine, 2003, vol. 9 (9), pp. 1173-1179.

Eckert A., et al., "Alzheimer's Disease-Like Alterations in Peripheral Cells from Presenilin-1 Transgenic Mice," Neurobiology of Disease, 2001, vol. 8 (2), pp. 331-342.

EFC10780 (Sanofi study), "A randomized, double-blind, double-dummy, 2-arm parallel-group, multicenter 24-week study comparing the efficacy and safety of AVE0010 to sitagliptin as add-on to metformin in obese type 2 diabetic patients younger than 50 and not adequately controlled with metformin (EFC10780)" p. 1-4 (Jan. 29, 2014).

EFC10781 Clinical Trials, "24-week Treatment With Lixisenatide in Type 2 Diabetes Insufficiently Controlled With Metformin and Insulin Glargine" ClinicalTrials.gov; EFC10781 pp. 1-5 (Sep. 2009).

EFC6017; Clinical Trial Eudra CT No. 2007-005884-92, accessed Apr. 24, 2015, one page.

EFC6018; Clinical trial EudraCT 2007-005887-29, "Getgoal-Mono" accessed Jul. 27, 2014; pp. 1-16.

EMA—Science Medicines Health "Toujeo" EPAR Summary for the Public, first published Nov. 5, 2009, pp. 1-3.

EMA Press Release, "European Medicines Agency recommends suspension of Avandia, Avandamet and Avaglim" pp. 1-2 (Sep. 23, 2010).

English translation of Search Report for Chinese Patent Application No. 201280053404.6; dated Feb. 10, 2015, pp. 1-3.

English translation of Search Report for Chinese Patent Application No. 20140220537.9; dated Feb. 13, 2015, pp. 1-2.

English Translation of TIPO Search Report for ROC Patent Application No. 101130936, dated Dec. 1, 2015, one page.

European Medicines Agency—Science Medicines Health, "Guideline on clinical investigation of medicinal products in the treatment of diabetes mellitus" Committee for Medicinal Products for Human Use, Jan. 20, 2010, pp. 1-19.

European Medicines Agency, "Toujeo (previously Optisulin) insulin glargine," &Ithttp: index.jsp?curl="pages/medicines/human/medicines/000309/human_med_000955.jsp&mid=WCOb01ac058001d124">, last updated Jan. 25, 2016, visited Feb. 3, 2016, pp. 1-6—screenshot of "About" tab of webpage and printouts f "About" tab of webpage with listed items collapsed and expanded.</http:>.

Ex Parte Herrmann, Appeal No. 2009-001777 U.S. Appl. No. 10/616,457 (B. Pai. Nov. 13, 2009).

Executive Summary, "Standards of Medical Care in Diabetes-2009" Diabetes Care,32(Suppl. 1):S6-S12 (Jan. 2009).

Extended European Search Report for Euorpean Application No. 98 11 0889.7; dated Oct. 14, 1998, pp. 1-4.

Extended European Search Report for European Application No. 09 17 5876.3; dated Mar. 24, 2010, pp. 1-4.

Extended European Search Report for European Application No. 09 17 5877.1; dated Apr. 29, 2010, pp. 1-5.

Extended European Search Report for European Application No. 10 16 4368.2; dated Oct. 14, 2010, pp. 1-6.

Extended European Search Report for European Application No. 10 30 5780; dated Nov. 16, 2010, pp. 1-3.

Extended European Search Report for European Application No. 11 15 3106; dated Jul. 6, 2011, pp. 1-12.

Extended European Search Report for European Application No. 11 16 0270.2; dated Sep. 19, 2011, pp. 1-8.

Extended European Search Report for European Application No. 11 16 6415; dated Mar. 12, 2012, pp. 1-12.

Extended European Search Report for European Application No. 11 17 9149.7; dated Feb. 9, 2012, pp. 1-8.

Extended European Search Report for European Application No. 13 305 432.0; dated Sep. 13, 2013, pp. 1-5.

Extended European Search Report for European Application No. 14 16 6877.2; of Aug. 18, 2014, pp. 1-6.

Extended European Search Report for European Application No. 14 19 7154.9: dated Apr. 8, 2015, pp. 1-7.

Fabunmi R., et al., "Patient Characteristics, Drug Adherence Patterns, and Hypoglycemia Costs for Patients with Type 2 Diabetes

(56) References Cited

OTHER PUBLICATIONS

Mellitus Newly initiated on Exenatide or Insulin Glargine," Current Medical Research and Opinion, 2009, vol. 25 (3), pp. 777-786.
Faivre E., et al., "Effects of Gip Analogues in Neuronal Signalling, Cell Proliferation and Learning and Memory," Regulatory Peptides, 2010, vol. 164 (1), pp. 40-41.
FDA Frequently Asked Questions about Combination Products;accessed from www.fda.gov/CombinationProducts/AboutCombinationProducts/usm101496.1/htm, 2009 downloaded Jul. 13, 2012, pp. 1-18.
FDA Guidance for Industry, US Department of Health and Human Services, Food and Drug Administration, Center for Drug Evaluation and Research (COER), pp. 1-11, Feb. 2014.
Feinglos M.N., et al., "Effects of Liraglutide (Nn2211), A Long-Acting GLP-1 Analogue, on Glycaemic Control and Bodyweight in Subjects with Type 2 Diabetes," Diabetic Medicine, 2005, vol. 22 (8), pp. 1016-1023.
Fieller E.C., "Symposium on Interval Estimation; Some Problems with Interval Estimation," Journal of the Royal Statistical Society, 1954, vol. 16 (2), pp. 175-185.
Final Office Action from U.S. Appl. No. 12/617,805; mailed Feb. 11, 2013, pp. 1-13.
Final Office Action from U.S. Appl. No. 12/617,805; mailed Jan. 12, 2012, pp. 1-14.
Final Office Action from U.S. Appl. No. 12/617,805; mailed Jan. 13, 2015, pp. 1-11.
Final Office Action issued in U.S. Appl. No. 13/123,835; mailed Feb. 12, 2013, pp. 1-13.
Final Office Action issued in U.S. Appl. No. 13/602,913; mailed on Apr. 2, 2015, pp. 1-7.
Final Office Action issued in U.S. Appl. No. 13/602,913; mailed on Jun. 20, 2014, pp. 1-27.
Final Office Action issued in U.S. Appl. No. 13/602,913; mailed on Sep. 13, 2013, pp. 1-11.
Final Office action issued in U.S. Appl. No. 13/382,442; mailed Aug. 11, 2015, pp. 1-35.
Final Rejection in U.S. Appl. No. 13/633,496; mailed Nov. 18, 2014, pp. 1-11.
Final Rejection in U.S. Appl. No. 13/633,496; mailed Nov. 4, 2013, pp. 1-7.
Final Rejection in U.S. Appl. No. 13/633,563; mailed Apr. 22, 2015, pp. 1-12.
Final Rejection in U.S. Appl. No. 13/633,563; mailed Dec. 16, 2013, pp. 1-58.
Final Rejection issued in U.S. Appl. No. 12/617,811; mailed Jan. 4, 2013, pp. 1-6.
Final Rejection issued in U.S. Appl. No. 12/617,811; mailed Jul. 31, 2015, pp. 1-15.
Final Rejection issued in U.S. Appl. No. 13/110,568; mailed Feb. 21, 2013, pp. 1-20.
Final Rejection issued in U.S. Appl. No. 13/310,118; mailed Aug. 2, 2012, pp. 1-20.
Final Rejection issued in U.S. Appl. No. 13/363,956; mailed May 20, 2014, pp. 1-16.
Final Rejection issued in U.S. Appl. No. 13/467,707; mailed Feb. 12, 2016, pp. 1-12.
Final Rejection issued in U.S. Appl. No. 13/467,707; mailed Feb. 25, 2014, pp. 1-18.
Final Rejection issued in U.S. Appl. No. 13/467,707; mailed Jan. 7, 2015, pp. 1-8.
Final Rejection issued in U.S. Appl. No. 13/468,422; mailed Jan. 6, 2014, pp. 1-21.
Final Rejection issued in U.S. Appl. No. 13/468,422; mailed Jan. 23, 2015, pp. 1-27.
Final Rejection issued in U.S. Appl. No. 13/469,633; mailed Dec. 4, 2013, pp. 1-17.
Final Rejection issued in U.S. Appl. No. 13/469,633; mailed Jan. 23, 2015, pp. 1-12.
Final Rejection issued in U.S. Appl. No. 13/595,590; mailed Apr. 2, 2014, pp. 1-7.
Final Rejection issued in U.S. Appl. No. 13/595,590; mailed Dec. 19, 2014, pp. 1-14.
Final Rejection issued in U.S. Appl. No. 13/661,476, mailed on Oct. 2, 2014, pp. 1-33.
Final Rejection issued in U.S. Appl. No. 13/692,640; mailed Jan. 6, 2015, pp. 1-11.
Final Rejection issued in U.S. Appl. No. 13/692,640; mailed Jun. 2, 2015, pp. 1-12.
Final Rejection issued in U.S. Appl. No. 13/700,631; mailed Apr. 13, 2015, pp. 1-19.
Final Rejection issued in U.S. Appl. No. 13/700,631; mailed Jun. 18, 2014, pp. 1-25.
Final Rejection issued in U.S. Appl. No. 13/819,114; mailed Mar. 2, 2015, pp. 1-10.
Final-Rejection issued in U.S. Appl. No. 13/432,811; mailed Dec. 12, 2014, pp. 1-8.
Final-Rejection issued in U.S. Appl. No. 13/432,811; mailed Mar. 31, 2015, pp. 1-9.
Final-Rejection issued in U.S. Appl. No. 13/432,811; mailed Sep. 6, 2014, pp. 1-8.
Final Rejection issued in U.S. Appl. No. 13/509,542, mailed Feb. 10, 2016, pp. 1-40.
Final-Rejection issued in U.S. Appl. No. 13/432,811; mailed Feb. 10, 2016, pp. 1-9.
Fonseca V.A., et al., "Efficacy and Safety of the once-Daily GLP-1 Receptor Agonist Lixisenatide in Monotherapy: A Randomized, Double-Blind, Placebo-Controlled Trial in Patients with Type 2 Diabetes (Getgoal-Mono)," Diabetes Care, 2012, vol. 35 (6), pp. 1225-1231.
Fox J.D., et al., "Single Amino Acid Substitutions on the Surface of Escherichia Coli Maltose-Binding Protein can have a Profound Impact on the Solubility of Fusion Proteins," Protein Science, 2001, vol. 10 (3), pp. 622-630.
Fransson J., et al., "Oxidation of Human Insulin-Like Growth Factor I in formulation Studies: Kinetics of Methionine Oxidation in Aqueous Solution and in Solid State," Pharmaceutical Research, 1996, vol. 13 (8), pp. 1252-1257.
Gallwitz B., "Liraglutide. GLP-1 Receptor Agonist Treatment of Type 2 Diabetes Treatment of Obesity," Drugs of the Future, 2008, vol. 33 (1), pp. 13-20.
Gandhi S., et al., "Molecular Pathogenesis of Parkinson's Disease," Human Molecular Genetics, 2005, vol. 14 (18), pp. 2749-2755.
Garber a., et al., "Liraglutide Versus Glimepiride Monotherapy for Type 2 Diabetes (Lead-3 Mono): A Randomised, 52-Week, Phase III, Double-Blind, Parallel-Treatment Trial," The Lancet, 2009, vol. 373 (9662), pp. 473-481.
Garg R., et al., "U-500 Insulin: Why, When and How to Use in Clinical Practice," Diabetes/Metabolism Research and Reviews, 2007, vol. 23 (4), pp. 265-268.
Garriques L.N., et al., "The Effect of Mutations on the Structure of Insulin Fibrils Studied by Fourier Transform infrared (FTIR) Spectroscopy and Electron Microscopy," Journal of Pharmaceutical Sciences, 2002, vol. 91 (12), pp. 2473-2480.
Gault V.A., et al., "GLP-1 Agonists Facilitate Hippocampal Ltp and Reverse the Impairment of LTP induced by Beta-Amyloid," European Journal of Pharmacology, 2008, vol. 587 (1-3), pp. 112-117.
Gavin J.R., "Report of the Expert Committee on the Diagnosis and Classification of Diabetes Mellitus," Diabetes Care, 1997, vol. 20 (7), pp. 1183-1197.
Geiger R., "The Chemistry of Insulin," Chemiker Zeitung, 1976, vol. 100 (3), pp. 54-56.
Gengler S., et al., "Val(8)GLP-1 Rescues Synaptic Plasticity and Reduces Dense Core Plaques in APP/PS1 Mice," Neurobiology of Aging, 2012, vol. 33 (2), pp. 265-276.
Gerich et al., "Monotherapy with GLP-1 receptor agonist, Lixisenatide, significantly improves glycaemic control in type 2 diabetic patients," Diabetologia 53(Supplement 1)p. S330, Abstract 830, Presented at 46th Annual Meeting of EASD, Stockholm, Sweden, p. 1 (Sep. 2010).
Giugliano D., et al., "Treatment Regimens with Insulin Analogues and Haemoglobin A1C Target of <7% in Type 2 Diabetes: A Systematic Review," Diabetes Research and Clinical Practice, 2010, vol. 92 (1), pp. 1-10.

(56) References Cited

OTHER PUBLICATIONS

Goldstein D.E., et al., "Tests of Glycemia in Diabetes," Diabetes Care, 1995, vol. 18 (6), pp. 896-909.
Gough K., et al., "Assessment of Dose Proportionality: Report from the Statisticians in the Pharmaceutical Industry/Pharmacokinetics UK Joint Working Party," Drug Information Journal, 1995, vol. 29, pp. 1039-1048.
Goykhman S., et al., "Insulin Glargine: A Review 8 Years After its introduction," Expert Opinion on Pharmacotherapy, 2009, vol. 10 (4), pp. 705-718.
Gura T., "Systems for Identifying New Drugs Are often Faulty," Science, 1997, vol. 278 (5340), pp. 1041-1042.
Gygi S.P., et al, "Quantitative Analysis of Complex Protein Mixtures Using Isotope-Coded Affinity Tags," Nature Biotechnology, 1999, vol. 17 (10), pp. 994-999.
Hamilton A., et al., "Novel GLP-1 Mimetics Developed to Treat Type 2 Diabetes Promote Progenitor Cell Proliferation in the Brain," Journal of Neuroscience Research, 2011, vol. 89 (4), pp. 481-489.
Hamilton A., et al., "Receptors for the incretin Glucagon-Like Peptide-1 are Expressed on Neurons in the Central Nervous System," NeuroReport, 2009, vol. 20 (13), pp. 1161-1166.
Hanas R., et al., "2010 Consensus Statement on the Worldwide Standardization of the Hemoglobin A1C Measurement," Diabetes Care, 2010, vol. 33 (8), pp. 1903-1904.
Hanefeld M., et al., "The Postprandial State and the Risk of Atherosclerosis," Diabetic Medicine, 1997, vol. 14 (Suppl 3), pp. S6-S11.
Hanefeld M., "Normnahe Postprandiale Hyperglykamie-Eine Essenzielle Komponente Guter Diabeteskontrolle Und Pravention Kardiovaskularer Erkrankungen (Near-Normal Postprandial Hyperglycemia—An Essential Component of Good Diabetes Control and Prevention of Cardiovascular Diseases)," Paul Langerhans Lecture Diabetologie and Stoffwechsel, 2007, vol. 2, pp. 362-369.
Hanna et al., "Canadian Diabetes Association Clinical Practice Guidelines Expert Committee Pharmacologic Management of Type 2 Diabetes," Canadian Journal of Diabetes, 2003, vol. 27 (Supp 2), pp. S37-S42.
Harkavyi A., et al., "Glucagon-Like Peptide I Receptor Stimulation Reverses Key Deficits in Distinct Rodent Models of Parkinson's Disease," Journal of Neuroinflammation, 2008, vol. 5 (19), pp. 1-9.
Harris S.B., et al., "Clinical inertia in Patients with T2Dm Requiring Insulin in Family Practice," Canadian Family Physician, 2010, vol. 56 (12), pp. e418-e424.
Hartmann H., et al., "Biological Activity of Des-(B26-B30)-Insulinamide and Related Analogues in Rat Hepatocyte Cultures," Diabetologia, 1989, vol. 32 (7), pp. 416-420.
Hellstrom M., et al., "T1388 GTP-010 as a Therapetuic tool in IBS Pain Relief: Prospective, Randomized, Palebo-Controlled Study of a GLP-1 Analog," Gastroenterology, 2008, vol. 134 (4), pp. A-544.
Higgins G.C., et al., "Oxidative Stress: Emerging Mitochondrial and Cellular themes and Variations in Neuronal Injury," Journal of Alzheimer's Disease, 2010, vol. 20, pp. S453-S473.
Himeno T., et al., "Beneficial Effects of Exendin-4 on Experimental Polyneuropathy in Diabetic Mice," Diabetes, 2011, vol. 60 (9), pp. 2397-2406.
Hinds K., et al., "Synthesis and Characterization of Poly(Ethylene Glycol)-Insulin Conjugates," Bioconjugate Chemistry, 2000, vol. 11 (2), pp. 195-201.
Hoe 901/2004 Study Investigators Group, "Safety and Efficacy of Insulin Glargine (Hoe 901) Versus NPH Insulin in Combination with oral Treatment in Type 2 Diabetic Patients," Diabetic Medicine, 2003, vol. 20, pp. 545-551.
Holman R.R., et al., "10-Year Follow-Up of intensive Glucose Control in Type 2 Diabetes," The New England Journal of Medicine, 2008, vol. 359 (15), pp. 1577-1589.
Holscher C., "Development of Beta-Amyloid-induced Neurodegeneration in Alzheimer's Disease and Novel Neuroprotective Strategies," Reviews in the Neurosciences, 2005, vol. 16 (3), pp. 181-212.
Holscher C., et al., "New Roles for Insulin-Like Hormones in Neuronal Signalling and Protection: New Hopes for Novel Treatments of Alzheimer's Disease?," Neurobiology of Aging, 2008, vol. 31 (9), pp. 1495-1502.
Holscher C., "Incretin Analogues that have been Developed to Treat Type 2 Diabetes Hold Promise as a Novel Treatment Strategy for Alzheimer's Disease," Recent Patents on Cns Drug Discovery, 2010, vol. 5 (2), pp. 109-117.
Holscher C., "Possible Causes of Alzheimer's Disease: Amyloid Fragments, Free Radical, and Calcium Homeostasis," Neurobiology of Disease, 1998, vol. 5 (3), pp. 129-141.
Holscher C., "The Role of GLP-1 in Neuronal Activity and Neurodegeneration," Vitamins and Hormones, 2010, vol. 84, pp. 331-354.
Holst J.J., et al., "Combining GLP-1 Receptor Agonists with Insulin: therapeutic Rationales and Clinical Findings," Diabetes, Obesity and Metabolism, 2013, vol. 15 (1), pp. 3-14.
Home P.D., et al., "Insulin Treatment: A Decade of Change," British Medical Bulletin, 1989, vol. 45 (1), pp. 92-110.
http://diabetes.emedtv.com/lantus/generic-lantus.html; one page, last accessed Dec. 23, 2015.
Hunter K., et al., "Drugs Developed to Treat Diabetes, Liraglutide and Lixisenatide, Cross the Blood Brain Barrier and Enhance Neurogenesis," BMC Neuroscience, 2012, vol. 13, pp. 1-6.
Inpharma, Product News. "AVE0010 set to deliver in type 2 diabetes mellitus," Database Adisnews, retrieved from STN, Jun. 2008, pp. 1-3.
International Search Report by the ISA for International Application No. PCT/EP2007/005932; dated Oct. 9, 2007, pp. 1-6.
International Search Report by the ISA for International Application No. PCT/EP2009/000017; dated Jun. 22, 2009, pp. 1-7.
International Search Report by the ISA for International Application No. PCT/EP2009/063195; dated May 6, 2010.
International Search Report by the ISA for International Application No. PCT/EP2010/059436; dated Jun. 17, 2011, pp. 1-5.
International Search Report by the ISA for International Application No. PCT/EP2010/059438; dated Oct. 4, 2010, pp. 1-3.
International Search Report by the ISA for International Application No. PCT/EP2010/062638; dated Mar. 18, 2011, pp. 1-5.
International Search Report by the ISA for International Application No. PCT/EP2010/067250; dated Mar. 23, 2011, pp. 1-3.
International Search Report by the ISA for International Application No. PCT/EP2011/058079; dated Mar. 22, 2012, pp. 1-6.
International Search Report by the ISA for International Application No. PCT/EP2011/058764; dated Jun. 30, 2011, pp. 1-9.
International Search Report by the ISA for International Application No. PCT/EP2012/051670; dated Mar. 26, 2012, pp. 1-16.
International Search Report by the ISA for International Application No. PCT/EP2012/055660; dated May 10, 2012, pp. 1-6.
International Search Report by the ISA for International Application No. PCT/EP2012/058745; dated Jul. 12, 2012, pp. 1-6.
International Search Report by the ISA for International Application No. PCT/EP2012/058747; dated Jul. 8, 2012, pp. 1-6.
International Search Report by the ISA for International Application No. PCT/EP2012/058749; dated Jul. 31, 2012, pp. 1-6.
International Search Report by the ISA for International Application No. PCT/EP2012/058779; dated Aug. 28, 2012, pp. 1-5.
International Search Report by the ISA for International Application No. PCT/EP2012/066617; dated Nov. 22, 2012, pp. 1-5.
International Search Report by the ISA for International Application No. PCT/EP2012/067144; dated Aug. 11, 2012, pp. 1-5.
International Search Report by the ISA for International Application No. PCT/EP2012/069483; dated Nov. 29, 2011, pp. 1-4.
International Search Report by the ISA for International Application No. PCT/EP2012/069485; dated Dec. 11, 2012, pp. 1-5.
International Search Report by the ISA for International Application No. PCT/EP2012/071271; dated Jan. 30, 2013, pp. 1-5.
International Search Report by the ISA for International Application No. PCT/EP2012/074150; dated Nov. 20, 2012, pp. 1-4.
International Search Report by the ISA for International Application No. PCT/EP2014/056498; dated Jun. 25, 2014, pp. 1-10.
International Search Report by the ISA for International Application No. PCT/EP2014/062418; dated Sep. 22, 2014, pp. 1-4.

(56) References Cited

OTHER PUBLICATIONS

Inzucchi S.E., et al., "Management of Hyperglycemia in Type 2 Diabetes: A Patient-Centered Approach," Diabetes Care, 2012, vol. 35, pp. 1364-1379.
Isacson R., et al., "The Glucagon-Like Peptide 1 Receptor Agonist Exendin-4 improves Reference Memory Performance and Decreases Immobility in the forced Swim Test," European Journal of Pharmacology, 2009, vol. 650 (1), pp. 249-255.
ISPAD, International Diabetes Federation; "Global/IDF/ISPAD Guideline for Diabetes in Childhood and Adolescence," pp. 1-132 (2011).
Jain R.K., "Barriers to Drug Delivery in Solid Tumors," Scientific American, 1994, vol. 271 (1), pp. 58-65.
Jang J.H., et al., "Neuroprotective Effects of Triticum Aestivum L. Against B-Amyloid-induced Cell Death and Memory Impairments," Phytotherapy Research, 2010, vol. 24 (1), pp. 76-84.
Jekel P.A., et al., "Use of Endoproteinase Lys-C from Lysobacter Enzymogenes in Protein Sequence Analysis," Analytical Biochemistry, 1983, vol. 134 (2), pp. 347-354.
Jendle J., et al., "Insulin and GLP-1 Analog Combinations in Type 2 Diabetes Mellitus: A Critical Review," Expert Opinion on Investigational Drugs, 2012, vol. 21 (10), pp. 1463-1474.
Jimenez S., et al., "Inflammatory Response in the Hippocampus of PS1M146L/App751SL Mouse Model of Alzheimer'S Disease: Age-Dependent Switch in the Microglial Phenotype from Alternative to Classic," The Journal of Neuroscience, 2008, vol. 28 (45), pp. 11650-11661.
Johnson et al., "When is a unit of insulin not a unit of insulin? Detemir dosing in type 2 diabetes" Poster, one page, 2008. http://professional.diabetes.org/ContenUPosters/2008/p8-Lb.pdf.
Jorgensen K.H., et al., "Five Fold Increase of Insulin Concentration Delays the Absorption of Subcutaneously Injected Human Insulin Suspensions in Pigs," Diabetes Research and Clinical Practice, 2000, vol. 50, pp. 161-167.
Kaarsholm N. C., et al., "Engineering Stability of the Insulin Monomer Fold with Application to Structure-Activity Relationships," Biochemistry, 1993, vol. 32 (40), pp. 10773-10778.
Kadima W., "Role of Metal Ions in the T- to R-Allosteric Transition in the Insulin Hexamer," Biochemistry, 1999, vol. 38 (41), pp. 13443-13452.
Kaduszkiewicz H., et al., "Cholinesterase inhibitors for Patients with Alzheimer's Disease: Systematic Review of Randomised Clinical Trials," British Medical Journal (Clinical Research ed.), 2005, vol. 331 (7512), pp. 321-327.
Kaech S., et al., "Culturing Hippocampal Neurons," Nature Protocols, 2006, vol. 1 (5), pp. 2406-2415.
Kahn S.E., et al., "Glycemic Durability of Rosiglitazone, Metformin, or Glyburide Monotherapy," The New England Journal of Medicine, 2006, vol. 355 (23), pp. 2427-2443.
Kakhki V.R.D., et al., "Normal Values of Gallbladder Ejection Fraction Using 99m Tc-Sestamibi Scintigraphy after a Fatty Meal formula," Journal of Gastrointestinal and Liver Diseases, 2007, vol. 16 (2), pp. 157-161.
Kamisawa T., et al., "Pancreatographic investigation of Pancreatic Duct System and Pancreaticobiliary Malformation," Journal of Anatomy, 2008, vol. 212 (2), pp. 125-134.
Kanazawa M., et al., "Criteria and Classification of Obesity in Japan and Asia-Oceania," Asia Pacific Journal of Clinical Nutrition, 2002, vol. 11 (Suppl 7), pp. S732-S737.
Kang S., et al., "Subcutaneous Insulin Absorption Explained by Insulin'S Physicochemical Properties Evidence from Absorption Studies of Soluble Human Insulin and Insulin Analogues in Humans," Diabetes Care, 1991, vol. 14 (11), pp. 942-948.
Kao C.H., et al., "The Evaluation of Gallbladder Function by Quantitative Radionuclide Cholescintigraphy in Patients with Noninsulin-Dependent Diabetes Mellitus," Nuclear Medicine Communications, 1993, vol. 14 (10), pp. 868-872.
Kapitza et al., Abstract "Pharmacodynamic Characteristics of Lixisenatide QD vs Liraglutide QD in Patients with T2DM Inadequately Controlled with Metformin" Abtract D-0740, presented at the World Diabetes Congress in Dubai, Dec. 5-8, 2011, one page.
Kastin A.J., et al., "Entry of Exedin-4 into Brain Is Rapid but may be Limited at High Doses International Journal of Obesity and Related Metabolic Disorders," Journal of the International Association for the Study of Obesity, 2003, vol. 27 (3), pp. 313-318.
Kastin A.J., et al., "Interactions of Glucagon-Like Peptide-1 (GLP-1) with the Blood-Brain Barrier," Journal of Molecular Neuroscience, 2001, vol. 18 (1-2), pp. 7-14.
Kemmler W., et al., "Studies on the Conversion of Prolnsulin to Insulin," The Journal of Biological Chemistry, 1971, vol. 246 (22), pp. 6786-6791.
Kendall D.M., et al., "Effects of Exenatide (Exendin-4) on Glycemic Control Over 30 Weeks in Patients with Type 2 Diabetes Treated with Metformin and a Sulfonylurea," Diabetes care, 2005, vol. 28 (5), pp. 1083-1091.
Kielgast U., et al., "Treatment of Type 1 Diabetic Patients with Glucagon-Like Peptide-1 (GLP-1) and GLP-1R Agonists," Current Diabetes Reviews, 2009, vol. 5 (4), pp. 266-275.
Kim S., et al., "Exendin-4 Protects Dopaminergic Neurons by Inhibition of Microglial Activation and Matrix Metalloproteinase-3 Expression in an Animal Model of Parkinson's Disease," Journal of Endocrinology, 2009, vol. 202 (3), pp. 431-439.
Knee T.S., et al., "A Novel Use of U-500 Insulin for Continuous Subcutaneous Insulin infusion in Patients with Insulin Resistance: A Case Series," Endocrine Practice, 2003, vol. 9 (3), pp. 181-186.
Kohn W.D., et al., "Pi-Shifted Insulin Analogs with Extended in Vivo Time Action and Favorable Receptor Selectivity," Peptides, 2007, vol. 28 (4), pp. 935-948.
Kohner E.M., "Diabetic Retinopathy," British Medical Bulletin, 1989, vol. 45 (1), pp. 148-173.
Korczyn A.D., et al, "Emerging therapies in the Pharmacological Treatment of Parkinson's Disease," Drugs, 2002, vol. 62 (5), pp. 775-786.
Krishnamurthy G.T., et al., "Constancy and Variability of Gallbladder Ejection Fraction: Impact on Diagnosis and therapy," Journal of Nuclear Medicine, 2004, vol. 45 (11), pp. 1872-1877.
Lando, "The New 'Designer' Insulins", Clinical Diabetes, 18(4): Fall 2000 (http://journal.diabetes.org/clinical diabelesN18N42000/pg154.hlm; accessed Oct. 22, 2013, pp. 1-13).
Langston J.W., et al., "Chronic Parkinsonism in Humans due to a Product of Meperedine-Analog Synthesis," Science, 1983, vol. 219 (4587), pp. 979-980.
Langui D., et al., "Subcellular Topography of Neuronal Aβ Peptide in APPxPS1 Transgenic Mice," The American Journal of Pathology, 2004, vol. 165 (5), pp. 1465-1477.
Lantus® Annex I—Summary of product characteristics. Date of first authorisation: Jun. 9, 2000, pp. 1-164.
Lantus® Product Information—European Medicines Agency, first published Aug. 5, 2009, pp. 1-2.
Larsen P.J., et al., "Combination of the Insulin Sensitizer, Pioglitazone, and the Long-Acting GLP-1 Human Analog, Liraglutide, Exerts Potent Synergistic Glucose-Lowering Efficacy in Severely Diabetic ZDF Rats," Diabetes, Obesity and Metabolism, 2008, vol. 10, pp. 301-311.
Laursen K., et al., "Enhanced Monitoring of Biopharmaceutical Product Purity Using Liquid Chromatography-Mass Spectrometry," Journal of Chromatography A, 2011, vol. 1218 (28), pp. 4340-4348.
Lee C.H., et al., "Ischemia-Induced Changes in Glucagon-Like Peptide-1 Receptor and Neuroprotective Effect of its Agonist, Exendin-4, in Experimental Transient Cerebral lschemia," Journal of Neuroscience Research, 2011, vol. 89 (7), pp. 1103-1113.
Leib R.D., et al., "Direct Quantitation of Peptide Mixtures without Standards Using Clusters formed by Electrospray Ionization Mass Spectrometry," Analytical Chemistry, 2009, vol. 81 (10), pp. 3965-3972.
Levin P., et al., "Combination therapy with Insulin Glargine and Exenatide: Real-World Outcomes in Patients with Type 2 Diabetes," Current Medical Research and Opinion, 2012, vol. 28 (3), pp. 439-446.
Levine R.L., et al., "Oxidation of Methionine in Proteins: Roles in Antioxidant Defense and Cellular Regulation," IUBMB life, 2000, vol. 50 (4-5), pp. 301-307.

(56) References Cited

OTHER PUBLICATIONS

Leyer S., et al., "The Role of the C-Terminus of the Insulin B-Chain in Modulating Structural and Functional Properties of the Hormone," International Journal of Peptide and Protein Research, 1995, vol. 46 (5), pp. 397-407.

Li H., et al., "Chronic Treatment of Exendin-4 Affects Cell Proliferation and Neuroblast Differentiation in the Adult Mouse Hippocampal Dentate Gyrus," Neuroscience letters, 2010, vol. 19, pp. 1205-1219.

Li L., et al., "Common Pathological Processes in Alzheimer Disease and Type 2 Diabetes: A Review," Brain Research Reviews, 2007, vol. 56, pp. 384-402.

Li Y., et al., "Enhancing the GLP-1 Receptor Signaling Pathway Leads to Proliferation and Neuroprotection in Human Neuroblastoma Cells," Journal of Neurochemistry, 2010, vol. 113 (6), pp. 1621-1631.

Li Y., et al., "GLP-1 Receptor Stimulation Preserves Primary Cortical and Dopaminergic Neurons in Cellular and Rodent Models of Stroke and Parkinsonism," Proceedings of the National Academy of Sciences of the United States of America, 2009, vol. 106 (4), pp. 1285-1290.

Li Y., et al., "GLP-1 Receptor Stimulation Reduces Amyloid-Beta Peptide Accumulation and Cytotoxicity in Cellular and Animal Models of Alzheimer's Disease," Journal of Alzheimer's Disease, 2010, vol. 19 (4), pp. 1205-1219.

Liu & Ruus, Abstract "Pharmacokinetics and Safety of the GLP-1 Agonist AVE0010 in Patients with Renal Impairment," Diabetes 58 (Suppl. 1): Abstract 557-P for the 69th Scientific Session of the American Diabetes Association Jun. 5-9, 2009, New Orleans, Louisiana, pp. 1-2.

Lixisenatide, Chemical Structure CID 16139342, Pubchem, accessed Feb. 5, 2015 at URL pubchem.ncbi.nlm.nih.gov/summary/summary.cgi?sid=135267128&viewopt=Deposited, pp. 1-3.

Insulinpraparat Wikipedia, http://de.wikipedia.org/wiki/Insulinpr%C3%A4parat, pp. 1-15 (Feb. 5, 2013).

Lotharius J., et al., "Effect of Mutant Alpha-Synuclein on Dopamine Homeostasis in a New Human Mesencephalic Cell Line," The Journal of Biological Chemistry, 2002, vol. 277 (41), pp. 38884-38894.

Lotharius J., et al., "Progressive Degeneration of Human Mesencephalic Neuron-Derived Cells Triggered by Dopamine-Dependent Oxidative Stress is Dependent on the Mixed-Lineage Kinase Pathway," Journal of Neuroscience, 2005, vol. 25 (27), pp. 6329-6342.

Lougheed W.D., et al., "Physical Stability of Insulin Formulations," Diabetes, 1983, vol. 32 (5), pp. 424-432.

Lyxumia 10 micrograms solution for injection, Summary of Product Characteristics, updated Oct. 31, 2014, pp. 1-12.

Lyxumia® Annex I—Summary of product characteristics. Date of first authorisation: Feb. 1, 2013, pp. 1-92.

Lyxumia, Chemical Subgroup A10BX, Community Register of Medicinal Products for Human Use, Eurpean Commission Public Health, p. 1-2 (May 2, 2013).

Lyxumia® Product Information—European Medicines Agency, first published Mar. 14, 2013, pp. 1-2.

Mancuso M., et al., "Clinical Features and Pathogenesis of Alzheimer's Disease: involvement of Mitochondria and Mitochondrial DNA," Advances in Experimental Medicine and Biology, 2010, vol. 685, pp. 34-44.

Marbury T.C., et al., "A Pilot Study to Examine the Feasibility of Insulin Glargine in Subjects with Impaired Fasting Glucose, Impaired Glucose tolerance or New-onset Type 2 Diabetes," Experimental and Clinical Endocrinology & Diabetes, 2008, vol. 116 (5), pp. 282-288.

Margolis R.L., et al., "Diagnosis of Huntington Disease," Clinical Chemistry, 2003, vol. 49 (10), pp. 1726-1732.

Markussen J., et al., "Soluble, Prolonged-Acting Insulin Derivatives. I. Degree of Protraction and Crystallizability of Insulins Substituted in the Termini of the B-Chain," Protein Engineering, 1987, vol. 1 (3), pp. 205-213.

Markussen J., et al., "Soluble, Prolonged-Acting Insulin Derivatives II Degree of Protraction and Crystallizability of Insulins Substituted in Positions A17, B8, B13, B27 and B30," Protein Engineering, 1987, vol. 1 (3), pp. 215-223.

Markussen J., et al., "Soluble, Prolonged-Acting Insulin Derivatives. III. Degree of Protraction, Crystallizability and Chemical Stability of Insulins Substituted in Positions A21, B13, B23, B27 and B30," Protein Engineering, 1988, vol. 2 (2), pp. 157-166.

Martin B., et al., "Exendin-4 Improves Glycemic Control, Ameliorates Brain and Pancreatic Pathologies, and Extends Survival in a Mouse Model of Huntington's Disease," Diabetes, 2009, vol. 58 (2), pp. 318-328.

Martin L.J., et al., "Neurodegeneration in Excitotoxicity, Global Cerebral Ischemia, and Target Deprivation: A Perspective on the Contributions of Apoptosis and Necrosis," Brain Research Bulletin, 1998, vol. 46 (4), pp. 281-309.

Mattson M.P., "Calcium and Neurodegeneration," Aging Cell, 2007, vol. 6 (3), pp. 337-350.

McClean P.L., et al., "Glucagon-Like Peptide-1 Analogues Enhance Synaptic Plasticity in the Brain: A Link between Diabetes and Alzheimer's Disease," European Journal of Pharmacology, 2010, vol. 630 (1-3), pp. 158-162.

Mcclean P.L., et al., "The Diabetes Drug Liraglutide Prevents Degenerative Processes in a Mouse Model of Alzheimer's Disease," The Journal of Neuroscience, 2011, vol. 31 (17), pp. 6587-6594.

Medline Plus, "Obesity" available at http://www.nlm.nih.gov/medlineplus/obesity.html, Retrieved Aug. 22, 2013, one page.

Meier J.J., "GLP-1 Receptor Agonists for individualized Treatment of Type 2 Diabetes Mellitus," Nature Reviews. Endocrinology, 2012, vol. 8 (12), pp. 728-742.

Mikhail N.E., "Is Liraglutide a Useful Addition to Diabetes therapy?," Endocrine Practice, 2010, vol. 16 (6), pp. 1028-1037.

Monnier L., et al., "The Loss of Postprandial Glycemic Control Precedes Stepwise Deterioration of Fasting with Worsening Diabetes," Diabetes Care, 2007, vol. 30 (2), pp. 263-269.

Moreno-Gonzalez I., et al., "Extracellular Amyloid-B and Cytotoxic Glial Activation Induce Significant Entorhinal Neuron Loss in Young PS1M146L/APP751SL Mice," Journal of Alzheimer's Disease, 2009, vol. 18, pp. 755-776.

Moretto T.J., et al., "Efficacy and tolerability of Exenatide Monotherapy Over 24 Weeks in Antidiabetic Drug-Naive Patients with Type 2 Diabetes: A Randomized, Double-Blind, Placebo-Controlled, Parallel-Group Study," Clinical Therapeutics, 2008, vol. 30 (8), pp. 1448-1460.

Muller G., et al., "Insulin Signaling in the Yeast Saccharomyces Cerevisiae. 1. Stimulation of Glucose Metabolism and Snf 1 Kinase by Human Insulin," Biochemistry, 1998, vol. 37 (24), pp. 8683-8695.

Nakagawa A., et al., "Receptor Gene Expression of Glucagon-Like Peptide-1, but not Glucose-Dependent Insulinotropic Polypeptide, in Rat Nodose Ganglion Cells," Autonomic Neuroscience, 2004, vol. 110, pp. 36-43.

Nathan D.M., et al., "Management of Hyperglycaemia in Type 2 Diabetes Mellitus: A Consensus Algorithm for the initiation and Adjustment of therapy. Update Regarding the Thiazolidinediones," Diabetologia, 2008, vol. 51 (1), pp. 8-11.

Nauck M.A., et al., "Comparative Evaluation of Incretin-Based Antidiabetic Medications and Alternative therapies to be Added to Melformin in the Case of Monotherapy Failure," Journal of Diabetes Investigation, 2010, vol. 1 (1-2), pp. 24-36.

NCT00299871, ClinicalTrials.gov, "Dose Ranging Study of the GLP-1 Agonist AVE0010 in Metformin-Treated Subjects With Type 2 Diabetes Mellitus," Jun. 22, 2010, Retrieved Nov. 7, 2011, pp. 1-5.

NCT00688701 Clinical Trials.gov "GLP-1 Receptor Agonist Lixisenatide in Patients with Type 2 Diabetes for Glycemic Control and Safety Evaluation in Monotherapy (Getgoal-Mono)" accessed Jul. 27, 2014; pp. 1-5.

NCT00712673, Clinical Trials.gov, "GLP-A Agonist AVE0010 (Morning or Evening) in Patients with Type 2 Diabetes for Glycemic Control and Safety Evaluation, on Top of Metformin", Mar. 22, 2011, pp. 1-4.

NCT00715624 Clinical Trials.gov "GLP-1 Receptor Agonist Lixisenatide in Patients With Type 2 Diabetes for Glycemic Control

(56) References Cited

OTHER PUBLICATIONS and Safety Evaluation, on Top of Basal Insulin (Getgoal-L)" (2008-2014), p. 1-6 (Feb. 2011). D6 version.

NCT00763815, ClinicalTrials.gov, U.S. National Institutes of Health: "GLP-1 Agonist AVE0010 in Patients With Type 2 Diabetes for Glycemic Control and Safety Evaluation on Top of Pioglitazone (Getgoal-P)" pp. 1-8 (Jun. 27, 2011).

NCT00975286, Clinical Trials.gov, "24-week Treatment with Lixisenalide in Type 2 Diabetes Insufficiently Controlled With Melformin and Insulin Glargine", Aug. 8, 2011, pp. 1-4.

NCT00976937, ClinicalTrials.gov, "24-week Study Comparing Lixisenatide (AVE0010) to Sitagliptin as add-on to Metformin in Obese Type 2 Diabetic Patients Younger Than 50," May 6, 2011, Retrieved Nov. 7, 2011, pp. 1-4.

NCT01146678, ClinicalTrials.gov "Relative Bioavailability and Activity of Different Formulations of Insulin Glargine and Lixisenatide in Patients With Diabetes Mellitus Type 1" last updated Sep. 10, 2010, pp. 1-4.

NCT01174810, ClinicalTrials.gov "Exendin-4 as a Treatment for Parkinson's Disease—Pilot Study" accessed Aug. 8, 2011, pp. 1-5.

NCT01195454, NIH Clinical Trials, "Euglycemic clamp dose-response study comparing insulin glargine U300 with Lantus U100" last updated Dec. 13, 2010, pp. 1-4.

NCT01255163, ClinicalTrials.gov "A Clinical Trial of Exendin-4 for the Treatment of Alzheimer's Disease" accessed Aug. 8, 2011, pp. 1-7.

NCT02058147 ClinicalTrials.gov "Efficacy and Safety of Insulin Glargine/Lixisenatide Fixed Ratio Combination Compared to Insulin Glargine Alone and Lixisenatide Alone on Top Metformin in Patients With T2DM (LixLan-O)" first received by ClinicalTrials.gov on Feb. 6, 2014, pp. 1-3.

NCT02058160 ClinicalTrials.gov "Efficacy and Safety of the Insulin Glargine/Lixisenatide Fixed Ratio Combination Versus Insulin Glargine in Patients With Type 2 Diabetes (LixiLan-L)" first received by ClinicalTrials.gov on Feb. 6, 2014, pp. 1-3.

Neidle, "18.2 Failure Modes in the Discovery Process" Cancer Drug Design and Discovery, Elsevier/Academic Press, pp. 427-31 (2008).

Nettleton E.J., et al., "Characterization of the Oligomeric States of Insulin in Self-Assembly and Amyloid Fibril formation by Mass Spectrometry," Biophysical Journal, 2000, vol. 79 (2), pp. 1053-1065.

Nicklas et al., "Inhibition of Nadh-Linked Oxidation in Brain Mitochondria by 1-Methyl-4-Phenyl-Pyridine, A Metabolite of the Neurotoxin, 1-Methyl-4-Phenyl-1,2,5,6-Tetrahydropyridine," Life Sciences, 1985, vol. 36, pp. 2503-2508.

Non-Final Office Action from U.S. Appl. No. 12/617,805; mailed Jul. 24, 2014, pp. 1-12.

Non-Final Office Action from U.S. Appl. No. 12/617,805; mailed May 2, 2012, pp. 1-11.

Non-Final Office Action from U.S. Appl. No. 12/617,805; mailed May 10 2011, pp. 1-12.

Non-Final Office Action from U.S. Appl. No. 12/617,805; mailed Sep. 15, 2015, pp. 1-12.

Non-Final Office Action issued in U.S. Appl. No. 13/123,835; mailed Dec. 22, 2014, pp. 1-13.

Non-Final Office Action issued in U.S. Appl. No. 13/123,835; mailed Jul. 19, 2012, pp. 1-14.

Non-Final Office Action issued in U.S. Appl. No. 13/123,835; mailed May 28, 2015, pp. 1-11.

Non-Final Office Action issued in U.S. Appl. No. 13/602,913; mailed on Dec. 2, 2014, pp. 1-12.

Non-Final Office Action issued in U.S. Appl. No. 13/602,913; mailed on Jan. 13, 2014, pp. 1-53.

Non-Final Office Action issued in U.S. Appl. No. 13/602,913; mailed on May 17, 2013, pp. 1-7.

Non-Final Rejection in U.S. Appl. No. 13/633,496; mailed Apr. 29, 2013, pp. 1-53.

Non-Final Rejection in U.S. Appl. No. 13/633,496; mailed Apr. 6, 2015, pp. 1-14.

Non-Final Rejection in U.S. Appl. No. 13/633,496; mailed May 22, 2014, pp. 1-11.

Non-Final Rejection in U.S. Appl. No. 13/633,563; mailed Dec. 1, 2014, pp. 1-9.

Non-Final Rejection in U.S. Appl. No. 13/633,563; mailed Jul. 1, 2013, pp. 1-56.

Non-Final Rejection in U.S. Appl. No. 13/633,563; mailed Jun. 4, 2014, pp. 1-11.

Non-Final Rejection in U.S. Appl. No. 13/633,563; mailed Oct. 6, 2015, pp. 1-12.

Non-Final Rejection issued in U.S. Appl. No. 12/617,811; mailed Apr. 27, 2011, pp. 1-10.

Non-Final Rejection issued in U.S. Appl. No. 12/617,811; mailed Jan. 14, 2015, pp. 1-15.

Non-Final Rejection issued in U.S. Appl. No. 12/617,811; mailed Jun. 21, 2012, pp. 1-7.

Non-Final Rejection issued in U.S. Appl. No. 12/617,811; mailed Oct. 27, 2011, pp. 1-13.

Non-Final Rejection issued in U.S. Appl. No. 13/110,568; mailed Mar. 19, 2012, pp. 1-18.

Non-Final Rejection issued in U.S. Appl. No. 13/310,118; mailed Mar. 19, 2012, pp. 1-19.

Non-Final Rejection issued in U.S. Appl. No. 13/310,118; mailed Mar. 29, 2013, pp. 1-21.

Non-Final Rejection issued in U.S. Appl. No. 13/310,118; mailed Mar. 25, 2015, pp. 1-15.

Non-Final Rejection issued in U.S. Appl. No. 13/363,956; mailed Apr. 10, 2013, pp. 1-15.

Non-Final Rejection issued in U.S. Appl. No. 13/363,956; mailed Feb. 11, 2015, pp. 1-18.

Non-Final Rejection issued in U.S. Appl. No. 13/363,956; mailed May 29, 2015, pp. 1-17.

Non-Final Rejection issued in U.S. Appl. No. 13/363,956; mailed Nov. 20, 2013, pp. 1-10.

Non-Final Rejection issued in U.S. Appl. No. 13/382,772; mailed Sep. 14, 2015, pp. 1-42.

Non-Final Rejection issued in U.S. Appl. No. 13/467,707; mailed Jul. 15, 2013, pp. 1-20.

Non-Final Rejection issued in U.S. Appl. No. 13/467,707; mailed Jul. 25, 2014, pp. 1-22.

Non-Final Rejection issued in U.S. Appl. No. 13/467,707; mailed Sep. 16, 2015, pp. 1-13.

Non-Final Rejection issued in U.S. Appl. No. 13/468,422; mailed Nov. 4, 2015; pp. 1-27.

Non-Final Rejection issued in U.S. Appl. No. 13/469,633; mailed Aug. 19, 2013, pp. 1-25.

Non-Final Rejection issued in U.S. Appl. No. 13/469,633; mailed Aug. 22, 2014, pp. 1-23.

Non-Final Rejection issued in U.S. Appl. No. 13/469,633; mailed Mar. 27, 2013, pp. 1-39.

Non-Final Rejection issued in U.S. Appl. No. 13/595,590; mailed Jun. 5, 2015, pp. 1-9.

Non-Final Rejection issued in U.S. Appl. No. 13/595,590; mailed Oct. 16, 2013, pp. 1-7.

Non-Final Rejection issued in U.S. Appl. No. 13/595,590; mailed Sep. 5, 2014, pp. 1-10.

Non-Final Rejection issued in U.S. Appl. No. 13/661,476; mailed Jun. 4, 2015, pp. 1-31.

Non-Final Rejection issued in U.S. Appl. No. 13/661,476, mailed on Dec. 4, 2013, pp. 1-11.

Non-Final Rejection issued in U.S. Appl. No. 13/661,476, mailed on Mar. 6, 2014, pp. 1-28.

Non-Final Rejection issued in U.S. Appl. No. 13/661,476, mailed on Sep. 16, 2013, pp. 1-19.

Non-Final Rejection issued in U.S. Appl. No. 13/692,640; mailed May 6, 2014, pp. 1-10.

Non-Final Rejection issued in U.S. Appl. No. 13/692,640; mailed Oct. 31, 2013, pp. 1-10.

Non-Final Rejection issued in U.S. Appl. No. 13/700,631; mailed Apr. 22, 2013, pp. 1-27.

Non-Final Rejection issued in U.S. Appl. No. 13/700,631; mailed Dec. 17, 2015, pp. 1-18.

(56) References Cited

OTHER PUBLICATIONS

Non-Final Rejection issued in U.S. Appl. No. 13/700,631; mailed Nov. 18, 2014, pp. 1-22.
Non-Final Rejection issued in U.S. Appl. No. 13/700,631; mailed Nov. 29, 2013, pp. 1-23.
Non-Final Rejection issued in U.S. Appl. No. 13/819,114; mailed Jul. 31, 2014, pp. 1-9.
Non-Final Rejection issued in U.S. Appl. No. 14/220,562; mailed Apr. 8, 2015, pp. 1-18.
Non-Final Rejection issued in U.S. Appl. No. 14/303,895; mailed May 21, 2015, pp. 1-11.
Non-Final Rejection issued in U.S. Appl. No. 14/303,895; mailed Sep. 9, 2015, pp. 1-12.
Non-Final Rejection issued in U.S. Appl. No. 13/467,757; mailed Apr. 17, 2013, pp. 1-9.
Non-Final Rejection issued in U.S. Appl. No. 13/468,422; mailed Jun. 4, 2014, pp. 1-24.
Non-Final Rejection issued in U.S. Appl. No. 13/468,422; mailed Mar. 27, 2013, pp. 1-27.
Non-Final Rejection issued in U.S. Appl. No. 13/468,422; mailed Sep. 16, 2013, pp. 1-19.
Non-Final-Rejection issued in U.S. Appl. No. 13/432,811; mailed Apr. 8, 2013, pp. 1-7.
Non-Final-Rejection issued in U.S. Appl. No. 13/432,811; mailed Jul. 29, 2014, pp. 1-8.
Non-Final-Rejection issued in U.S. Appl. No. 13/432,811; mailed Sep. 9, 2015, pp. 1-11.
Organization for Economic Co-Ooperation and Development; OECD Principles of Good Laboratory Practice and Compliance Monitoring (as revised in 1997); ENV/MC/CHEM (98)17:1-41 (Jan. 21, 1998).
Ott P., et al., "Diabetes in Germany(Dig) Study a Prospective 4-Year-Follow-Up Study on the Quality of Treatment for Type 2 Diabetes in Daily Practice," Deutsche Medizinische Wochenschrift, 2009, vol. 134 (7), pp. 291-297.
Park C.W., et al., "PPARalpha Agonist Fenofibrate Improves Diabetic Nephropathy in Db/Db Mice," Kidney International, 2006, vol. 69 (9), pp. 1511-1517.
Parkin "Guideline for Management of Postmeal Glucose" International Diabetes Federation, pp. 1-32 (Oct. 2007).
Patel & Advance Collaborative Group, "Effects of a Fixed Combination of Perindopril and indapamide on Macrovascular and Microvascular Outcomes in Patients with Type 2 Diabetes Mellitus (the Advance Trial): A Randomised Controlled Trial," Lancet, 2007, vol. 370 (9590), pp. 829-840.
Perfetti R., "Combining Basal Insulin Analogs with Glucagon-Like Peptide-1 Mimetics," Diabetes Technology & Therapeutics, 2011, vol. 13 (9), pp. 873-881.
Perry T., et al., "A Novel Neurotrophic Property of Glucagon-Like Peptide 1: A Promoter of Nerve Growth Factor-Mediated Differentiation in PC12 Cells," The Journal of Pharmacology and Experimental Therapeutics, 2002, vol. 300 (3), pp. 958-966.
Perry T., et al., "Evidence of GLP-1-Mediated Neuroprotection in an Animal Model of Pyridoxine-induced Peripheral Sensory Neuropathy," Experimental Neurology, 2007, vol. 203 (2), pp. 293-301.
Perry T., et al., "Protection and Reversal of Excitotoxic Neuronal Damage by Glucagon-Like Peptide-1 and Exendin-4," The Journal of Pharmacology and Experimental Therapeutics, 2002, vol. 302 (3), pp. 881-888.
Perry T., et al., "The Glucagon-Like Peptides: A Double-Edged therapeutic Sword?," Trends in Pharmacological Sciences, 2003, vol. 24 (7), pp. 377-383.
Perry T.A., et al., "A New Alzheimer's Disease interventive Strategy: GLP-1," Current Drug Targets, 2004, vol. 5 (6), pp. 565-571.
Pillion D.J., et al., "Dodecylmaltoside-Mediated Nasal and Ocular Absorption of Lyspro-Insulin: Independence of Surfactant from Multimer Dissociation," Pharmaceutical Research, 1998, vol. 15(10), pp. 1637-1639.

Pinget M., et al., "Efficacy and safety of lixisenatide once daily versus placebo in type 2 diabetes insufficiently controlled on pioglitazone (GetGoal-P)," Diabetes, 61(Supp 1):A258, Poster 1010-P (Jun. 2012). One page.
Pi-Sunyer F.X., "The Effects of Pharmacologic Agents for Type 2 Diabetes Mellitus on Body Weight," Postgraduate Medicine, 2008, vol. 120 (2), pp. 5-17.
Porter D.W., et al., "Four Weeks Administration of Liraglutide Improves Memory and Learning As Well As Glycaemic Control in Mice with High Fat Dietary-induced Obesity and Insulin Resistance," Diabetes, Obesity and Metabolism, 2010, vol. 12 (10), pp. 891-899.
Pradier L et al. "Animal Models of Alzheimer's disease." Demences (Dementias); eds. Duyckaerts C. and Pasquier F.; publisher Doin; 165-170 (Sep. 10, 2002; available Aug. 27, 2002).
Prandini N., "Methods of Measuring Gallbladder Motor Functions—the Need for Standardization: Scintigraphy," Digestive and Liver Disease, 2003, vol. 35 (Suppl 3), pp. S62-66.
"Preferable." Merriam-Webster.com. Merriam-Webster, n.d. Web. Sep. 7, 2015. http://www.merriamwebster.com/dictionary/preferable).
Pugeat M., et al., "Insulin Resistance, Polycystic Ovary Syndrome and Metformin," Drugs, 1999, vol. 58 (Suppl 1), pp. 41-46.
Quianzon C.L., et al., "Lixisentide-Once Daily Glucagon-Like Peptide-1 Receptor Agonist in the Management of Type 2 Diabetes," US Endocrinology, 2011, vol. 7 (2), pp. 104-109.
Raccah D., et al., "When Basal Insulin therapy in Type 2 Diabetes Mellitus is not Enough—What Next?," Diabetes/Metabolism Research and Reviews, 2007, vol. 23 (4), pp. 257-264.
Raju R.P., et al., "Optimum Palliation of inoperable Hilar Cholangiocarcinoma: Comparative Assessment of the Efficacy of Plastic and Self-Expanding Metal Stents," Digestive Diseases and Sciences, 2011, vol. 56, pp. 1557-1564.
Ramos B., et al., "Early Neuropathology of Somatostatin/NPY Gabaergic Cells in the Hippocampus of a Ps1xAPP Transgenic Model of Alzheimer's Disease," Neurobiology of Aging, 2006, vol. 27 (11), pp. 1658-1672.
Rao A.D., et al., "Is the Combination of Sulfonylureas and Metformin Associated with an increased Risk of Cardiovascular Disease or all-Cause Mortality? A Meta-Analysis of Observational Studies," Diabetes Care, 2008, vol. 31 (8), pp. 1672-1678.
Ratner R.E., et al., "A Dose-Finding Study of the New GLP-1 Agonist Ave0010 in Type 2 Diabetes Insufficiently Controlled with Melformin," Diabetes, 2008, vol. 57 (Suppl 1), pp. A129.
Ratner R.E., et al., "Dose-Dependent Effects of the Once-Daily GLP-1 Receptor Agonist Lixisenatide in Patients with Type 2 Diabetes Inadequately Controlled with Metformin: A Randomized Double-Blind, Placebo-Controlled Trial," Diabetic Medicine, 2010, vol. 27 (9), pp. 1024-1032.
Ratner R.E., et al., "Post-Meal Pharmacodynamics Profile of Ave0010, a Once-Daily GLP-1 Receptor Agonist, in Patiens with Type 2 Diabetes Inadequately Controlled on Metformin," Diabetologia, 2009, vol. 52 (Suppl 1), pp. S60. Abstract 131.
Ratner R.E., et al., "Abstract # 433-P, A Dose-Finding Study of the New GLP-1 Agonist AVE0010 in Type 2 Diabetes Insufficiently Controlled with Metformin," Diabetes, Poster, 68th Annual Meeting of the American Diabetes Association, San Francisco, Jun. 6-10, 2008, vol. 57 (Suppl 1), p. A129.
Request for "Type C" Meeting letter sent by Michael Lutz addressed to Mary Parks, dated Apr. 21, 2006, pp. 1-10.
Richter, von Margret, "Oldtimer as Newcomer" Pharmazie, pp. 1-9; http://www.pharmazeutische-zeitung.de/pza/2002-12/pharm1.htm (Feb. 2002).
Riddle M., et al., "Contributions of Basal and Postprandial Hyperglycemia over a Wide Range of a 1 C Levels before and after Treatment Intensification in Type 2 Diabetes," Diabetes Care, 2011, vol. 34, pp. 2508-2514.
Riddle M.C., et al., "Adding Once-Daily Lixisenatide for Type 2 Diabetes Inadequately Controlled by Established Basal Insulin: a 24-Week, Randomized, Placebo-Controlled Comparison (Getgoal-L)," Diabetes Care, 2013, vol. 36 (9), pp. 2489-2496.

(56) References Cited

OTHER PUBLICATIONS

Riddle M.C., et al., "Adding once-Daily Lixisenatide for Type 2 Diabetes inadequately Controlled with Newly initiated and Continuously Titrated Basal Insulin Glargine," Diabetes Care, 2013, pp. 2497-2503.
Rohrmann C.A., "Differential Diagnosis of Pancreatic and Biliary Duct Diseases," Diseases of the Abdomen and Pelvis Syllabus, 1999, pp. 170-174.
Rosenstock et al., Abstract, "71st Scientific Sessions" http://www.call4abstracts.com/ada/ada11d1lb/index.php 02:22:24 pp. 1-3, (Nov. 2011).
Rosenstock J., et al., "Dose Range Effects of the New Once Daily GLP-1 Receptor Agonist AVE0010 Added to Metformin in Type 2 Diabetes," Diabetologia, 2008, vol. 51 (Suppl 1), pp. S66. Abstract 145.
Rosenstock J., et al., "Post-Meal Effects of Ave0010, A Once-Daily GLP-1 Receptor Agonist, in Type 2 Diabetes Inadequately Controlled on Metformin," Diabetes, 2009, vol. 58 (Suppl 1), pp. A151-A152. Abstract 564P.
Rosenstock J., et al., "Efficacy and Safety of Lixisenatide Once Daily vs Exenatiide Twice Daily in Type 2 DM Inadequately Controlled on Metformin (GetGoal-X)," 71st Scientific Sessions, Nov. 2011. Poster.
Rubino A., et al., "Delayed initiation of Subcutaneous Insulin therapy after Failure of oral Glucose-Lowering Agents in Patients with Type 2 Diabetes: A Population-Based Analysis in the UK," Diabetic Medicine, 2007, vol. 24 (12), pp. 1412-1418.
Sampson H.A., et al., "Second Symposium on the Definition and Management of Anaphylaxis: Summary Report—Second National institute of Allergy and infectious Disease/Food Allergy and Anaphylaxis Network Symposium," The Journal of Allergy and Clinical Immunology, 2006, vol. 117 (2), pp. 391-397.
Sanger F., et al., "The Amide Groups of Insulin," The Biochemical Journal, 1955, vol. 59 (3), pp. 509-518.
Sanofi and Zealand Pharma Press Release (Evaluate), "Additional Positive Results from Global Phase III Program With Lixisenatide for Type 2 Diabetes", (Apr. 12, 2011) pp. 1-3.
Sanofi's Lantus Draft Prescribing Information/Package Insert: "NDA 21-081 Draft package insert" (Sponsor revision #5) Date of submission: Apr. 20, 2000; see http://www.drugbank.ca/system/fds_labels/DB00047.pdf 1265922812; pp. 1-14.
Sanofi Press Release entitled "FDA Accepts Sanofi's New Drug Application for Basal Insulin Toujeo®," dated Jul. 8, 2014, pp. 1-2.
Sanofi Press Release; "Lyxumia (lixisenatide) in Combination with Basal insulin plus Oral Anti-Diabetics Significantly Reduced HbA1c and Post-Prandial Glucose"; Paris, France (Jun. 9, 2012) pp. 1-6.
Sanofi Press Release (Peron and Schaeffer), "Sanofi GetGoal Program on Lyxumia®, as an Add-on to Basal Insulin, Shows Significant Positive Phase III Results," Paris, France (May 31, 2011) pp. 1-2.
Sanofi Press release (Peron and Schaeffer); "Sanofi Reports Positive Results for Once-daily Lyxumia® (lixisenatide) in Combination with Lantus® (insulin glargine) in Type 2 Diabetes" Paris, France (Dec. 6, 2011) pp. 1-3.
Sanofi Press Release (Peron and Schaeffer), "Lyxumia® (lixisenatide) One-Step Regimen as Effective as Two-Step Regimen in Improving Glycemic Control in Type 2 Diabetes" Paris, France (Sep. 12, 2011) pp. 1-3.
Sanofi Press Release "Positive Results for Investigational Compound Lyxumia (Lixisenatide) Presented at American Diabetes Association's 71st Annual Scientific Sessions," (Jun. 24, 2011), pp. 1-5.
Sanofi Press Release (Sigurd), "Lixisenatide Significantly Reduces HbA1c Without Increasing Hypoglycemia in Patients Uncontrolled on Sulfonylureas", Pressmeddelande (Apr. 12, 2011) pp. 1-2.
Sanofi-aventis Press Release (Gabriel), "New Diabetes Compound AVE0010 Showed Clear Dose Response Results With Once-A-Day Injection in Phase IIb Study" Paris, France (Jun. 7, 2008) pp. 1-2.
Sanofi-aventis Press Release, "Once Daily Lixisenatide (AVE 0010) Given as Monotherapy Successfully Meets Phase III Study Endpoints in Diabetes" Paris, France (Apr. 15, 2010) pp. 1-2.
Sanofi-aventis Press Release (Peron and Schaeffer), "Sanofi-aventis Announces Positive Top-line Lixisentatide Phase III Results" Paris, France (Feb. 2, 2011) pp. 1-2.
Sanofi Press Release entitled "Sanofi Receives FDA Approval of Once-Daily Basal Insulin Toujeo®," dated Feb. 26, 2015, pp. 1-4.
Schapira A.H., "Causes of Neuronal Death in Parkinson's Disease," Advances in Neurology, 2001, vol. 86, pp. 155-162.
Schellenberger V., et al., "Attempts for Quantifying the S' Subsite Specificity of Serine Proteases, Selected Papers Presented at the 2nd International Meeting on the Molecular and Cellular Regulation of Enzyme Activity, Advances in the Biosciences, Peptides and Proteases," Recent Advances, 1987, vol. 65, pp. 159-166.
Schellenberger V., et al., "Protease-Catalyzed Kinetically Controlled Peptide Synthesis," Angewante Chemie, 1991, vol. 30 (11), pp. 1437-1449.
Schindowski K., et al., "Impact of Aging: Sporadic, and Genetic Risk Factors on Vulnerability to Apoptosis in Alzheimer's Disease," Neuromolecular Medicine, 2003, vol. 4 (3), pp. 161-178.
Schmitz C., et al., "Hippocampal Neuron Loss Exceeds Amyloid Plaque Load in a Transgenic Mouse Model of Alzheimer's Disease," The American Journal of Pathology, 2004, vol. 164 (4), pp. 1495-1502.
Schwartz G.P., et al., "A Superactive Insulin: [B10-Aspartic Acid]Insulin(Human)," Proceedings of the National Academy of Sciences of the United States of America, 1987, vol. 84 (18), pp. 6408-6411.
Search Report of the Intellectual Property Corporation of Malaysia for Malaysian Patent Application No. PI 2011006204; dated Sep. 15, 2015, pp. 1-3.
Secnik Boye K., et al., "Patient-Reported Outcomes in a Trial of Exenatide and Insulin Glargine for the Treatment of Type 2 Diabetes," Health and Quality of Life Outcomes, 2006, vol. 4 (80), pp. 1-8.
Seino Y., et al., "Report of the Committee on the Classification and Diagnostic Criteria of Diabetes Mellitus," Journal of the Japan Diabetes Society, 2010, vol. 53, pp. 450-467 (in Japanese) English summary also provided.
Seino Y., et al., "Randomized, Double-Blind, Placebo-Controlled Trial of the Once-Daily GLP-1 Receptor Agonist Lixisenatide in Asian Patients with Type 2 Diabetes Insufficiently Controlled on Basal Insulin with or without a Sulfonylurea (Getgoal-L-Asia)," Diabetes, Obesity and Metabolism, 2012, vol. 14 (10), pp. 910-917.
Sharplin P., et al., "Improved Glycaemic Control by Switching from Insulin NPH to Insulin Glargine: A Retrospective Observational Study," Cardiovascular Diabetology, 2009, vol. 8 (3), pp. 1-8.
Sherer T.B., et al., "Subcutaneous Rotenone Exposure Causes Highly Selective Dopaminergic Degeneration and A-Synuclein Aggregation," Experimental Neurology, 2003, vol. 179, pp. 9-16.
Sluzky V., et al., "Kinetics of Insulin Aggregation in Aqueous Solutions Upon Agitation in the Presence of Hydrophobic Surfaces," Proceedings of the National Academy of Sciences of the United States of America, 1991, vol. 88 (21), pp. 9377-9381.
Smolka M.B., et al., "Optimization of the Isotope-Coded Affinity Tag-Labeling Procedure for Quantitative Proteome Analysis," Analytical Biochemistry, 2001, vol. 297 (1), pp. 25-31.
Sporn M.B., et al., "Chemoprevention of Cancer," Carcinogenesis, 2000, vol. 21 (3), pp. 535-530.
St. John Providence Health Center, "Preventing Obesity" http://www.stjohnprovidence.org/HealthInfolib/swarticle.aspx?type=85&id=P07863, Retrieved Aug. 22, 2013, pp. 1-2.
Starkova N.T., "Clinical Endocrinology," Guide for physicians, Medicine, 1991, pp. 192-262.
Stolk R.P., et al., "Insulin and Cognitive Function in an Elderly Population the Rotterdam Study," Diabetes Care, 1997, vol. 20 (5), pp. 792-795.
Summary of Product Characteristics Lyxumia 10 micrograms solution for injection, pp. 1-93, published Mar. 14, 2013.

(56) References Cited

OTHER PUBLICATIONS

Sundby F., "Separation and Characterization of Acid-induced Insulin Transformation Products by Paper Electrophoresis in 7 M Urea," The Journal of Biological Chemistry, 1962, vol. 237 (11), pp. 3406-3411.
Tanner C.M., et al., "Rotenone, Paraquat, and Parkinson's Disease," Environmental Health Perspectives, 2011, vol. 119 (6), pp. 866-872.
Tempero M.A., "How I Treat Pancreatic Ductal Adenocarcinoma," Current Clinical Issues, Journal of Oncology Practice, 2008, vol. 4 (1), pp. 46-47.
Teramoto S., et al., "Exendin-4, a Glucagon-Like Peptide-1 Receptor Agonist, provides Neuroprotection in Mice Transient Focal Cerebral Ischemia," Journal of Cerebral Blood Flow and Metabolism, 2011, vol. 31 (8), pp. 1696-1705.
Tetich M., et al., "Neuroprotective Effects of (24R)-1,24-Dihydroxycholecalciferol in Human Neuroblastoma SH-SY5Y Cell Line," The Journal of Steroid Biochemistry and Molecular Biology, 2004, vol. 89-90 (1-5), pp. 365-370.
Tews D., et al., "Enhanced Protection against Cytokine- and Fatty Acid-Induced Apoptosis in Lns-1 Beta-Cells by Combined Treatment with Insulin Glargine and the Novel GLP-1 Receptor Agonist Ave0010," Diabetes, 2007, vol. 56 (Suppl 1), pp. A72-A73.
Thong K.Y., et al., "Safety, Efficacy and tolerability of Exenatide in Combination with Insulin in the Association of British Clinical Diabetologists Nationwide Exenatide Audit," Diabetes, Obesity and Metabolism, 2011, vol. 13 (8), pp. 703-710.
Thurow H., et al., "Stabilisation of Dissolved Proteins against Denaturation at Hydrophobic Interfaces," Diabetologia, 1984, vol. 27 (2), pp. 212-218.
Toth M.L., et al., "Neurite Sprouting and Synapse Deterioration in the Aging Caenorhabditis Elegans Nervous System," The Journal of Neuroscience, 2012, vol. 32 (26), pp. 8778-8790.
Translation of pp. 1109, 1116 and 1117 of "Clinical Effectiveness of Long-Term Administration of Bay g5421 (Acarbose) on Insulin-Treated Diabetes," Jpn. Pharmacal. Ther; 1996 vol. 24 No. 5: 1109-1129, pp. 1-4.
Translation of pp. 121 and 124 of Igaku to Yakugaku, "Utility of Voglibose Long-term Combined Therapy in Non-Insulin Dependent Diabtetic Patients with Little Effective of Sulfonylureas," 1999, vol. 42, No. 1: 121-129, pp. 1-3.
Translation of pp. 2346 and 2348 of Rinsho to Kenkyu, "Effectiveness of Combination Therapy Using Voglibose and Insulin in Patients with NIDDM," 1997, vol. 74, No. 9: 2346-2352, pp. 1-3.
Translation of pp. 750, 753 and 754 of Igaku No Ayumi, "Incretin Receptors," May 2010, vol. 233; No. 9: 750-754, pp. 1-4.
Turner R.C., et al., "Glycemic Control with Diet, Sulfonylurea, Metformin, or Insulin In Patients with Type 2 Diabetes Mellitus: Progressive Requirement for Multiple therapies (UKPDS 49)," JAMA, 1999, vol. 281 (21), pp. 2005-2012.
UK Prospective Diabetes Study (UKPDS) Group, "Effect of intensive Blood-Glucose Control with Metformin on Complications in Overweight Patients with Type 2 Diabetes (UKPDS 34)," Lancet, 1998, vol. 352 (9131), pp. 854-865.
UK Prospective Diabetes Study (UKPDS) Group, "Intensive Blood-Glucose Control with Sulphonylureas or Insulin Compared with Conventional Treatment and Risk of Complications in Patients with Type 2 Diabetes (UKPDS 33)," the Lancet, 1998, vol. 352, pp. 837-853.
Valle J., et al., "Cisplatin Plus Gemcitabine Versus Gemcitabine for Biliary Tract Cancer," The New England Journal of Medicine, 2010, vol. 362 (14), pp. 1273-1281.
Van Delden, "Pancreas-Carcinoma, CT Assessment of Resectability," Radiology Department of the Academical Medical Centre, Apr. 2006, pp. 1-12.
Varadarajan S., et al., "Review: Alzheimer's Amyloid Beta-Peptide-Associated Free Radical Oxidative Stress and Neurotoxicity," Journal of Structural Biology, 2000, vol. 130 (2-3), pp. 184-208.
Venezia V., et al., "Apoptotic Cell Death and Amyloid Precursor Protein Signaling in Neuroblastoma SH-SY5Y Cells," Annals of the New York Academy of Sciences, 2004, vol. 1030, pp. 339-347.

Victoza® Annex I—Summary of product characteristics. First published 2009, pp. 1-32.
Victoza Press Release, "Diabetes drugs show promise in Alzheimer's" published Jan. 17, 2011, pp. 1-2.
Victoza® Product information—European Medicines Agency, first published Aug. 7, 2009, pp. 1-2.
Volund A., et al., "In Vitro and in Vivo Potency of Insulin Analogues Designed for Clinical Use," Diabetic Medicine, 1991, vol. 8 (9), pp. 839-847.
Vora J., et al., "Incretin-Based therapy in Combination with Basal Insulin: A Promising Tactic for the Treatment of Type 2 Diabetes," Diabetes & Metabolism, 2013, vol. 39 (1), pp. 6-15.
Wafa W.S., et al., "Use of U-500 Regular Insulin in Type 2 Diabetes," Diabetes Care, 2006, vol. 29 (9), pp. 2175-2176.
Wajchenberg B.L., "Clinical Approaches to Preserve Beta-Cell Function in Diabetes," Advances in Experimental Medicine and Biology, 2010, vol. 654, pp. 515-535.
Wang L., et al., "Real-World Outcomes of US Employees with Type 2 Diabetes Mellitus Treated with Insulin Glargine or Neutral Protamine Hagedorn Insulin: A Comparative Retrospective Database Study," BMJ Open, 2013, vol. 3 (4), pp. e002348 1-9.
Ward J.D., "Diabetic Neuropathy," British Medical Bulletin, 1989, vol. 45 (1), pp. 111-126.
Watson G.S., et al., "Insulin increases CSF Abeta42 Levels in Normal Older Adults," Neurology, 2003, vol. 60 (12), pp. 1899-1903.
Werner et al., "Abstract, Insulin Glargine U-100 Has a Favourable Time-Action Profile Compared to U-40 or NPH Insulin in Healthy, Normoglycaemic Dogs", Poster 37th Annual Meeting of Endocrine Society of India, Tirupati, A.P., India, ESICON, 2007, p. 2.
Werner U., et al., "Pharmacological Profile of Lixisenatide: A New GLP-1 Receptor Agonist for the Treatment of Type 2 Diabetes," Regulatory Peptides, 2010, vol. 164 (2-3), pp. 58-64.
Weyer C., et al., "Long-Term Changes in Insulin Action and Insulin Secretion Associated with Gain, Loss, Regain and Maintenance of Body Weight," Diabetologia, 2000, vol. 43 (1), pp. 36-46.
White I.R., et al., "Randomized Clinical Trials with Added Rescue Medication: Some Approaches to their Analysis and interpretation," Statistics in medicine, 2001, vol. 20 (20), pp. 2995-3008.
Whittingham J.L., et al., "Insulin At pH 2: Structural Analysis of the Conditions Promoting Insulin Fibre formation," Journal of Molecular Biology, 2002, vol. 318 (2), pp. 479-490.
WHO BMI classification, accessed at URL apps.who.int/bmi/index.jsp?introPage=itrol_3.html, Sep. 9, 2013, one page.
WHO Drug Information vol. 22(2), list 99, p. 142 (lixisenatide) (Jul. 2008).
WHO Rational Use of Medicines, http://www.whoint/medicines/areas/rational_use/en/downloaded Dec. 18, 2014 10:02:48 AM; pp. 1-4 (2012).
Widjaja a., et al., "UKPDS 20: Plasma Leptin, Obesity, and Plasma Insulin in Type 2 Diabetic Subjects," the Journal of Clinical Endocrinology and Metabolism, 1997, vol. 82 (2), pp. 654-657.
Wiernsperger N. F., et al., "The Antihyperglycaemic Effect of Metformin: Therapeutic and Cellular Mechanisms," Drugs, 1999, vol. 58 (Suppl 1), pp. 31-39.
Wirths O., et al., "Intraneuronal Abeta Accumulation Precedes Plaque formation in beta-Amyloid Precursor Protein and Presenilin-1 Double-Transgenic Mice," Neuroscience Letters, 2001, vol. 306 (1-2), pp. 116-120.
Wirths O., et al., "Intraneuronal APP/A Beta Trafficking and Plaque formation in Beta-Amyloid Precursor Protein and Presenilin-1 Transgenic Mice," Brain Pathology, 2002, vol. 12 (3), pp. 275-286.
Wirths O., et al., "Reelin in Plaques of Beta-Amyloid Precursor Protein and Presenilin-1 Double-Transgenic Mice," Neuroscience Letters, 2001, vol. 316 (3), pp. 145-148.
Wollen K.A., "Alzheimer's Disease: the Pros and Cons of Pharmaceutical, Nutritional, Botanical, and Stimulatory therapies, with a Discussion of Treatment Strategies from the Perspective of Patients and Practitioners," Alternative Medicine Review, 2010, vol. 15 (3), pp. 223-244.
Written Opinion of the ISA for International Application No. PCT/EP2011/058079, mailed Mar. 22, 2012, pp. 1-8.

(56) References Cited

OTHER PUBLICATIONS

Xie H., et al., "Characterization of Protein Impurities and Site-Specific Modifications Using Peptide Mapping with Liquid Chromatography and Data Independent Acquisition Mass Spectrometry," Analytical Chemistry, 2009, vol. 81 (14), pp. 5699-5708.
Yki-Jarvinen H., et al., "Insulin Glargine or Nph Combined with Metformin in Type 2 Diabetes: The Lanmet Study," Diabetologia, 2006, vol. 49 (3), pp. 442-451.
Yki-Jarvinen H., "Thiazolidinediones," The New England Journal of Medicine, 2004, vol. 351 (11), pp. 1106-1118.
Yoon N. M., et al., "Exenatide Added to Insulin therapy: A Retrospective Review of Clinical Practice Over Two Years in an Academic Endocrinology Outpatient Setting," Clinical Therapeutics, 2009, vol. 31 (7), pp. 1511-1523.
Zealand Pharma Press Release entitled "Sanofi-Aventis finalize phase lia clinical study with GLP-1 agonist for type 2 diabetes licensed from Zealand Pharma" dated Mar. 3, 2005, one page.
Ziemer D.C., et al., "Clinical Inertia Contributes to Poor Diabetes Control in a Primary Care Setting," The Diabetes Educator, 2005, vol. 31 (4), pp. 564-571.
Ziessman H.A., et al., "Sincalide-Stimulated Cholescintigraphy: A Multicenter Investigation to Determine Optimal Infusion Methodology and Gallbladder Ejection Fraction Normal Values," Journal of Nuclear Medicine, 2010, vol. 51 (2), pp. 277-281.
Zimmet P., et al., "Clinical Efficacy of Metformin Against Insulin Resistance Parameters: Sinking the Iceberg," Review Article, Drugs, 1999, vol. 58 (Suppl 1), pp. 21-28.
Zinman B., et al., "Efficacy and Safety of the Human Glucagon-Like Peptide-1 Analog Liraglutide in Combination with Metformin and Thiazolidinedione in Patients with Type 2 Diabetes (Lead-4 Met+TZD)," Diabetes Care, 2009, vol. 32 (7), pp. 1224-1230.
Zinman B., "The Physiologic Replacement of Insulin an Elusive Goal," The New England Journal of Medicine, 1989, vol. 321 (6), pp. 363-370.
Abraira et al., "Glycaemic separation and risk factor control in the Veterans Affairs Diabetes Trial: an interim report" Diabetes Obes Metab 11(2):150-56 (2009; Epub 2008 Jul. 29).
American Diabetes Association, "Type 2 Diabetes in Children and Adolescents," Diabetes Care, Mar. 2000, vol. 23 (3), pp. 381-389.
American Diabetes Association, "Standards of Medical Care in Diabetes—2011," Diabetes Care, Jan. 2011, vol. 34 (Suppl 1), pp. S11-S61.
Ampudia-Blasco et al., "Basal Plus Basal-Bolus approach in type 2 diabetes" Diabetes Technol Ther. 13 Suppl1: S75-83 (Jun. 2011).
Aquiliante C.L., "Sulfonylurea Pharmacogenomics in Type 2 Diabetes: The Influence of Drug Target and Diabetes Risk Polymorphisms," Expert Review of Cardiovascular Therapy, Mar. 2010, vol. 8 (3), pp. 359-372.
Atkinson et al., "validation of a general measure of treatment satisfaction, the Treatment Satisfaction Questionnaire for Medication (TSQM), using a national panel study of chronic disease" Health Qual Life Outcomes, 2:12, pp. 1-13 (Feb. 2004).
Beckman et al., "Diabetes and atherosclerosis: epidemiology, pathophysiology, and management" JAMA 287 (19):2570-81 (May 2002).
Brazier et al., "Testing the validity of the Euroqol and comparing it with the SF-36 health survey questionnaire," Qual Life Res 2(3):169-80 (Jun. 1993).
Byetta@ Product information, EMA pp. 1-2, accessed Jun. 10, 2016.
Byetta@ Summary of product characteristics, ANNEX I, pp. 1-71, (2011).
Canadian Cardiovascular Society Grading of Angina Pectoris, From http://www.sscts.org/pages/Classificationanginaccs.aspx. Accessed May 27, 2016, one page.
Canadian Diabetes Association, Clinical Practice Guidelines Expert Committee, Canadian Diabetes Association 2008, Clinical Practice Guidelines for the Prevention and Management of Diabetes in Canada, Canadian Journal of Diabetes, 2008, pp. S162-S167.
Cannon P.C., et al., "Intensive versus Moderate Lipid Lowering with Statins after Acute Coronary Syndromes." New England Journal of Medicine, Apr. 2004; Epub 2004 Mar. 8, 2004, vol. 350 (15), pp. 1495-504.
Centers for Disease Control and Prevention, National Diabetes Fact Sheet: General Information and National Estimates on Diabetes in the United States, 2003, Revolution Education Atlanta, GA: U.S. Department of Health and Human Services, Centers for Disease Control and Prevention, 2004, pp. 1-8.
Classification of Functional Capacity and Objective Assessment, My.AmericanHeart, 1994—last accessed Oct. 23, 2015, pp. 1-2.
Clinical Trials Archive for Trial No. NCT00688701 updated Sep. 30, 2012. Accessed at: https://clinicaltrials.gov/archive/NCT00688701/2012.09.30/changes Accessed on Jun. 2, 2016, pp. 1-5 submitted.
Clinical Trials History for Trial No. NCT00688701 last updated Mar. 25, 2014. Accessed at https://clinicaltrials.gov/archive/Mar. NCT00688701 Accessed on Jun. 2, 2016, pp. 1-2 submitted.
Community register of medicinal products for human use, Chemical Subgroup A10BX, "Lyxumia" European Commission—Public Health, p. 1-2 (May 2, 2013).
D'Alessio et al., "The role of dysregulated glucagon secretion in type 2 diabetes" Diabetes, Obesity and Metabolism, 13(Supppl.1):126-132 (Oct. 2011 ).
Das et al., "The British Cardiac Society Working Group Definition of Myocardial Infarction: Implications for Practice," Heart, 2005, vol. 92 (1), pp. 21-26, (Jan. 2006; Epub Apr. 14, 2005).
De Lemos et al., "Early intensive vs. A delayed conservative simvastatin strategy in patients with acute coronary Syndromes: phase Z of the a to Z trial." Jama 292(11):1307-16 (Sep. 2004; Epub 2004 Aug. 30).
Definition of "Combination", Concise Oxford English Dictionary, edited by a. Stevenson and M. Waite, Oxford University press, 12th Edition, Aug. 2011, 4 pages submitted, see p. 285.
Definition of Phase, Clinical Trials.gov NIH, accessed, Mar. 2016, one page.
Del Prato & Tiengo, The importance of first-phase insulin secretion: implications for the therapy of type 2 diabetes mellitus. Diabetes Metab Res Rev. 17(3):164-74 (May-Jun. 2001).
Del Prato et al., "Global Partnership for Effective Diabetes Management Tailoring treatment to the individual in type 2 diabetes practical guidance from the Global partnership for effective diabetes management" Int J Clin Pract 64 (3):295-304 (Feb. 2010).
DeWitt & Hirsch, "Outpatient insulin therapy in type 1 and type 2 diabetes mellitus: scientific review." JAMA 289 17):2254-64 (May 2003).
Diabetes Control and Complications Trial/ Epidemiology of Diabetes Interventions and Complications Research Group, "Intensive Diabetes Treatment and Cardiovascular Disease in Patients with Type 1 Diabetes," New England Journal Medicine, Dec. 2005, vol. 353 (25), pp. 2643-2259.
Diabetes Control and Complications Trial, "Intensive diabetes therapy and carotid intima-media thickness in type 1 diabetes," New England Journal Medicine Jun. 2003, vol. 348 (23), pp. 2294-2303.
Dinneen & Gerstein, "The association of microalbuminuria and mortality in non-insulin dependent diabetes mellitus. A systematic overview of the literature." Arch Intern Med 157(13):1413-8 (Jul. 1997).
Dolan, "Modeling valuations for EuroQol health states." Med Care 35(11):1095-1108 (Nov. 1997).
Druet et al., "Characterization of Insulin Secretion and Resistance in Type 2 Diabetes of Adolescents," the Journal of Clinical Endocrinology & Metabolism, Feb. 2006, vol. 91 (2), pp. 401-404 (Epub Nov. 15, 2005).
Dunning & Gerich, "The Role of alpha-cell Dysregulation in Fasting and Postprandial Hyperglycemia in Type 2 Diabetes and Therapeutic Implications" Endocrine Reviews 28(3):253-83 (Apr. 2007).
EMA—European Medicines Agency, "Note for guidance on non-clinical safety studies for the conduct of human clinical Trials and marketing authorization for pharmaceuticals," Jul. 2008, pp. 1-22.
Encyclopedia of Drugs, "Metformin" Moscow, Drug Register of 2001, p. 549, English translation provided pp. 1-2.

(56) References Cited

OTHER PUBLICATIONS

English translation of the TIPO Search Report for ROC Patent Application No. 101131466; dated Mar. 2, 2016, one page.
European Medicines Agency, Committee for Medicinal Products for Human Use (CHMP), "Assessment Report—Lyxumia", Nov. 28, 2012, pp. 1-81.
Game, "Novel hypoglycaemic agents: Considerations in patients with chronic kidney disease" Nephron Clin Pract. 126(1):14-18 (Jan. 11, 2014).
EuroQol Group, "EuroQol-a new facility for the measurement of health-related quality of life." Health policy (Amsterdam, Netherlands) 16(3):199-208 (Dec. 1990).
Extended European Search Report for European Application No. 15159064.3, dated Oct. 19, 2015, pp. 1-4.
FDA, Food and Drug Administration, CFR—Code of Federal Regulations Title 21, Chapter 1, Subchapter D, Part 312.21, "Phases of an investigation," Apr. 1, 2015, pp. 1-2.
FDA, Food and Drug Administration. Guidance for Industry—Diabetes Mellitus: Developing Drugs and Therapeutic Biologics for Treatment and Prevention. pp. 1-34 (Feb. 2008).
Final Rejection issued in U.S. Appl. No. 12/617,805; mailed May 25, 2016, pp. 1-9.
Final Rejection issued in U.S. Appl. No. 13/633,496; mailed Aug. 26, 2015, pp. 1-16.
Final Rejection issued in U.S. Appl. No. 13/633,563; mailed Apr. 8, 2016, pp. 1-12.
NCT00976937, ClinicalTrials.gov, "24-week Study Comparing Lixisenatide (AVE0010) to Sitagliptin as add-on to Metformin in Obese Type 2 Diabetic Patients Younger Than 50," last updated Mar. 10, 2014, Retrieved Aug. 31, 2016, pp. 1-5.
Final Rejection issued in U.S. Appl. No. 14/303,895; mailed Apr. 27, 2015, pp. 1-10.
Final Rejection issued in U.S. Appl. No. 13/382,772; mailed Feb. 24, 2016, pp. 1- 36.
Forman et al., "Higher Levels of Albuminuria within the Normal Range Predict Incident Hypertension." Journal of American Social Nephrology, Oct. 2008, vol. 19 (10), pp. 1983-1988.
Gerstein et al., "Albuminuria and risk of cardiovascular events, death, and heart failure in diabetic and nondiabetic Individuals." JAMA 286(4):421-6 (Jul. 2001).
Gromada et al., "Alpha-Cells of the Endocrine Pancreas: 35 Years of Research but the Enigma Remains" Endocrine Reviews 28(1):84-116 (Jan. 2007).
Giorda et al., "Pharmacokinetics, safety, and efficacy of DPP-4 inhibitors and GLP-1 receptor agonists in patients with type 2 diabetes mellitus and renal or hepatic impairment. A systematic review of the literature." Endocrine 46(3):406-19 (Aug. 2014; epub Feb. 8, 2014).
Harkavyi & Whitton, "Glucagon-like peptide 1 receptor stimulation as a means of neuroprotection" British Journal of Pharmacology 159(3):495-501 (2010; Epub Jan. 29, 2010).
Hinnen D.A., "Therapeutic Options for the Management of Postprandial Glucose in Patients With Type 2 Diabetes on Basal Insulin," Clinical Diabetes, 2015, vol. 33 (4), pp. 175-80.
Holman et al., "Three-year efficacy of complex insulin regimens in type 2 diabetes." N Engl J Med. 361 (18):1736-47 (Oct. 2009; Epub Oct 22, 2009).
IDF Clinical Guidelines Task Force, Global Guideline for Type 2 Diabetes, Brussels: International Diabetes Federation, Aug. 2005, pp. 1-82.
IDF, International Diabetes Federation Guideline Development Group, "Guideline for management of postmeal glucose in diabetes," Diabetes Research Clinical Practice, 2012, pp. 1-13.
Inzucchi et al., "Management of hyperglycaemia in type 2 diabetes: a patient-centered approach. Position statement of the American Diabetes Association (ADA) and the European Association for the Study of Diabetes (EASD)." Diabetologia. 55(6):1577-96 (Jun. 2012; Epub Apr. 20, 2012).

Johnson et al., "Diabetes, Insulin Resistance, and Metabolic Syndrome in Horses," Journal of Diabetes Science and Technology, May 2012, vol. 6 (3), pp. 534-540.
Jones et al., "Effect of Metformin in Pediatric Patients with Type 2 Diabetes: A Randomized Controlled Trial," Diabetes Care, Jan. 2002, vol. 25 (1), pp. 89-94.
Juniper et al., "Determining a minimal important change in a disease-specific quality of life questionnaire." J Clin Epidemiol 47(1):81-87 (Jan. 1994).
Kelly et al., "Systematic Review: Glucose Control and Cardiovascular Disease in Type 2 Diabetes." Annals Internal Medicine, 2009, vol. 151 (6), pp. 394-403, (Sep. 2009; Epub Jul. 20, 2009).
Kendall et al., "Clinical Application of Incretin-Based Therapy: Therapeutic Potential, Patient Selection and Clinical Use." European Journal of Internal Medicine, Jul. 2009, vol. 20 (Suppl 2), pp. S329-S339.
Khaw et al., "Glycated Haemoglobin, Diabetes, and Mortality in Men in Norfolk Cohort of European Prospective Investigation of Cancer and Nutrition (EPIC Norfolk)." BMJ, Jan. 2001, vol. 322 (7277), pp. 15-18.
Kim et al., "Retinopathy in Monkeys with Spontaneous Type 2 Diabetes" Investigative Opth & Visual Science, Dec. 2004, vol. 45 (12), pp. 4543-4553.
King et al., Global burden of diabetes, 1995-2025. Prevalence, numerical estimates and projections. Diabetes Care 21(9):1414-31 (Sep. 1998).
Kolotkin et al., "Assessing impact of weight on quality of life." Obes Res. 3(1):49-56 (Jan. 1995).
Kolotkin et al., "Development of a brief measure to assess quality of life in obesity." Obes Res. 9(2):102-11 (Feb. 2001).
Kondrat'ev VA Methodical Guidelines, May 7, 2010, p. 5 (in Russian only), found on Mar. 24, 2016, found from Internet: StudFields.ru>preview/4510743). — English summary submitted.
Korytkowski, "When oral agents fail: practical barriers to starting insulin." Int J Obes Relat Metab Disord. 26 Suppl 3 :S18-24 (Sep. 2002).
Lovshin & Drucker, "Incretin-based therapy for type 2 diabetes mellitus." Nat. Rev. Endocrinol. 5(5):262-69 (May 2009).
Madsbad, "Impact of Postprandial Glucose Control on Diabetes-Related Complications: How is the Evidence Evolving?" Journal of Diabetes and Its Complications, 2016, vol. 30, pp. 374-385, Available online Oct. 9, 2015.
McFarlane, "Insulin therapy and type 2 diabetes: management of weight gain," J Clin Hypertens (Greenwich). 11 (10):601-7 (Oct. 2009).
Meadows et al., "Adaptation of the diabetes health profile (DHP-1) for use with patients with Type 2 diabetes mellitus: psychometric evaluation and cross-cultural comparison," Diabet. Med. 17(8):572-80 (Aug. 2000).
Meadows et al, "The diabetes health profile (DHP): a new instrument for assessing the psychosocial profile of insulin requiring patients: development and psychometric evaluation," Qual. Life Res. 5(2):242-54 (Apr. 1996).
Meier et al., "Contrasting Effects of Lixisenatide and Liraglutide on Postprandial Glycemic Control, Gastric Emptying, and Safety Parameters in Patients With Type 2 Diabetes on Optimized Insulin Glargine With or Without Metformin: A Randomized, Open-Label Trial" Diabetes Care 38(7):1263-73 (Jul. 2015).
Meier et al., "Effect of lixisenatide vs liraglutide on glycaemic control, gastric emptying and safety parameters in optimised insuline glargine type 2 diabetes mellitus +/- metformin" Abstract and Poster 926, 5oth EASD Annual Meeting, Vienna, Austria Sep. 15-19, 2014, pp. 1-3.
Merck Index, "Metformin", The Merck Index, 15th Edition (2013), RSC Publishing, 4 pages submitted, see entry 6009, p. 1102.
Miyazaki et al., "Improved Glycemic Control and Enhanced Insulin Sensitivity in Type 2 Diabetic Subjects Treated with Pioglitazone", Diabetes Care, Apr. 2001, vol. 24(4), pp. 710-719.
Monnier & Colette, "Addition of rapid-acting insulin to basal insulin therapy in type 2 diabetes: indications and modalities." Diabetes Metab 32(1):7-13 (Feb. 2006).

(56) References Cited

OTHER PUBLICATIONS

Monnier et al., "Postprandial and Basal Glucose in Type 2 Diabetes: Assessment and Respective Impacts" Diabetes Technology & Therapeutics, 2011, vol. 13 (Suppl 1 ), pp. S25- S32.

Nathan et al., "Medical Management of Hyperglycemia in Type 2 Diabetes: A Consensus Algorithm for the Initiation and Adjustment of Therapy" Diabetes Care, Jan. 2009, vol. 32 (1), pp. 193-203.

Nathan et al., "Modem-day clinical course of type 1 diabetes mellitus after 30 years' duration: the diabetes control and complications trial/epidemiology of diabetes interventions and complications and Pittsburgh epidemiology of diabetes complications experience (1983-2005)." Arch Intern Med. 169(14):1307-16 (Jul. 2009).

Hasslacher et al., "Diabetic kidney disease" Exp and Clin Endocrinol Diabetes 122(7):391-94 (Jul. 2014).

Nihonn-lyakuhin-shu lryoyaku "Pioglitazone hydrochloride, Insulin sensitizing hypoglycemic agent" 2009 Edition, Jiho Inc. page 1901 (2009). English summary submitted.

NCT00713830, Clinical Trials.gov "GLP-1 Agonist in Patients with Type 2 Diabetes for Glycemic Control and Safety Evaluation, on Top of Sulfonylurea", 2016, pp. 1-3, accessed Mar. 16, 2016, (Updated Jul. 13, 2008).

NCT00866658 ClinicaiTrials.gov, "GLP-1 Agonist AVE0010 in Patients with Type 2 Diabetes for Glycemic Control Safety Evaluation, on Top of Basil Insulin+/- Sulfonylurea," 2016, pp. 1-3, accessed Mar. 16, (Updated Jan. 010).

NCT01169779, Clinical Trials.gov, "Efficacy and Safety of Lixisenatide in Patients with Type 2 Diabetes Mellitus Insufficiently Controlled by Metformin," 2016, pp. 1-3, accessed Mar. 16, 2016, (updated Mar. 28, 2011).

NICE, National Institute for Health and Care Excellence, "Evidence Summary: New Medicine, ESNM26: Type 2 Diabetes: lixisenatide; Key Points from the Evidence," Sep. 24, 2013, pp. 1-26.

NIH, National Institute of Diabetes and Digestive and Kidney Disease, "Hypoglycimia," Mar. 16, 2016, pp. 1-8.

Nilsson A., et al., "Effects of GI vs Content of Cereal Fibre of the Evening Meal on Glucose Tolerance at a Subsequent Standardized Breakfast," European Journal of Clinical Nutrition, Jun. 2008, vol. 62 (6), pp. 712-720 (Epub May 23, 2007).

Non-Final Rejection in U.S. Appl. No. 13/633,496; mailed Apr. 21, 2016, pp. 1-12.

Non-Final Rejection issued in U.S. Appl. No. 13/467,707; mailed Jun. 30, 2016, pp. 1-9.

Nowels et al., "Validation of the EQ-50 quality of life instrument in patients after myocardial infarction." Qual Life Res 14(1):95-105 (Feb. 2005).

Olansky, "Do Incretin-Based Therapies Cause Acute Pancreatitis?," Journal of Diabetes Science and Technology, Jan. 2010, vol. 4 (1), pp. 228-229.

Park et al., "Long-Term Treatment of Glucagon-Like Peptide-1 Analog Exendin-4 Ameliorates Diabetic Nephropathy through Improving Metabolic Anomalies in db/db Mice." Journal American Society Nephrology, 2007, vol. 18 (4), pp. 1227-1238, (Apr. 2007; Epub Mar. 14, 2007).

Pinhas-Hamiel et al., "Clinical Presentation and Treatment of Type 2 Diabetes in Children," Pediatric Diabetes, Dec. 2007, vol. 8 (Suppl. 9), pp. 16-27.

Pi-Sunyer, "The Impact of Weight Gain on Motivation, Compliance, and Metabolic Control in Patients with Type 2 Diabetes Mellitus." Postgrad Med. 121(5):94-107 (Sep. 2009).

Ratner et al., "Efficacy and safety of lixisenatide once-daily versus placebo in patients with type 2 diabetes mellitus insufficiently controlled on sulfonylurea +/- metformin (GetGoai-S)" Presentation Abstract for Presentation No. 785. 47th EASD Annual Meeting, Lisbon, Sep. 12-16, 2011, pp. 1-3.

Ray et al., "Effect of intensive control of glucose on cardiovascular outcomes and death in patients with diabetes mellitus: a meta-analysis of randomized controlled trials." Lancet 373(9677):1765-72 (May 2009).

Register of medicaments (RM), 2003, issue 10, p. 517.

Remington: The Science and Practice of Pharmacy, Twentieth Edition, Lippincott Williams & Wilkins, USA, "Oral Hypoglycemic and Hyperglycemic Drugs" pp. 1373 and 1375; (2000).

Remington: The Science and Practice of Pharmacy, Twentieth Edition, Lippincott Williams & Wilkins, USA, "Pancreatic Disorders" pp. 1081-82 and "Metformin Hydrochloride" p. 1375, (2000,5 pages).

Rosenstock et al., Advancing Basal Insulin Glargine with Prandial Lixisenatide QD vs. Insulin Glulisine QD or TID in T2DM: The GetGoaiDuo2 Evidence-Based Trial (NCT01768559). Poster 107 -Lb, Presented on Sunday, Jun. 7, 2015, 75th Scientific Sessions of the American Diabetes Association, Boston, Massachusetts Jun. 5-9, 2015.

Russell-Jones & Khan, Insulin-associated weight gain in diabetes: causes, effects and coping strategies. Diabetes Obes Metab. 9(6):799-812 (Nov. 2007).

Sanofi-Aventis Press Release, "A Promising R&D Portfolio, Well Positioned to Deliver Future Growth," Sep. 17, 2007, pp. 1-11.

Schernthaner et al., "Is the ADA/EASD algorithm for the management of type 2 diabetes (Jan. 2009) based on evidence or opinion? a critical analysis." Diabetologia.53(7):1258-69 (Jul. 2010; Epub Mar. 31, 2010 ).

Schwartz et al., "New Equations to Estimate GFR in Children with CKD," Journal of the American Society of Nephrology, Mar. 2009, vol. 20 (3), pp. 629-637 (Epub Jan. 21, 2009).

Seino et al., "Lixisenatide significantly improves glycemic control in Asian patients with T2DM insufficiently controlled on basal insulin± SU." Diabetes, Abstract book for 71st Scientific Session. Page A76; Abstract 278-0R (2011).

Shaw et al., "US valuation of the EQ-5D health states: development and testing of the D1 valuation model." Med Care 43(3):203-20 (Mar. 2005).

Spertus et al., "Monitoring the quality of life in patients with coronary heart disease." Am J Cardiol. 74(12):1240-44 (Dec. 1994).

Spertus et al., "Development and Evaluation of the Seattle Anginal Questionnaire: a New Functional Status Measure for Coronary Artery Disease." Journal American College of Cardiology, Feb. 1995, vol. 25 (2), pp. 333-341.

Spertus et al., "Health Status Predicts Long-Term Outcome in Outpatients with Coronary Disease." Circulation, Jul. 2002, vol. 106 (1 ), pp. 43-49.

Srinivasan et al., "Animal Models in Type 2 Diabetes Research: An Overview." Indian Journal Medical Research, Mar. 2007, vol. 125, pp. 451-472.

Standardized Definitions for Cardiovascular Outcomes Trials: Draft Recommendations. Division of Metabolism and Endocrinology Products. Center for Drug Evaluation and Research (CDER). pp 1-34, Mar. 24, 2010.

Tanner J.M., et al., "Standards from Birth to Maturity for Height, Weight, Height Velocity, and Weight Velocity: British Children, Part II," Archives of Disease in Childhood, 1966, vol. 41 (220), pp. 613-635.

The Advance Collaborative Group, "Intensive Blood Glucose Control and Vascular Outcomes in Patients with Type 2 Diabetes." New England Journal of Medicine, Jun. 2008, vol. 358 (24), pp. 2560-2572.

The Criteria Committee of the New York Heart Association, "Nomenclature and Criteria for Diagnosis of Diseases of the Heart and Great Vessels." 9th edition. Boston, Mass: Little, Brown & Co; pp. 253-256 (1994).

Paniker et al., "Beneficial effects of triple drug combination of pioglitazone with glibenclamide and metformin in type 2 diabetes mellitus patients on insulin therapy," J Assoc Physicians India, 51:1061-64 (Nov. 2003).

UK Prospective Diabetes Study (UKPDS) Group, "Tight Blood Pressure Control and Risk of Macrovascular and Microvascular Complications in Type 2 Diabetes (UKPDS 38)," BMJ, Sep. 1998, vol. 317, pp. 703-713.

Weir "Glucagon-like peptide-1 (7-37) actions on endocrine pancreas." Diabetes 38(3):338-42 (Mar. 1989).

WHO, World Health Organization Media Center. Diabetes Fact Sheet. Available from: http://www.who.int/mediacentre/factsheets/fs312/en/index.html. Accessed Jun. 13, 2016, pp. 1-6.

(56) References Cited

OTHER PUBLICATIONS

WHO, World Health Organization Media Center. Obesity and overweight, Fact Sheet No. 311. Updated Jan. 2015, pp. 1-5.
Wikipedia® Entry for "Body Mass Index" Retrieved from the Internet: https://en.wikipedia.org/wiki/Body mass_index, 2016, pp. 1-14, retrieved Feb. 26, 2016.
Wikipedia® Entry for "Metformin" Retrieved from the Internet: https://en.wikipedia.org/wiki/Metformin 2016, pp. 1-21, retrieved Apr. 11, 2016.
Wikipedia® Entry for "Pioglitazone" Retrieved from the Internet: https://en.wikipedia.org/wiki/Pioglitazone 2016, pp. 1-3, retrieved Apr. 11, 2016.
Wikipedia® Entry for "Lixisenatide" Retrieved from the Internet: https://en.wikipedia.org/wiki/Lixisenatidehttps://en.wikipedia.org/wiki/Lixisenatide, pp. 1- 2, updated Dec. 2015.
Wild et al., "Global prevalence of diabetes: estimates for the year 2000 and projections for 2030." Diabetes Care 27 (5):1047-53 (May 2004).
Williams et al., "Macrovascular disease in Diabetes." in handbook of Diabetes. 2nd ed. Williams G, Pickup JC, Eds. Oxford, UK, Blackwell Science pp. 151-58 (1999).
Wiviott et al., "Greater Clinical Benefit of More Intensive Oral Anti platelet Therapy With Prasugrel in Patients With Diabetes Mellitus in the Trial to Assess Improvement in Therapeutic Outcomes by Optimizing Platelet Inhibition With Prasugrei-Thrombolysis in Myocardial Infarction 38," Circulation, 2008, vol. 118 (16), pp. 1626-1636, Oct. 2008; Epub Aug. 31, 2008
Sanofi Press Release entitled "Sanofi Announces Top-Line Results for Cardiovascular Outcomes Study of Lyxumia® (lixisenatide)." dated Mar. 19, 2015, Paris, France, pp. 1-2.
World Health Organisation Report on "Definition and Diagnosis of Diabetes Mellitus and Intermediate Hyperglycemia: Report of a WHO/IDF Consultation," 2006, pp. 1-50.
World Health Organization, "Definition, Diagnosis and Classification of Diabetes Mellitus and its Complications, Part 1: Diagnosis and Classification of Diabetes Mellitus," WHO/NCD/NCS/99.2, Geneva, 1999, pp. 1-66.
Wright et al., U.K. Prospective Diabetes Study Group. "Sulfonylurea inadequacy: efficacy of addition of insulin over years in patients with type 2 diabetes in the UK. Prospective Diabetes Study (UKPDS 57)." Diabetes Care 25 (2):330-36 (Feb. 2002).
Yusuf et al., "Effects of Clopidogrel in Addition to Aspirin in Patients with Acute Coronary Syndromes without ST-Segment Elevation." New England Journal Medical, Aug. 2001, vol. 345 (7), pp. 494-502.
Zealand Pharma Company Announcement "Zealand Pharma, Additional positive results from Global Phase III program with -3-lixisenatide for type 2 diabetes", Apr. 12, 2011, pp. 1- 3, URL, http://files.shareholder.com/downloads/ABEA-58QR0J/0x0x458202/3ccd84a6-5f99-451a-ada0-0a8282da3dad/ZEAL_News_2011_4_12Company_Releases.pdf.
Zimmet et al., "Global and societal implications of the diabetes epidemic." Nature 414(6865):782-87 (Dec. 2001).
Zoungas et al., "Combined Effects of Routine Blood Pressure Lowering and Intensive Glucose Control on Macrovascular and Microvascular Outcomes in Patients With Type 2 Diabetes. New results from the Advance trial." Diabetes Care, 2009, vol. 32(11), pp. 2068-2074, (Nov. 2009; Epub Aug. 3, 2009).
Sillars et al., "Sulphonylurea-metformin combination therapy, cardiovascular disease and all-cause mortality: the Fremantle Diabetes Study." Diabetes Obes Metab. 12(9):757-65 (Sep. 2010).
Werner et al., "The GLP-1 Receptor Agonist AVE0010 Abolishes OGTT-Induced Blood Glucose Excursion in Healthy, Normoglycemic Dog Without Risk of Hypoglycemia" Diabetes 56(Supplement 1):A129 (Jun. 2007). Abstract submitted.
International Search Report by the ISA for International Application No. PCT/EP2016/055267; dated Jun. 7, 2016, pp. 1-7.
U.S. Appl. No. 14/965,586, filed Dec. 10, 2015, Souhami et al.
U.S. Appl. No. 14/995,910, filed Jan. 14, 2016, Bergmann et al.
U.S. Appl. No. 15/073,364, filed Mar. 17, 2016, Belder et al.
U.S. Appl. No. 15/068,286, filed Mar. 13, 2016, Roy et al.
Aguilar, "Heart failure and diabetes: Time to pay attention" American Heart Journal, 162(5):795-97 (Nov. 2011).
Bentley-Lewis et al., "Rationale, design, and baseline characteristics in Evaluation of LIXisenatide in Acute Coronary Syndrome, a long-term cardiovascular end point trial of lixisenatide versus placebo" American Heart Journal, 169(5):631-38 (May 2015; Epub Feb. 11, 2015).
Hubschle et al., "Anti-atherosclerotic activity of lixisenatide in ApoE knockout mice" Abstract 809, Diabetologia, 55 (Supplement 1):S334 (Oct. 2012).
International Search Report by the ISA for International Application No. PCT/EP2016/055267; dated May 20,2 016, pp. 1-7.
Interational Search Report by the ISA for International Application No. PCT/EP2016/055954; dated Sep. 9, 2016, pp. 1-12.
Katz et al., "The clinical burden of type 2 diabetes in patients with acute coronary syndromes: Prognosis and implications for short- and long-term management" Diabetes and Vascular Disease Research, 11 (6):395-409 (Nov. 2014).
Meigs et al., "Body Mass Index, Metabolic Syndrome, and Risk of Type 2 Diabetes or Cardiovascular Disease" Journal of Clinical Endocrinology & Metabolism, 91(8):2906-12 (Aug. 2006).
Partial International Search Report by the ISA for International Application No. PCT/EP2016/055954; dated Jun. 21, 2016, pp. 1-6.
Patel et al., "Stability Considerations for Biopharmaceuticals: Overview of Protein and Peptide Degradation Pathways" Available online at: http://www.bioprocessint.com/manufacturing/formulation/biopharmaceutical-product-stability-considerations-part-1/, 23 pages (2011).
Petersen & Christensen et al., Clinical potential of lixisenatide once daily treatment for type 2 diabetes mellitus Diabetes, Metabolic Syndrome and Obesity: Targets and Therapy, 6:217-31 (Jun. 2013).
Petrie, "The cardiovascular safety of incretin-based therapies: a review of the evidence" Cardiovascular Diabetology, 12(1):130, 12 pages (Sep. 2013).
Ruetten et al., "Protective effects of the GLP-1 receptor agonist lixisenatide on ischaemia-reperfusion-induced myocardial infarction in an isolated rat heart model" Diabetologia, Abstract 810, 54(Supplement 1):S329 (Sep. 2011).
Tirosh et al., "Normal Fasting Plasma Glucose Levels and Type 2 Diabetes in Young Men" New England Journal of Medicine, 353(14):1454-62 (Oct. 2005).
Wohlfart et al., "Cardioprotective effects of lixisenatide in rat myocardial ischemia-reperfusion injury studies" Journal of Translational Medicine, 11(1):84, 12 pages (Mar. 2013).
American Diabetes Association, "Diagnosis and Classification of Diabetes Mellitus", Diabetes Care, 37 (Supplement 1):S81-S90 (Jan. 2014).
American Diabetes Association Annual Scientific Sessions, "New Diabetes Compound AVE0010 Showed Clear Dose Response Results With Once-A-Day Injection in Phase IIb Study", published Jun. 9 2008, two pages.
Dombrowsky & Barrett, "Type II diabetes mellitus in children: Analysis of prevalence based on the pediatric heath information system (PHIS) database" American College of Clinical Pharmacology Annual Meeting, Bethesda, Maryland (Sep. 22-24, 2013).
Giacometti et al., "In vitro activity of the histatin derivative P-113 against multidrug-resistant pathogens responsible for pneumonia in immunocompromised patients." 49(3):1249-52 (Mar. 2005).
Glucophage XR, Product Information, Bristol-Meyers Squibb Company (Jan. 2009).
Lantus® Drug Description, downloaded Nov. 12, 2015, one page.
Miller et al., "Type 2 diabetes in the child and adolescent", In: Lifshitz F (ed) Pediatric Endocrinology: 5th edition, vol. 1, New York, Marcel Dekker, pp. 169-188 (2007).
Raman & Heptulla, "New potential adjuncts to treatment of children with type 1 diabetes mellitus" Pediatric Research, 65(4):370-74 (Apr. 2009).
Rothstein et al., "Anticandida activity is retained in P-113, a 12-amino-acid fragment of histatin 5." Antimicrob Agents Chemother. 45(5):1367-73 (May 2001).
RPMI-1640 Media Formulation, Sigma Aldrich, accessed on Jul. 10, 2016, pp. 1-5.

(56) References Cited

OTHER PUBLICATIONS

Sanofi, "A randomized, double-blind, placebo controlled trial to assess safety, tolerability, pharmacokinetics and pharmacodynamics of lixisentatide in pediatric (10-17 years old) and adult patients with type 2 diabetes", Sanofi, pp. 1-12 (2015). retrieved from the internet: http://en.sanofi.com/img/content/study/PKD11475_summary.pdf (retrieved on Jun. 16, 2015).

Shehadeh et al., "Can GLP-1 preparations be used in children and adolescents with diabetes mellitus?" Pediatric Endocrinology Reviews, 11(3):324-27 (Mar. 2014).

Tanner & Davies, "Clinical longitudinal standards for height and height velocity for North American children." J Pediatr. 107(3):317-29 (Sep. 1985).

Wolever et al., "Second-meal effect: low-glycemic-index foods eaten at dinner improve subsequent breakfast glycemic response" Am J Clin Nutr 48(4):1041-47 (Oct. 1988).

Zeitler et al., "ISPAD Clinical Practice Consensus Guidelines 2014. Type 2 diabetes in the child and adolescent." Pediatr Diabetes 15(Suppl 20):26-46 (Sep. 2014).

Zimmet et al., "The metabolic syndrome in children and adolescents." Lancet 369(9579):2059-61 (Jun. 2007).

Final Office Action issued in U.S. Appl. No. 13/123,835; mailed Nov. 18, 2015, pp. 1-16.

Final Rejection issued in U.S. Appl. No. 13/382,442; mailed Sep. 21, 2016, pp. 1-32.

Non-Final Rejection issued in U.S. Appl. No. 13/509,542; mailed Nov. 23, 2016, pp. 1-34.

Final Rejection in U.S. Appl. No. 13/633,496; mailed Oct. 13, 2016, pp. 1-10.

International Search Report by the ISA for International Application No. PCT/EP2009/000018; dated Jun. 30, 2009, pp. 1-8.

International Search Report by the ISA for International Application No. PCT/EP2016/050804; dated Mar. 4, 2016, pp. 1-4.

Extended European Search Report for European Application No. 14 19 7685; dated Aug. 10, 2015, pp. 1-4.

Extended European Search Report for European Application No. 14 19 7685; dated Oct. 6, 2015, pp. 1-4.

Extended European Search Report for European Application No. 15 15 1488.2; dated Jul. 7, 2015, pp. 1-8.

Bell et al., "Sequence of the human insulin gene." 284(5751):26-32 (Mar. 1980).

Osterbye et al., "Sulfatide promotes the folding of proinsulin, preserves insulin crystals, and mediates its monomerization." Glycobiology 11(6):473-79 (Jun. 2001).

Vilsboll et al., "Liraglutide, a long-acting human glucagon-like peptide-1 analog, given as monotherapy significantly improves glycemic control and lowers body weight without risk of hypoglycemia in patients with type 2 diabetes." Diabetes Care 30(6):1608-10 (Jun. 2007; Epub Mar. 19, 2007).

\* cited by examiner

PHARMACEUTICAL COMPOSITION COMPRISING A GLP-1 AGONIST AND METHIONINE

CROSS-REFERENCE TO RELATED APPLICATIONS

This application is a national stage entry under 35 U.S.C. §371 of International Patent Application No. PCT/EP2010/067249, which claims priority to German Patent Application No. DE102009052832.6, filed Nov. 13, 2009, and to German Patent Application No. 102010011919.9, filed Mar. 18, 2010, all of which are incorporated herein by reference.

The present application relates to a liquid composition comprising a GLP-1 agonist or/and a pharmacologically tolerable salt thereof and, optionally, at least one pharmaceutically acceptable excipient, wherein the composition comprises methionine.

The present application further relates to the composition according to the present invention for treating diabetes mellitus. The present application further relates to the use of a composition according to the present invention in the manufacture of a pharmaceutical for treating diabetes mellitus. The present application further relates to a method for manufacturing a composition according to the present invention, comprising formulating a GLP-1 agonist or/and a pharmacologically tolerable salt thereof with methionine and, optionally, at least one pharmaceutically acceptable excipient. The present application further relates to a method for treating a patient with a composition according to the present invention, comprising administering the composition to the patient.

Customary compositions of GLP-1 compounds comprise a tonicity modifier, a buffer for adjusting the pH, and a preservative.

WO2001/04156 (Zealand Pharmaceuticals) discloses a liquid composition of $Ser^{39}$-exendin-4(1-39)-$NH_2$), sodium dihydrogenphosphate, and preservatives.

WO 2004/035623 (Zealand Pharmaceuticals) discloses a liquid composition comprising a stabilized exendin, 50 mM histidine, 100 to 200 mM sucrose, mannitol or other acceptable sugar, 20 mM methionine, 20 mM asparagine-glutamine or Asp, at a pH of 5.3. Stabilization is effected by certain modifications of the amino acid building blocks of exendin-4(1-39), for example, at positions Gln13, Met14, Trp25, or Asn28.

WO 2005/021022 (Novo Nordisk) discloses a liquid composition comprising acetylated GLP-1, phenol as a preservative, mannitol and glycerol as a tonicity modifier, and, optionally, a buffer.

WO 2006/051110 (Novo Nordisk) discloses liquid compositions comprising liraglutide (GLP-1 compound), poloxamer 188 or poloxamer 407 (Pluronic F-127) as a surface-active substance, phenol, propylene glycol, and sodium phosphate (pH 7.7). Addition of poloxamer-188 or poloxamer-407 led to stabilization.

Exendins are a group of peptides which can lower blood glucose concentrations. Exendins have a certain similarity to the sequence of GLP-1(7-36) (53%, Goke et al. J. Biol Chem 268, 19650-55). Exendin-3 and exendin-4 stimulate an increase in cellular cAMP production in the acinar cells of the guinea pig pancreas by interacting with exendin receptors (Raufman, 1996, Reg. Peptides 61:1-18). Exendin-3, in contrast to exendin-4, effects an increase in the release of amylase in the acinar cells of the pancreas. Exendins act as GLP-1 agonists.

Glucagon-like peptide 1 (GLP-1) is an endocrine hormone which enhances the insulin response following oral intake of glucose or fat. In general, GLP-1 lowers glucagon concentrations, slows gastric emptying, stimulates (pro) insulin synthesis, enhances sensitivity to insulin, and stimulates insulin-independent glycogen synthesis (Hoist (1999), Curr. Med. Chem 6:1005, Nauck et al. (1997) Exp Clin Endocrinol Diabetes 105: 187, Lopez-Delgado et al. (1998) Endocrinology 139:2811). Human GLP-1 has 37 amino acid residues (Heinrich et al., Endocrinol. 115:2176 (1984), Uttenthal et al., J Clin Endocrinol Metabol (1985) 61:472). Active fragments of GLP-1 include GLP-1 (7-36) and GLP-1(7-37).

Exendin-3, exendin-4 and exendin agonists have been proposed for treating diabetes mellitus and preventing hyperglycemia, by reducing gastric motility and gastric emptying (U.S. Pat. No. 5,424,286 and WO98/05351).

Exendin analogs can be characterized by amino acid substitutions and/or C-terminal truncation of the native exendin-4 sequence. Such exendin analogs are described in WO 99/07404, WO 99/25727, and WO 99/25728.

Solid-phase synthesis of AVE0010 is described in WO 01/04156 A1. AVE0010 has the sequence: desPro$^{36}$exendin-4(1-39)-Lys$_6$-$NH_2$. This substance is published as SEQ ID NO:93 in WO 01/04156:

(SEQ ID NO: 1)
H-G-E-G-T-F-T-S-D-L-S-K-Q-M-E-E-E-A-V-R-L-F-I-E-W-L-K-N-G-G-P-S-S-G-A-P-P-S-K-K-K-K-K-K-$NH_2$

Exendin-4 (39 AA) has the sequence:

(SEQ ID NO: 2)
H-G-E-G-T-F-T-S-D-L-S-K-Q-M-E-E-E-A-V-R-L-F-I-E-W-L-K-N-G-G-P-S-S-G-A-P-P-P-S-$NH_2$

Exendin-3 has the sequence (J. Bio. Chem., 267, 1992, 7402-7405):

(SEQ ID NO: 3)
H-His-Ser-Asp-Gly-Thr-Phe-Thr-Ser-Asp-Leu-Ser-Lys-Gln-Met-Glu-Glu-Glu-Ala-Val-

-continued

Arg-Leu-Phe-Ile-Glu-Trp-Leu-Lys-Asn-Gly-Gly-Pro-Ser-Ser-Gly-Ala-Pro-Pro-Pro-Ser-NH₂

GLP-1 has the sequence:

(SEQ ID NO: 4)
H-A-E-G-T-F-T-S-D-V-S-S-Y-L-E-G-Q-A-A-K-E-F-I-A-W-L-V-K-G-R-NH₂

It is an object of the present invention to increase the stability of liquid formulations comprising a GLP-1 agonist. More particularly, it is an object of the present invention to improve physical and chemical integrity. We have found that this object is achieved by formulating the GLP-1 agonist with methionine.

It was found that methionine is able to increase the storage stability of a composition comprising a GLP-1 agonist such as AVE0010. Methionine does not affect the physical integrity of these compositions.

It was found that, surprisingly, the addition of methionine is able to improve the storage stability of a composition according to the present invention by reducing the proportion of oxidation products of methionine, of proteins of high molecular weight, and of total impurities. These parameters are, individually or together, a measure of the chemical integrity of the compositions.

It was further found that, surprisingly, the biological activity of the compositions according to the present invention is increased by the addition of methionine.

The stability of pharmaceutically active polypeptides can be impaired by various mechanisms. These include pH, temperature, light, and the effects of certain constituents.

A range of customary constituents of formulations of GLP-1 agonists can be disadvantageous for the chemical or/and physical integrity and the storage stability of formulations which comprise a GLP-1 agonist. These are, for example, polysorbate 20, polysorbate 80, poloxamer 188, benzalkonium chloride, and lysine. The compositions according to the present invention are therefore preferably free of these constituents.

The present invention accordingly provides for a liquid composition comprising a GLP-1 agonist or/and a pharmacologically tolerable salt thereof and, optionally, at least one pharmaceutically acceptable excipient, wherein the composition comprises methionine.

The composition according to the present invention preferably comprises methionine in an amount ranging from 0.5 mg/mL to 20 mg/mL, more preferably in an amount ranging from 1 mg/mL to 5 mg/mL. Methionine in the D-form can be used. Likewise, methionine in the L-form can be used. Likewise, mixtures of the D-form and the L-form in any desired proportions can be used.

More particularly, the composition according to the present invention is free of surfactants, such as polyols and partial and fatty acid esters and ethers of polyhydric alcohols such as those of glycerol and sorbitol. The compositions according to the present invention are more particularly free of partial and fatty acid esters and ethers of glycerol and sorbitol selected from the group consisting of Span®, Tween®, Myrj®, Brij®, Cremophor®. Furthermore, the compositions according to the present invention are more particularly free of polyols selected from the group consisting of polypropylene glycols, polyethylene glycols, poloxamers, Pluronics, Tetronics. More particularly, the composition according to the present invention is free of at least one substance selected from the group consisting of polysorbate, polysorbate and poloxamer.

More particularly, the composition according to the present invention is substantially free, preferably free, of polysorbate, such as, for example, polysorbate 20.

More particularly, the composition according to the present invention is substantially free, preferably free, of polysorbate 80.

More particularly, the composition according to the present invention is substantially free, preferably free, of poloxamer, such as, for example, poloxamer 188.

More particularly, the composition according to the present invention is substantially free, preferably free, of benzalkonium chloride.

More particularly, the composition according to the present invention is substantially free, preferably free, of histidine.

More particularly, the composition according to the present invention is substantially free, preferably free, of EDTA, more particularly sodium EDTA.

The composition according to the present invention can comprise one or more substances which are customarily used to buffer the pH (buffer substances).

Examples of such buffer substances are acetate, citrate, and phosphate, for example, in amounts of up to 5 mg/ml, up to 4 mg/ml, up to 3 mg/ml, or up to 2 mg/ml.

The composition according to the present invention can, likewise, be substantially free of buffer substances. Likewise, the composition according to the present invention can be free of buffer substances.

The composition according to the present invention can be substantially free of citrate, acetate, and/or phosphate, or else free of citrate, acetate, and/or phosphate.

More particularly, the composition according to the present invention is substantially free, preferably free, of histidine and sodium EDTA.

More particularly, no insulin is present in the composition according to the present invention.

The pharmaceutical composition of the present invention can have an acidic or physiological pH. An acidic pH range is preferably in the range of pH 1-6.8, pH 3.5-6.8, or pH 3.5-5. A physiological pH is preferably in the range of pH 2.5-8.5, more preferably pH 4.0 to 8.5, even more preferably pH 4.0 to 6.0. Especially preferred is a pH of approximately 4.5. For pH adjustment, physiologically safe dilute acids (typically HCl) and alkalis (typically NaOH) are suitable.

The composition according to the present invention can comprise a suitable preservative. Suitable preservatives are, for example, phenol, m-cresol, benzyl alcohol, and/or p-hydroxybenzoate esters. m-Cresol is preferred.

Furthermore, the composition according to the present invention can comprise suitable tonicity modifiers. Suitable tonicity modifiers are, for example, glycerol, dextrose, lactose, sorbitol, mannitol, glucose, NaCl, calcium or magnesium compounds such as $CaCl_2$ etc. The concentrations of glycerol, dextrose, lactose, sorbitol, mannitol, and glucose are customarily in the range of 100-250 mM, NaCl in a concentration of up to 150 mM. Glycerol is preferred.

More particularly, the composition is intended for parenteral administration. The composition according to the present invention is preferably an injectable composition, more preferably for subcutaneous injection. More particularly, the composition of the present invention is suitable for injection once a day.

More particularly, the formulation according to the present invention has, after storage for 1 month, 2 months, 4 months, or 6 months at a temperature of +5° C. or 25° C., an activity of at least 80%, at least 90%, at least 95%, or at least 98% of the activity at the start of storage.

In the present application, "activity" means the activity of the GLP-1 agonist which is used in the formulation according to the present invention. Methods for determining the activity of a GLP-1 agonist are known to a person skilled in the art.

Preferably, the composition according to the present invention has a biological activity of GLP-1 agonist of at least 89% or at least 90% after storage for 6 months at 25° C. The composition according to the present invention preferably has a biological activity of GLP-1 agonist of at least 45% or at least 50% after storage for 6 months at 40° C.

More particularly, the formulation according to the present invention exhibits chemical integrity after storage for 1 month, 2 months, 3 months, 4 months, or 6 months. Chemical integrity means, more particularly, that after storage at a temperature of +5° C., 25° C., or 40° C. the formulation comprises at least 80%, at least 90%, at least 95%, or at least 98% of the active substance, compared with the start of storage, in a substantially chemically unchanged form.

Chemical integrity can mean the chemical integrity of the GLP-1 agonist. GLP-1 agonists may comprise a methionine residue (e.g. position 14 in AVE0010). Chemical integrity of the GLP-1 agonist means, more particularly, that oxidation of the methionine residue is prevented. Here, chemical integrity means, more particularly, that the proportion of oxidized methionine with respect to the entire methionine content of the GLP-1 agonist after storage for 1, 2, 3, 4, or 6 months is below 0.7%, below 0.6%, below 0.5%, below 0.4%, or below 0.3%. Storage can be effected, for example, at 5° C., 25° C., or 40° C. Storage for 6 months at 5° C. is preferred, in which case the proportion of oxidized methionine is below 0.3%. Likewise, storage for 6 months at 25° C. is preferred, in which case the proportion of oxidized methionine is below 0.7%, below 0.6%, below 0.5%, below 0.4%, or below 0.3%. Likewise, storage for 6 months at 40° C. is preferred, in which case the proportion of oxidized methionine is below 1%, below 0.7%, below 0.6%, below 0.5%, below 0.4%, or below 0.3%.

Chemical integrity can mean a very low proportion of total impurities in the formulation according to the present invention. The proportion of total impurities with respect to the entire mass of the GLP-1 agonist present in the formulation after storage for 6 months at 40° C. is more particularly below 50%, below 10% after storage at 25° C., or/and below 1.8% after storage at 5° C.

Chemical integrity can mean a very low proportion of proteins of high molecular weight in the formulation according to the present invention. The proportion of proteins of high molecular weight with respect to the entire mass of the GLP-1 agonist present in the formulation after storage for 6 months at 40° C. is more particularly below 5%, below 4%, below 3%, or below 2%. After storage for 6 months at 25° C., the proportion of proteins of high molecular weight with respect to the entire mass of the GLP-1 agonist present in the formulation is more particularly below 0.8%, below 0.7%, or below 0.6%.

More particularly, the formulation according to the present invention exhibits physical integrity after storage for 1 month, 2 months, 4 months, or 6 months. Physical integrity means, more particularly, that after storage at a temperature of +5° C., 25° C., or 40° C. the formulation comprises at least 80%, at least 90%, at least 95%, or at least 98% of the active substance, compared with the start of storage, in a substantially physically unchanged form.

Physical integrity can mean the integrity of the GLP-1 agonist. Physical integrity means, more particularly, that the GLP-1 agonist does not form aggregates, such as, for example, fibrils.

The GLP-1 agonist is preferably selected from the group consisting of exendin-3 and analogs and derivates thereof, exendin-4 and analogs and derivates thereof, and in which case the GLP-1 agonist is more preferably selected from the group consisting of AVE0010 and exendin-4.

Exendin-3, analogs and derivates of exendin-3, exendin-4, and analogs and derivates of exendin-4 can be found in WO 01/04156, WO 98/30231, U.S. Pat. No. 5,424,286, EP application 99 610043.4, and WO 2004/005342. These documents are incorporated herein by reference. The exendin-3, exendin-4, and analogs and derivates thereof described in these documents can be synthesized by means of the methods described therein, after which modifications are optionally carried out.

The sequences of AVE0010 (SEQ ID NO:1), exendin-4 (SEQ ID NO:2), and exendin-3 (SEQ ID NO:3) show a high degree of similarity. The sequences of AVE0010 and exendin-4 are identical at positions 1-37. Sequence 1-39 from exendin-4 is at 37 of the 39 positions (94%) identical to the exendin-3 sequence at positions 48-86. With reference to the sequences, a person skilled in the art can readily convert the positions specified herein, which relate to a particular sequence (e.g. to the sequence of AVE0010 or exendin-4), to other sequences.

Analogs and derivates of exendin-3 or/and exendin-4 contain more particularly a modified amino acid sequence. For example, single amino acids can be deleted (e.g. desPro36, desPro37, desAsp28, desMet(O)14 in exendin-4 and the corresponding positions in exendin-3). Likewise, single positions can be substituted (e.g. Met(O)$^{14}$, Trp(O$_2$)$^{25}$, IsoAsp$^{28}$, Asp$^{28}$ Pro$^{38}$ in exendin-4 and the corresponding positions in exendin-3), in which case unnatural amino acids such as Met(O) (methionine sulfoxide or methionine sulfone), Trp(O$_2$) (N-formylkynurenine), or/and IsoAsp (β-aspartate or isoaspartate) can also be used. Unnatural amino acids can be readily inserted, in the form of corresponding amino acid building blocks, into the sequence.

Furthermore, the C-terminus or/and the N-terminus can be modified, for example, by an additional sequence such as -(Lys)-, -(Lys)$_2$-, -(Lys)$_3$-, -(Lys)$_4$-, -(Lys)$_5$-, -(Lys)$_6$-, -Asn-(Glu)$_5$-, in which case -(Lys)$_4$-, -(Lys)$_5$-, -(Lys)$_6$-, -Asn-(Glu)$_5$- are preferred. The carboxyl group at the C-terminus is preferably modified to an amide group (—NH$_2$). Optionally, modification of the C-terminus or/and of the N-terminus is carried out as a further step after completion of synthesis.

Pharmaceutically tolerable salts can be manufactured in a further step after completion of the synthesis cycles of the method according to the present invention. The manufacture of pharmaceutically tolerable salts of peptides is known to a person skilled in the art. A preferred pharmaceutically tolerable salt is acetate.

The GLP-1 agonist is preferably selected from the group consisting of exendin-4, analogs and derivates of exendin-4, and pharmacologically tolerable salts thereof.

A further preferred GLP-1 agonist is an analog of exendin-4 selected from the group consisting of:
H-desPro$^{36}$-exendin-4-Lys$_6$-NH$_2$,
H-des(Pro$^{36,37}$)-exendin-4-Lys$_4$-NH$_2$,
H-des(Pro$^{36,37}$)-exendin-4-Lys$_5$-NH$_2$ and pharmacologically tolerable salts thereof.

A further preferred GLP-1 agonist is an analog of exendin-4 selected from the group consisting of:
desPro$^{36}$[Asp$^{28}$]exendin-4 (1-39),
desPro$^{36}$[IsoAsp$^{28}$]exendin-4 (1-39),
desPro$^{36}$[Met(O)$^{14}$,Asp$^{28}$]exendin-4 (1-39),
desPro$^{36}$[Met(O)$^{14}$,IsoAsp$^{28}$]exendin-4 (1-39),
desPro$^{36}$[Trp(O$_2$)$^{26}$,Asp$^{28}$]exendin-2 (1-39),
desPro$^{36}$[Trp(O$_2$)$^{25}$,IsoAsp$^{28}$]exendin-2 (1-39),
desPro$^{36}$[Met(O)$^{14}$Trp(O$_2$)$^{26}$,Asp$^{28}$]exendin-4 (1-39),
desPro$^{36}$[Met(O)$^{14}$Trp(O$_2$)$^{25}$,IsoAsp$^{28}$]exendin-4(1-39) and pharmacologically tolerable salts thereof.

A further preferred GLP-1 agonist is an analog of exendin-4 selected from a group as described in the previous paragraph, wherein the peptide -Lys$_6$-NH$_2$ is attached to the C-termini of the analogs of exendin-4.

A further preferred GLP-1 agonist is an analog of exendin-4 selected from the group consisting of:
H-(Lys)$_6$-desPro$^{36}$[Asp$^{28}$]exendin-4(1-39)-Lys$_6$-NH$_2$,
desAsp$^{28}$Pro$^{36}$,Pro$^{37}$,Pro$^{38}$exendin-4(1-39)-NH$_2$,
H-(Lys)$_6$-desPro$^{36}$,Pro$^{37}$,Pro$^{38}$[Asp$^{28}$]exendin-4(1-39)-NH$_2$,
H-Asn-(Glu)$_5$desPro$^{36}$,Pro$^{37}$,Pro$^{38}$[Asp$^{28}$]exendin-4(1-39)-NH$_2$,
desPro$^{36}$,Pro$^{37}$,Pro$^{38}$[Asp$^{28}$]exendin-4(1-39)-(Lys)$_6$-NH$_2$,
H-(Lys)$_6$-desPro$^{36}$,Pro$^{37}$,Pro$^{38}$[Asp$^{28}$]exendin-4(1-39)-(Lys)$_6$-NH$_2$,
H-Asn-(Glu)$_5$-desPro$^{36}$,Pro$^{37}$,Pro$^{38}$[Asp$^{28}$]exendin-4(1-39)-(Lys)$_6$-NH$_2$,
H-(Lys)$_6$-desPro$^{36}$[Trp(O$_2$)$^{26}$,Asp$^{28}$]exendin-4(1-39)-Lys$_6$-NH$_2$,
H-desAsp$^{28}$ Pro$^{36}$,Pro$^{37}$,Pro$^{38}$[Trp(O$_2$)$^{25}$]exendin-4(1-39)-NH$_2$,
H-(Lys)$_6$-desPro$^{36}$,Pro$^{37}$,Pro$^{38}$[Trp(O$_2$)$^{25}$,Asp$^{28}$]exendin-4(1-39)-NH$_2$,
H-Asn-(Glu)$_5$-desPro$^{36}$,Pro$^{37}$,Pro$^{38}$[Trp(O$_2$)$^{26}$,Asp$^{28}$]exendin-4(1-39)-NH$_2$,
desPro$^{36}$,Pro$^{37}$,Pro$^{38}$[Trp(O$_2$)$^{26}$,Asp$^{28}$]exendin-4(1-39)-(Lys)$_6$-NH$_2$,
H-(Lys)$_6$-desPro$^{36}$,Pro$^{37}$,Pro$^{38}$[Trp(O$_2$)$^{25}$,Asp$^{28}$]exendin-4(1-39)-(Lys)$_6$-NH$_2$,
H-Asn-(Glu)$_5$-desPro$^{36}$,Pro$^{37}$,Pro$^{38}$[Trp(O$_2$)$^{26}$,Asp$^{28}$]exendin-4(1-39)-(Lys)$_6$-NH$_2$,
H-(Lys)$_6$-desPro$^{36}$[Met(O)$^{14}$,Asp$^{28}$]exendin-4(1-39)-Lys$_6$-NH$_2$,
desMet(o)$^{14}$Asp$^{28}$Pro$^{36}$,Pro$^{37}$,Pro$^{38}$exendin-4(1-39)-NH$_2$,
H-(Lys)$_6$-desPro$^{36}$,Pro$^{37}$,Pro$^{38}$[Met(O)$^{14}$,Asp$^{28}$]exendin-4(1-39)-NH$_2$,
H-Asn-(Glu)$_5$-desPro$^{36}$,Pro$^{37}$,Pro$^{38}$[Met(O)$^{14}$,Asp$^{28}$]exendin-4(1-39)-NH$_2$,
desPro$^{36}$,Pro$^{37}$,Pro$^{38}$[Met(O)$^{14}$,Asp$^{28}$]exendin-4(1-39)-(Lys)$_6$-NH$_2$,
H-(Lys)$_6$-desPro$^{36}$,Pro$^{37}$,Pro$^{38}$[Met(O)$^{14}$,Asp$^{28}$]exendin-4(1-39)-Lys$_6$-NH$_2$,
H-Asn-(Glu)$_5$-desPro$^{36}$,Pro$^{37}$,Pro$^{38}$[Met(O)$^{14}$,Asp$^{28}$]exendin-4(1-39)-(Lys)$_6$-NH$_2$,
H-(Lys)$_6$-desPro$^{36}$[Met(O)$^{14}$, Trp(O$_2$)$^{28}$,Asp$^{28}$]exendin-4(1-39)-Lys$_6$-NH$_2$,
desAsp$^{28}$Pro$^{36}$,Pro$^{37}$,Pro$^{38}$[Met(O)$^{14}$, Trp(O$_2$)$^{28}$]exendin-4(1-39)-NH$_2$,
H-(Lys)$_6$-desPro$^{36}$,Pro$^{37}$,Pro$^{38}$[Met(O)$^{14}$, Trp(O$_2$)$^{25}$,Asp$^{28}$]exendin-4(1-39)-NH$_2$,
H-Asn-(Glu)$_5$-desPro$^{36}$,Pro$^{37}$,Pro$^{38}$[Met(O)$^{14}$,Asp$^{28}$]exendin-4(1-39)-NH$_2$,
desPro$^{36}$,Pro$^{37}$,Pro$^{38}$[Met(O)$^{14}$, Trp(O$_2$)$^{25}$,Asp$^{28}$]exendin-4(1-39)-(Lys)$_6$-NH$_2$,
H-(Lys)$_6$-desPro$^{36}$,Pro$^{37}$,Pro$^{38}$[Met(O)$^{14}$,Trp(O$_2$)$^{28}$,Asp$^{28}$]exendin-4(1-39)-(Lys)$_6$-NH$_2$,
H-Asn-(Glu)$_5$-desPro$^{36}$, Pro$^{37}$, Pro$^{38}$[Met(O)$^{14}$,Trp(O$_2$)$^{28}$, Asp$^{28}$]exendin-4(1-39)-(Lys)$_6$-NH$_2$ and pharmacologically tolerable salts thereof.

Likewise, the GLP-1 agonist can be selected from the group consisting of GLP-1 and analogs and derivates of GLP-1. A further preferred GLP-1 agonist is selected from the group consisting of Arg$^{34}$,Lys$^{26}$(N$^\epsilon$(γ-glutamyl(N$^\alpha$-hexadecanoyl)))GLP-1(7-37)[liraglutide] and a pharmacologically tolerable salt thereof.

A further preferred GLP-1 agonist is AVE0010. AVE0010 has the sequence desPro$^{36}$exendin-4(1-39)-Lys$_6$-NH$_2$ (SEQ ID NO:1). Likewise, pharmacologically tolerable salts of AVE0010 are preferred.

The GLP-1 agonist, for example AVE0010, is more particularly used in an amount ranging from 0.01 mg/ml to 0.5 mg/ml or 0.05 mg/ml to 1.5 mg/ml.

In a particular embodiment, the formulation according to the present invention comprises the following constituents:
(a) desPro$^{36}$exendin-4(1-39)-Lys$_6$-NH$_2$ (e.g. approximately 0.1 mg/mL),
(b) sodium acetate trihydrate (approximately 3.5 mg/mL),
(c) m-cresol (approximately 2.7 mg/mL),
(d) L-methionine (approximately 3 mg/mL),
(e) 85% glycerol (approximately 18 mg/mL),
(f) approximately 0.1 N hydrochloric acid, if adjustment to a pH of approximately 4.5 is required,
(g) approximately 0.1 N NaOH solution, if adjustment to a pH of approximately 4.5 is required, and
(h) water.

More particularly, the formulation according to the present invention consists of the constituents mentioned in (a) to (h).

In the present application, "approximately" means that the constituents can be present, for example, within the ranges of ±10, ±20, or ±30% around the specified values in the compositions according to the present invention.

If the composition according to the present invention comprises more than one GLP-1 agonist, then these GLP-1 agonists are selected independently of one another.

Suitable packaging for the composition according to the present invention is, for example, a syringe or a glass vessel with a suitable closure, from which individual therapeutically effective doses can be withdrawn as needed. Equally suitable are injection pens for administering doses; such pens comprise a container (e.g. a cartridge) which contains a pharmaceutical composition according to the present invention.

The present invention further provides for a method for treating a patient with a composition according to the present invention, comprising administering the composition to the patient.

The composition according to the present invention is intended more particularly for treating diabetes mellitus, more particularly for treating type I or type II diabetes mellitus. Further possible indications are symptoms which are associated with diabetes mellitus. Preferably, the composition according to the present invention is used to control the fasting, postprandial, or/and postabsorptive plasma glucose concentration, to improve glucose tolerance, to prevent hypoglycemia, to prevent functional loss of the β-cells of the pancreas, to effect weight loss, or/and to prevent weight gain.

The present invention further provides for the use of a composition according to the present invention in the manufacture of a pharmaceutical for treating diabetes mellitus, more particularly type I or type II, or/and the symptoms associated with it, as described herein.

The present invention further provides a method for manufacturing a composition according to the present invention, comprising formulating a GLP-1 agonist or/and a pharmacologically tolerable salt thereof with methionine and, optionally, at least one pharmaceutically acceptable excipient.

The present invention further provides for the use of the composition according to the present invention together with the administration of metformin, sulfonylurea, or glitazones, a long-acting insulin/insulin derivate, and/or a combination thereof, more particularly as an add-on therapy in the administration of metformin.

The present invention further provides for the use of the composition according to the present invention in patients whose blood sugar levels cannot be controlled sufficiently by the administration of metformin, sulfonylurea, or glitazones, a long-acting insulin/insulin derivate, and/or a combination thereof.

The present invention further provides for the use of the composition according to the present invention in patients with type II diabetes as a supplement to a diet in order to improve blood sugar control.

More particularly, the composition comprises desPro$^{36}$ exendin-4(1-39)-Lys$_6$-NH$_2$ (AVE0010), liraglutide and/or a pharmacologically tolerable salt together with methionine and/or a pharmacologically tolerable salt.

More particularly, Lantus®, N$^{\epsilon B29}$-tetradecanoyl des (B30) human insulin, or Insuman® is useful as a long-acting insulin derivative.

Especially preferred is the add-on therapy with metformin and/or a long-acting insulin/insulin derivate and/or a pharmacologically tolerable salt thereof for treating type II diabetes and/or obesity, more particularly in patients who are younger than 50 years and/or have a body mass index of at least 30.

In the present invention, the add-on therapy involves more particularly the treatment of type II diabetes with metformin and AVE0010. Metformin and AVE0010 can be administered in a time interval of 24 hours. Metformin and AVE0010 can each be administered in a once-a-day dosage. Metformin and AVE0010 can be administered by means of different routes of administration. Metformin can be administered orally, AVE0010 subcutaneously.

Patients treated with the add-on therapy according to the present invention can have an HbA1c value in the range of 7% to 10%. They are preferably in the age range of 18 to 50 years.

The use in the add-on therapy according to the present invention is more particularly applicable to patients in whom type II diabetes cannot be sufficiently controlled with metformin alone.

More particularly, metformin is administered as follows: at least 1.0 g/day, preferably at least 1.5 g/day for 3 months.

The invention is further elucidated by the following examples and figures.

BRIEF DESCRIPTION OF THE DRAWINGS

FIG. 1: batch 894. FIG. 2: batch 897.

FIG. 3: batch 894. FIG. 4: batch 897.

FIG. 5: batch 894. FIG. 6: batch 897.

EXAMPLE 1

Liquid Composition Comprising AVE0010 and Methionine

Figure 1:
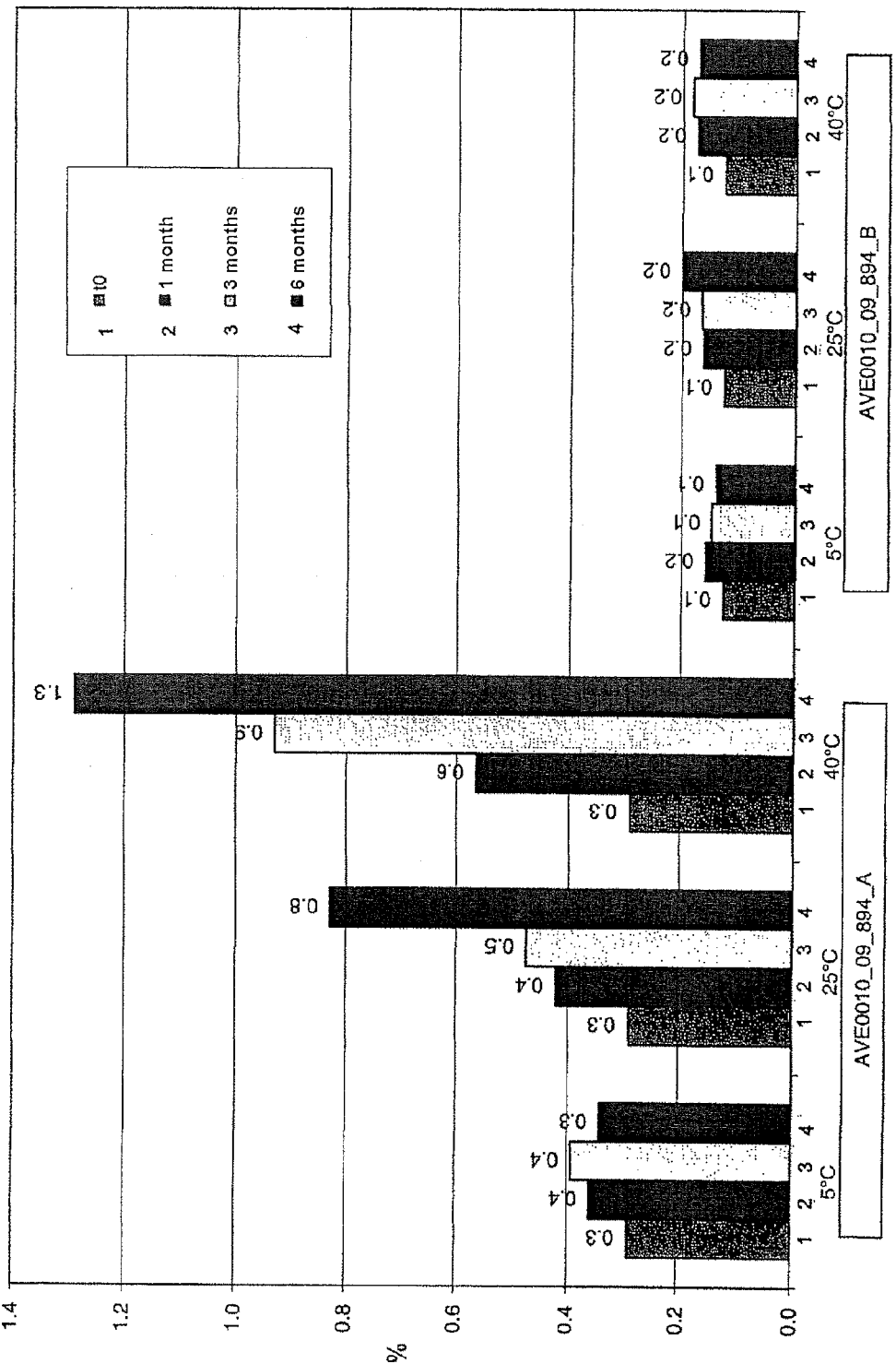
FIGS. 1 and 2 show the percentage content of oxidized methionine Met(ox) with respect to the entire methionine content of AVE0010 after storage at different temperatures. 1: start of storage t0. 2: storage for 1 month. 3: storage for 3 months. 3: storage for 6 months.

The purpose of the study is the evaluation of the chemical or/and physical stability of formulations of AVE0010 (solution for injection, 0.1 mg/ml) with and without methionine, when the product is stored in cartridges under long-term conditions and accelerated conditions for up to 6 months.

The following compositions are tested:

| Composition A (2 parallel batches: AVE0010_09_894_A and AVE0010_09_897_A) | | |
|---|---|---|
| Substance | Specification according to pharmacopeia | Amount per unit |
| AVE0010 | Sanofi-Aventis | 0.10 mg |
| Sodium acetate trihydrate | Ph. Eur./USP | 3.50 mg |
| m-Cresol | Ph. Eur./USP | 2.70 mg |
| 85% Glycerol | Ph. Eur./USP | 18.00 mg |
| 0.1N Hydrochloric acid | Ph. Eur./USP | ad pH 4.5 |
| 0.1N NaOH solution | Ph. Eur./USP | ad pH 4.5 |
| Water for injection (WfI) | Ph. Eur./USP | ad 1.0 ml |

| Composition B (2 parallel batches: AVE0010_09_894_B and AVE0010_09_897_B) | | |
|---|---|---|
| Substance | Specification according to pharmacopeia | Amount per unit |
| AVE0010 | Sanofi-Aventis | 0.10 mg |
| Sodium acetate trihydrate | Ph. Eur./USP | 3.50 mg |
| m-Cresol | Ph. Eur./USP | 2.70 mg |
| L-Methionine | Ph. Eur./USP | 3.00 mg |
| 85% Glycerol | Ph. Eur./USP | 18.00 mg |
| 0.1N Hydrochloric acid | Ph. Eur./USP | ad pH 4.5 |
| 0.1N NaOH solution | Ph. Eur./USP | ad pH 4.5 |
| Water for injection (WfI) | Ph. Eur./USP | ad 1.0 ml |

The formulations are stored in units which are intended for clinical studies and for sales and distribution.

| Term | Description |
|---|---|
| Cartridge for injection pen | Cartridge, 3 ml colorless, type I glass (Ph. Eur.), SAP number 100922 |
| Crimped lid and inserted within a gray sealing disk | 7.5 mm<br>Crimped lid: aluminum<br>Sealing disk (exterior): isoprene rubber, material number 7773/35 |

-continued

| Term | Description |
|---|---|
| | Sealing disk (interior): bromobutyl rubber, material number 4780/40 Type I closure (Ph. Eur./USP) SAP number 164571 |
| Plunger | 9.2 × 11 mm Bromobutyl rubber, black SAP number 120521 |

Storage times, storage conditions, time points are summarized in the following table.

| | Test interval (months) | | | |
|---|---|---|---|---|
| Condition | 0 | 1 | 3 | 6 |
| Long-term storage | | | | |
| +5 ± 3° C. | x | x | x | x |
| Accelerated conditions (temperature, humidity) | | | | |
| +25 ± 2° C./60 ± 5% RH | | x | x | x |
| +40 ± 2° C./75 ± 5% RH | | x | x | x |

The formulations are stored horizontally. RH means relative humidity. Time point 0 is the start of storage. The measurements at time point 0 are used as a reference for all conditions tested. During the tests, the samples are stored at +5±3° C.

The physical and chemical stability of the stored formulations is determined with the help of the following tests:
Description
Clarity of the solution and color thereof
pH
Chemical stability (purity and impurities, determined by HPLC, more particularly the proportion of oxidation products and of total impurities)
Proteins of high molecular weight, determined by HPSEC
Visible particles
Biological activity of the formulations Results The formulations were studied separately for the parallel batches (894 and 897) with regard to the following parameters:
Biological activity of AVE0010. At 5° C. and 25° C., activity after 6 months was at least 96% of initial activity. The activities of the compositions according to the present invention were greater than the activities of the comparative compositions. At 40° C., activity after 6 months in the absence of methionine was approximately 43%. In the presence of methionine, activity was approximately 51% and thus clearly greater than in the absence of methionine.

Figure 2:
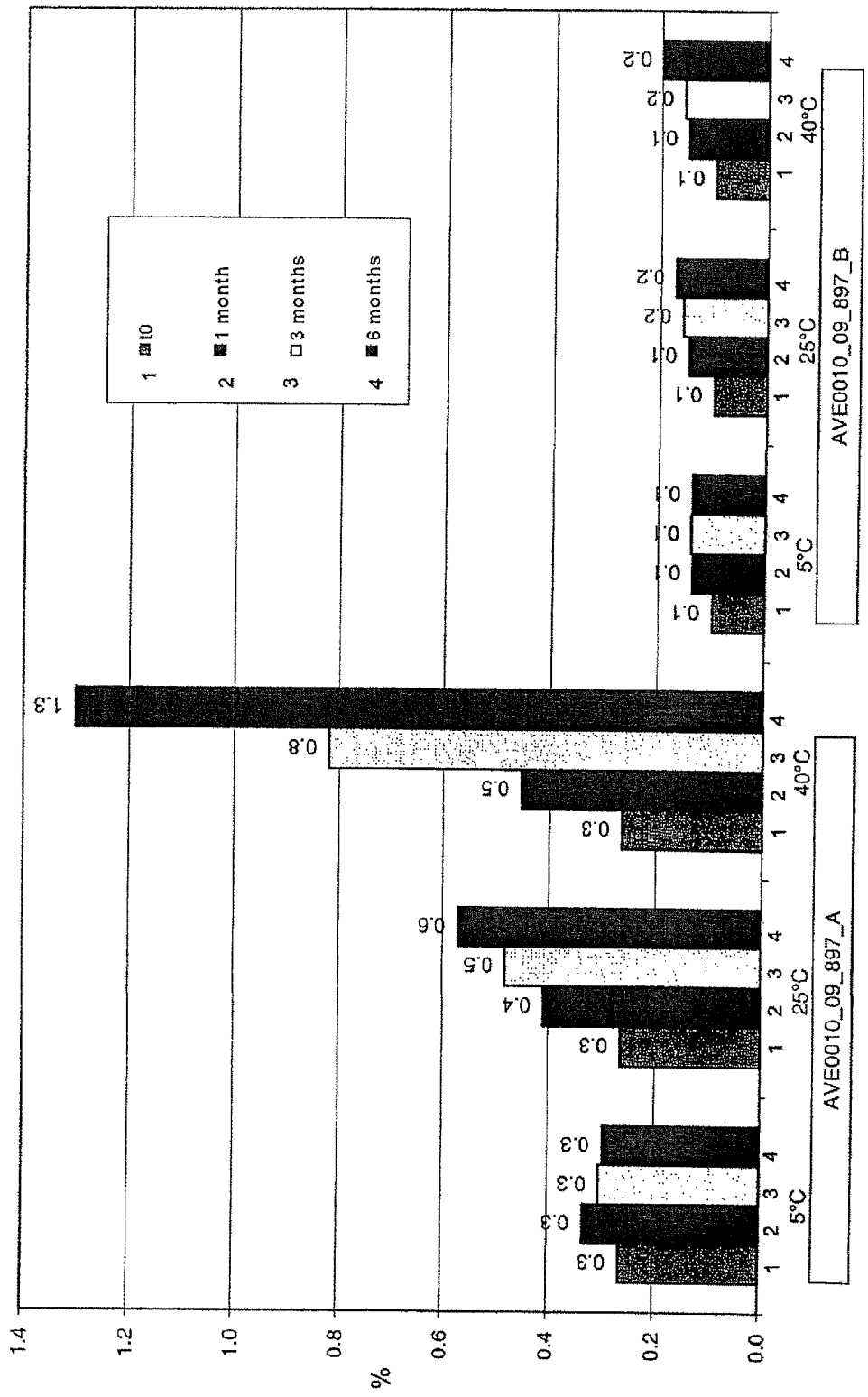

Oxidation products. Measurements were carried out on an HPLC instrument (model: alliance) from Water Systems, using the 100% peak area method. For separation, a gradient of 0.1% TFA and acetonitrile as the mobile phase and a C18 reversed-phase column (Jupiter) as the stationary phase were used. At 5° C., the proportion of oxidized methionine Met(ox) in AVE0010 in the absence of methionine was 0.3%. At 25° C., the proportion was in the range of 0.6-0.8%, at 40° C. 1.3%. When the formulation comprised methionine, the proportion of oxidized methionine was distinctly lower. It was never more than 0.2% under all conditions tested. At 25° C., the proportion was thus approximately only ¼ to ⅓ of the content in the absence of methionine, even at 40° C. approximately only ⅙ (see FIGS. 1 and 2).

Figure 3:
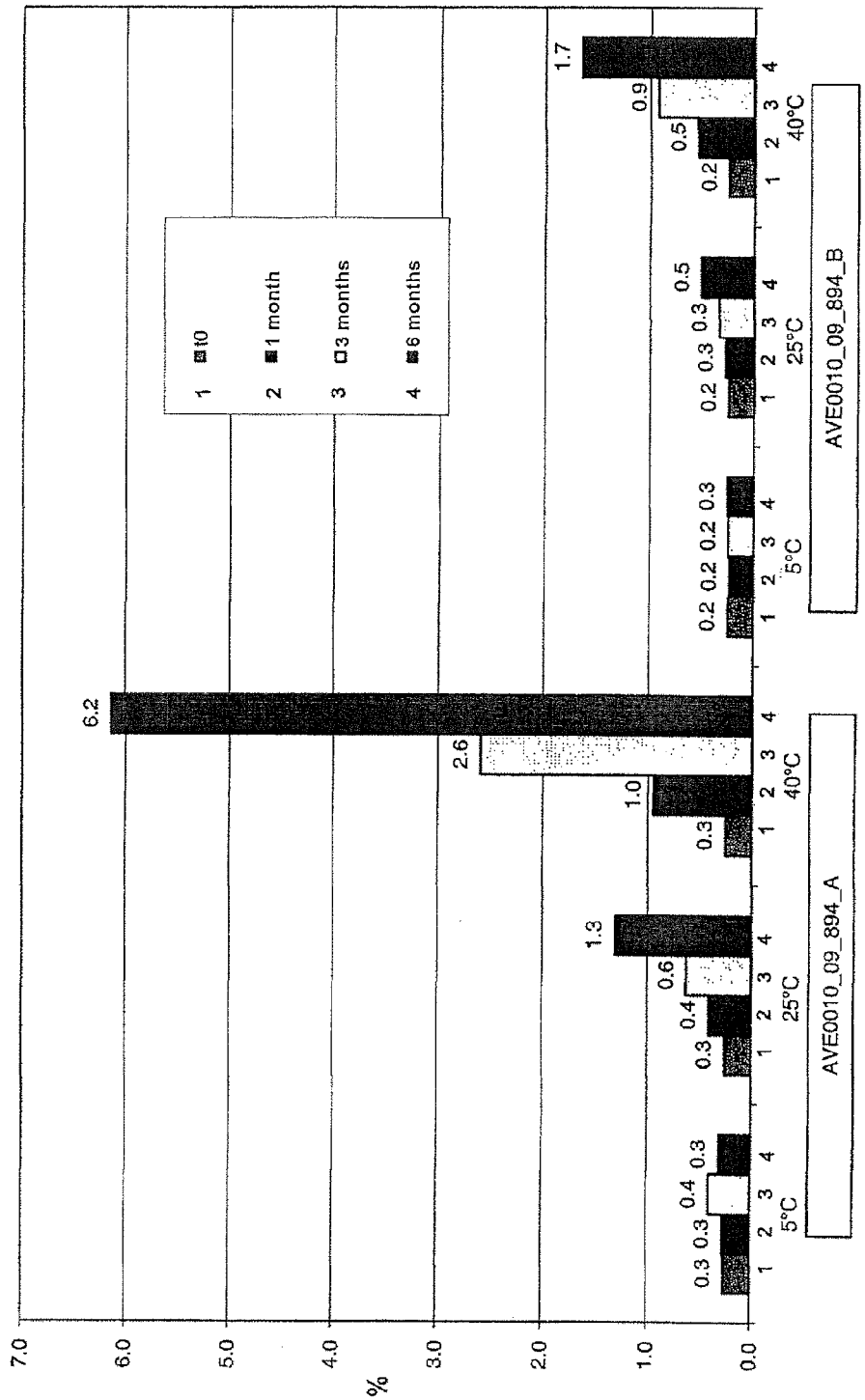
FIGS. 3 and 4 show the percentage content of protein impurities of high molecular weight (with respect to AVE0010) after storage at different temperatures. 1: start of storage t0. 2: storage for 1 month. 3: storage for 3 months. 3: storage for 6 months.
Figure 4:
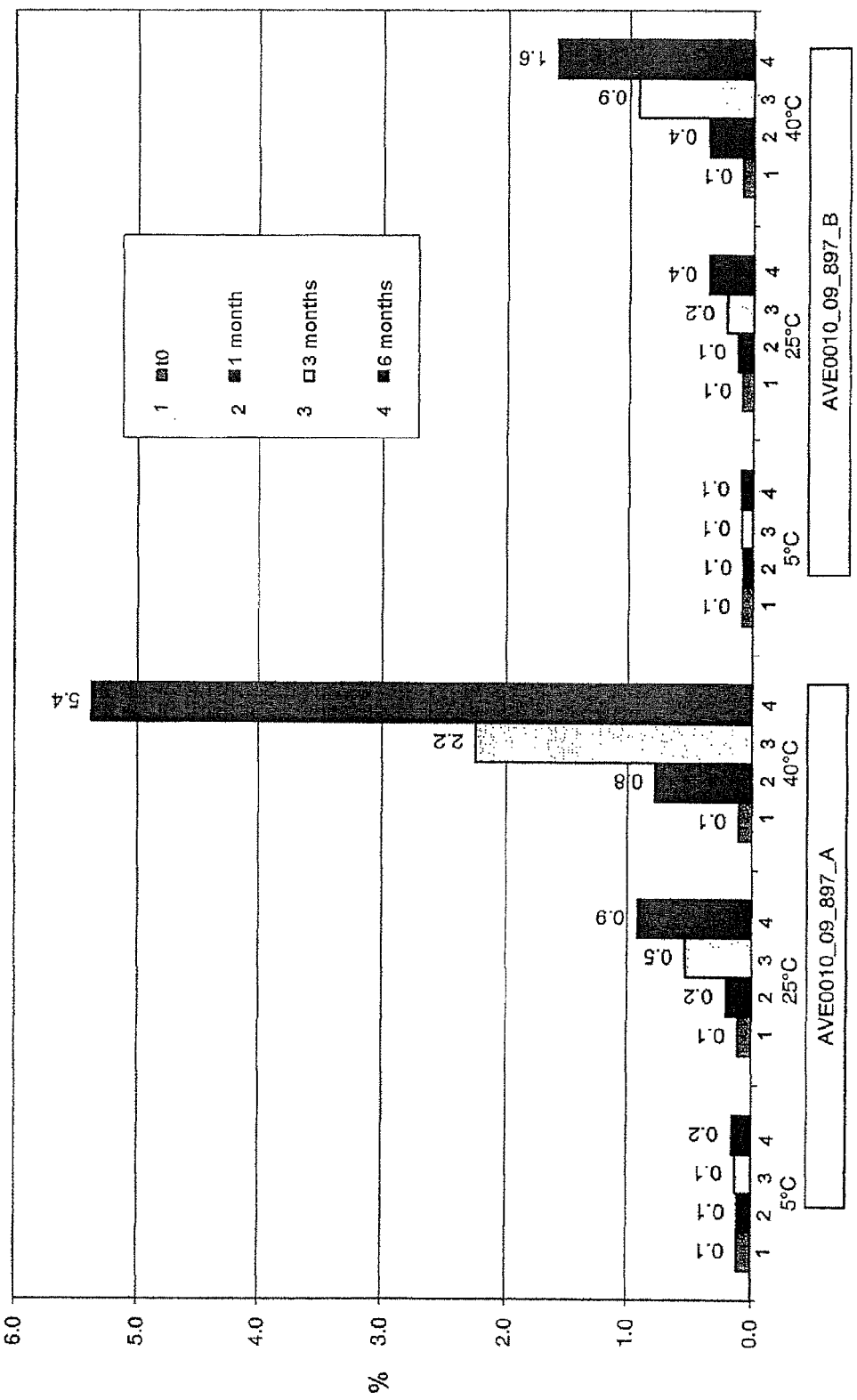

Proteins of high molecular weight. At 5° C., the proportion was between 0.1 and 0.3% and remained substantially unchanged during the entire storage time. At 25° C., the proportion rose in the absence of methionine to 0.9 and 1.3%, respectively. In the presence of methionine, the proportion was 0.4 to 0.5% and thus less than half as high. At 40° C., the proportion was in the absence of methionine 5.4% and 6.2%, respectively, while it was in the presence of methionine only 1.6 and 1.7%, respectively, and thus clearly lower (see FIGS. 3 and 4).

Figure 5:
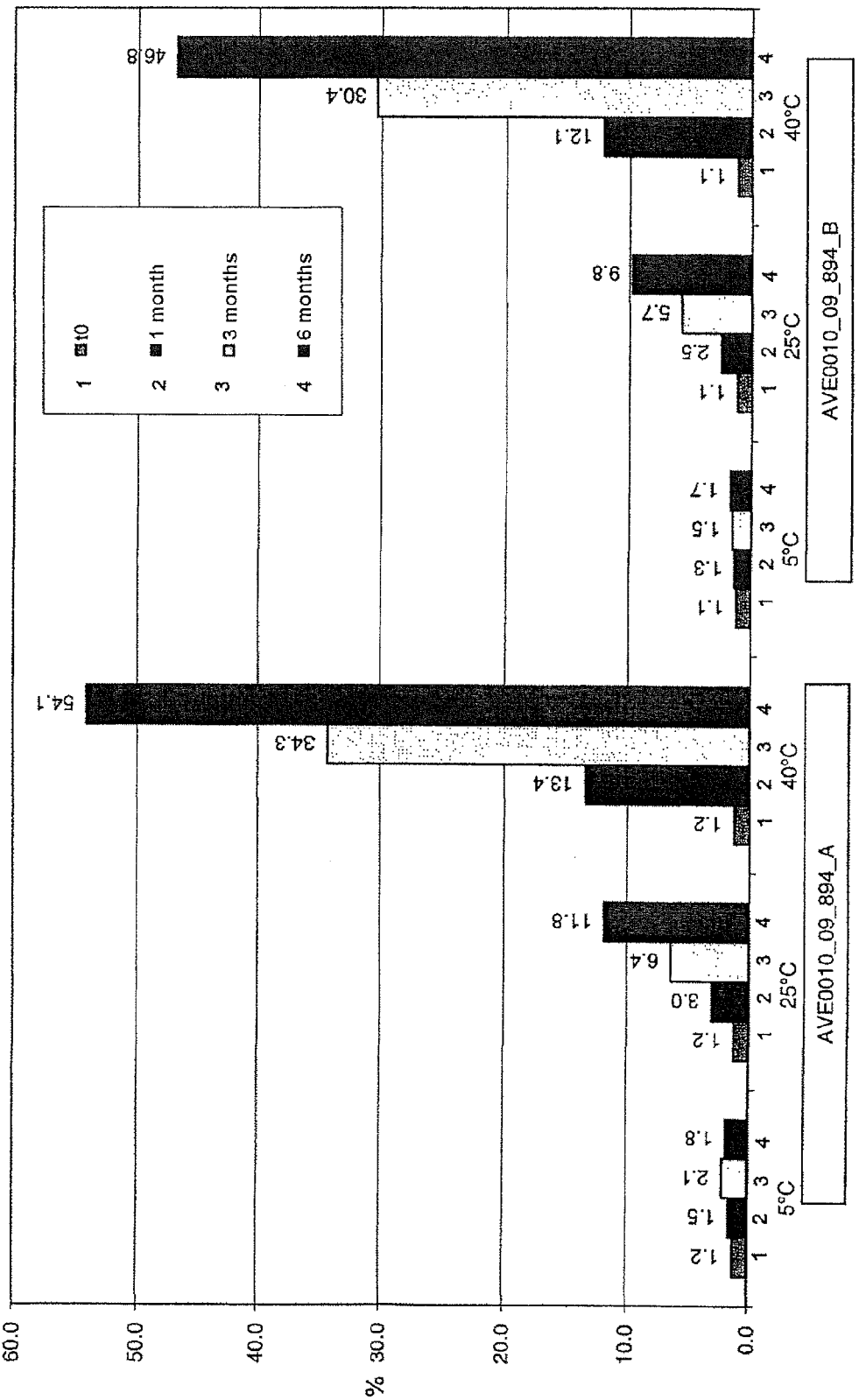
FIGS. 5 and 6 show the percentage content of all impurities (with respect to AVE0010) after storage at different temperatures. 1: start of storage t0. 2: storage for 1 month. 3: storage for 3 months. 3: storage for 6 months.
Figure 6:
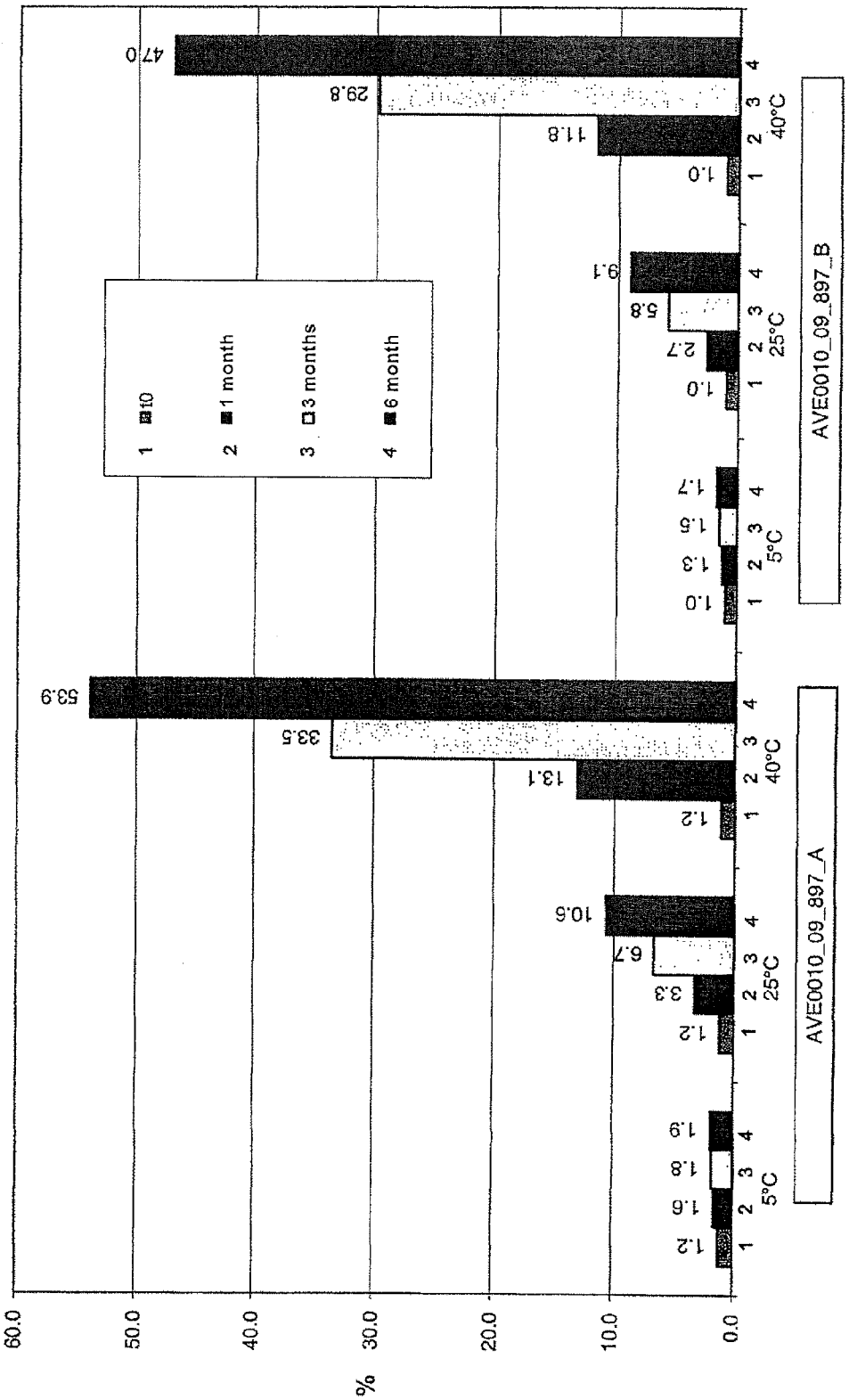

Total impurities. At 5° C., total impurities rose over the storage time of 6 months slightly from 1.2 to 1.8 or 1.9% (absence of methionine). When methionine was present, the rise was a little lower. At 25° C., a rise to 10.6% and 11.8%, respectively, was observed. In the presence of methionine, the values were below 10%. At 40° C., the proportion rose up to 54% (without methionine). When methionine was present, the proportion was approximately only 47% (see FIGS. 5 and 6).

The percentage values are the content values (percentage values of impurities) of the oxidation products, of total impurities, and of high-molecular-weight proteins (HMWP).

All values were determined by HPLC with the so-called 100% method. Here, in particular, it involves reversed-phase HPLC (C 18 column), in which a gradient method was used for the mobile phase:
a) 0.1% TFA, 15% ACN and b) 0.1% TFA, 75% ACN.
Detection at 215 nm (UV).

The high-molecular-weight proteins (HMWP) were detected by HPSEC, described in European Pharmacopeia 6.0 for injectable insulin preparations.

The data are summarized in the following tables:

| | Mean values: AVE0010_09_894_A + B | | | | | | | |
|---|---|---|---|---|---|---|---|---|
| | AVE0010_09_894_A | | | | AVE0010_09_894_B | | | |
| | $t_0$ | 1 Mon. | 3 Mon. | 6 Mon. | $t_0$ | 1 Mon. | 3 Mon. | 6 Mon. |
| 5° C. | | | | | | | | |
| Total impurities | 1.2 | 1.5 | 2.1 | 1.8 | 1.1 | 1.3 | 1.5 | 1.7 |
| AVE0010 Test | 101.5 | 99.6 | 98.0 | 97.8 | 101.1 | 100.5 | 99.4 | 98.6 |
| Proteins of high molecular weight | 0.3 | 0.3 | 0.4 | 0.3 | 0.2 | 0.2 | 0.2 | 0.3 |
| Oxidation products | 0.3 | 0.4 | 0.4 | 0.3 | 0.1 | 0.2 | 0.1 | 0.1 |
| 25° C. | | | | | | | | |
| Total impurities | 1.2 | 3.0 | 6.4 | 11.8 | 1.1 | 2.5 | 5.7 | 9.8 |
| AVE0010 Test | 101.5 | 97.9 | 94.0 | 88.6 | 101.1 | 98.7 | 94.8 | 90.9 |

-continued

| Mean values: AVE0010_09_894_A + B | | | | | | | | |
|---|---|---|---|---|---|---|---|---|
| | AVE0010_09_894_A | | | | AVE0010_09_894_B | | | |
| | $t_0$ | 1 Mon. | 3 Mon. | 6 Mon. | $t_0$ | 1 Mon. | 3 Mon. | 6 Mon. |
| Proteins of high molecular weight | 0.3 | 0.4 | 0.6 | 1.3 | 0.2 | 0.3 | 0.3 | 0.5 |
| Oxidation products | 0.3 | 0.4 | 0.5 | 0.8 | 0.1 | 0.2 | 0.2 | 0.2 |
| 40° C. | | | | | | | | |
| Total impurities | 1.2 | 13.4 | 34.3 | 54.1 | 1.1 | 12.1 | 30.4 | 46.8 |
| AVE0010 Test | 101.5 | 87.1 | 66.6 | 42.5 | 101.1 | 88.8 | 70.8 | 50.9 |
| Proteins of high molecular weight | 0.3 | 1.0 | 2.6 | 6.2 | 0.2 | 0.5 | 0.9 | 1.7 |
| Oxidation products | 0.3 | 0.6 | 0.9 | 1.3 | 0.1 | 0.2 | 0.2 | 0.2 |

| Mean values: AVE0010_09_897_A + B | | | | | | | | |
|---|---|---|---|---|---|---|---|---|
| | AVE0010_09_897_A | | | | AVE0010_09_897_B | | | |
| | $t_0$ | 1 Mon. | 3 Mon. | 6 Mon. | $t_0$ | 1 Mon. | 3 Mon. | 6 Mon. |
| 5° C. | | | | | | | | |
| Total impurities | 1.2 | 1.6 | 1.8 | 1.9 | 1.0 | 1.3 | 1.5 | 1.7 |
| AVE0010 Test | 99.2 | 98.2 | 97.5 | 96.7 | 99.5 | 99.2 | 98.0 | 97.1 |
| Proteins of high molecular weight | 0.1 | 0.1 | 0.1 | 0.2 | 0.1 | 0.1 | 0.1 | 0.1 |
| Oxidation products | 0.3 | 0.3 | 0.3 | 0.3 | 0.1 | 0.1 | 0.1 | 0.1 |
| 25° C. | | | | | | | | |
| Total impurities | 1.2 | 3.3 | 6.7 | 10.6 | 1.0 | 2.7 | 5.8 | 9.1 |
| AVE0010 Test | 99.2 | 96.6 | 92.8 | 87.4 | 99.5 | 97.8 | 93.6 | 90.0 |
| Proteins of high molecular weight | 0.1 | 0.2 | 0.5 | 0.9 | 0.1 | 0.1 | 0.2 | 0.4 |
| Oxidation products | 0.3 | 0.4 | 0.5 | 0.6 | 0.1 | 0.1 | 0.2 | 0.2 |
| 40° C. | | | | | | | | |
| Total impurities | 1.2 | 13.1 | 33.5 | 53.9 | 1.0 | 11.8 | 29.8 | 47.0 |
| AVE0010 Test | 99.2 | 86.8 | 66.5 | 42.6 | 99.5 | 88.0 | 70.7 | 51.0 |
| Proteins of high molecular weight | 0.1 | 0.8 | 2.2 | 5.4 | 0.1 | 0.4 | 0.9 | 1.6 |
| Oxidation products | 0.3 | 0.5 | 0.8 | 1.3 | 0.1 | 0.1 | 0.2 | 0.2 |

CONCLUSION

The proportion of oxidation products, of proteins of high molecular weight, and of total impurities are, individually or together, a measure of the chemical integrity of the compositions. From the results described above with the example compositions, it follows that the liquid compositions according to the present invention comprising

- a GLP-1 agonist or/and a pharmacologically tolerable salt thereof (more particularly AVE0010 or/and a pharmacologically tolerable salt thereof),
- optionally at least one pharmaceutically acceptable excipient,
- and methionine have improved stability or/and chemical integrity. The proportion of oxidized methionine, of total impurities, and of proteins of high molecular weight is lower in the compositions according to the present invention than in the comparative compositions. The composition according to the present invention (batches 894_B and 897_B) and the comparative compositions (batches 894_A and 897_A) differ in the presence/absence of methionine. Therefore, improved stability or/and chemical integrity can be ascribed to the methionine constituent in the compositions according to the present invention.

EXAMPLE 2

In a further experiment, it was studied how sodium EDTA and histidine have an effect in a composition according to the present invention.

| Composition B (as in example 1) | | |
|---|---|---|
| Substance | Specification according to pharmacopeia | Amount per unit |
| AVE0010 | Sanofi-Aventis | 0.10 mg |
| Sodium acetate trihydrate | Ph. Eur./USP | 3.50 mg |
| m-Cresol | Ph. Eur./USP | 2.70 mg |
| L-Methionine | Ph. Eur./USP | 3.00 mg |
| 85% Glycerol | Ph. Eur./USP | 18.00 mg |
| 0.1N Hydrochloric acid | Ph. Eur./USP | ad pH 4.5 |
| 0.1N NaOH solution | Ph. Eur./USP | ad pH 4.5 |
| Water for injection (WfI) | Ph. Eur./USP | ad 1.0 ml |

| Composition C | | |
|---|---|---|
| Substance | Specification according to pharmacopeia | Amount per unit |
| AVE0010 | Sanofi-Aventis | 0.10 mg |
| Sodium acetate trihydrate | Ph. Eur./USP | 3.50 mg |
| Sodium EDTA | Ph. Eur./USP | 1.00 mg |
| m-Cresol | Ph. Eur./USP | 2.70 mg |

-continued

Composition C

| Substance | Specification according to pharmacopeia | Amount per unit |
|---|---|---|
| L-Methionine | Ph. Eur./USP | 3.00 mg |
| L-Histidine | Ph. Eur./USP | 3.10 mg |
| 85% Glycerol | Ph. Eur./USP | 18.00 mg |
| 0.1N Hydrochloric acid | Ph. Eur./USP | ad pH 4.5 |
| 0.1N NaOH solution | Ph. Eur./USP | ad pH 4.5 |
| Water for injection (WfI) | Ph. Eur./USP | ad 1.0 ml |

In a standard experimental design, rabbits were treated with composition B or C or a saline solution subcutaneously (s.c.) or intramuscularly (i.m.). In each case, half the rabbits were sacrificed after 24 hours or 120 hours in order to determine the acute or subacute effects of the administration histologically. Also, it was determined whether repair/regeneration of any changes occurred.

Following subcutaneous injection of composition C, the animals showed after 24 hours, in contrast to the saline control, a light to moderate inflammatory reaction in the subcutaneous connective tissue. After subcutaneous injection 120 hours earlier, a clear trend was observable for the observed changes to repair by a fibroblastic reaction. Thus, compatibility could still be rated as moderate (instead of as incompatible).

With composition B, the animals showed after subcutaneous injection no or minimal differences to the saline control (good compatibility).

After intramuscular injection of composition C, the animals exhibited muscular necrosis (multifocal or disseminated), clearly differing from the saline controls, in which only the site of injection was visible as a clearly circumscribed necrotic area. With composition C, mineralization of the necrotic muscular tissue was observed after 120 hours, visible even in a necropsy of the animals. Although small or focal mineralization at various sites in rabbits is not unusual, the mineralization after injection of composition C was clearly associated with the necrotic areas. Thus, the reversibility of the lesions caused by the injection is more than questionable. Based on these findings, composition C after intramuscular injection in rabbits was rated as incompatible.

Composition B after intramuscular injection showed good compatibility (no or minimal differences to the saline control).

From these data, it follows that composition B, compared to composition C, had an improved compatibility in intramuscular or subcutaneous administration. Subcutaneous injection is the preferred route of administration for the compositions comprising a GLP-1 agonist, more particularly AVE0010, described in this application.

Thus, the compositions according to the present invention, which comprise a GLP-1 agonist, more particularly AVE0010, can be free of EDTA or/and histidine. Likewise, the compositions according to the present invention can be substantially free of EDTA and histidine.

The invention claimed is:

1. An aqueous liquid pharmaceutical composition comprising:
    (a) 0.01 mg/mL to 1.5 mg/mL desPro$^{36}$exendin-4(1-39)-Lys$_6$-NH$_2$ ("AVE0010") and/or a pharmacologically tolerable salt thereof;
    (b) methionine; and
    (c) water,
wherein the composition is substantially free of histidine.

2. The aqueous liquid composition of claim 1, wherein the composition further comprises a pharmaceutically acceptable preservative.

3. The aqueous liquid composition of claim 2, wherein the pharmaceutically acceptable preservative is m-cresol.

4. The aqueous liquid composition of claim 1, wherein the composition further comprises glycerol.

5. The aqueous liquid composition of claim 1, wherein the pH of the composition ranges from 3.5 to 5.

6. The aqueous liquid composition of claim 1, wherein the concentration of methionine ranges from 0.5 mg/mL to 20 mg/mL.

7. The aqueous liquid composition of claim 6, wherein the concentration of methionine ranges from 1 mg/mL to 5 mg/mL.

8. The aqueous liquid composition of claim 1, wherein the composition exhibits chemical integrity after storage for 6 months at a temperature of +25° C.

9. The aqueous liquid composition of claim 8, wherein at least 80% of the liquid composition's active substance is in a substantially chemically unchanged form after storage for 6 months at a temperature of +25° C.

10. The aqueous liquid composition of claim 8, wherein the percentage of oxidized methionine with respect to the entire methionine content of the GLP-1 agonist after storage for 6 months at a temperature of +25° C. is below 0.7%.

11. The aqueous liquid composition of claim 8, wherein the proportion of total impurities with respect to the entire mass of the GLP-1 agonist present in the composition after storage for 6 months at +25° C. is below 10%.

12. The aqueous liquid composition of claim 8, wherein the proportion of proteins of high molecular weight with respect to the entire mass of the GLP-1 agonist in the composition after storage for 6 months at +25° C. is below 0.8%.

13. The aqueous liquid composition of claim 1, comprising:
    (a) 0.01 mg/mL to 1.5 mg/mL AVE0010 and/or a pharmacologically tolerable salt thereof;
    (b) sodium acetate;
    (c) m-cresol;
    (d) L-methionine;
    (e) glycerol; and
    water,
wherein the composition is substantially free of histidine.

14. The aqueous liquid composition of claim 13, wherein the composition is substantially free of ethylenediaminetetraacetic acid (EDTA).

15. The aqueous liquid composition of claim 13, wherein the concentration of AVE0010 is about 0.01 mg/mL to about 0.5 mg/mL.

16. The aqueous liquid composition of claim 13, wherein the composition has a pH of about 4.5.

17. The aqueous liquid composition of claim 1, wherein the composition is an injectable composition.

18. The aqueous liquid composition of claim 1, wherein the composition further comprises at least one pharmaceutically acceptable excipient.

19. The aqueous liquid composition of claim 1, wherein the composition is suitable for parenteral administration.

20. The aqueous liquid composition of claim 1, wherein the composition is substantially free of ethylenediaminetetraacetic acid (EDTA).

21. The aqueous liquid composition of claim 1, wherein the composition comprises at least 50% w/w of water.

22. The aqueous liquid composition of claim 1, further comprising a buffer.

23. The aqueous liquid composition of claim 22, wherein the buffer is acetate, phosphate, or citrate.

24. The aqueous liquid composition of claim 22, wherein the buffer is acetate.

25. The aqueous liquid composition of claim 1, wherein the concentration of AVE0010 is about 50 µg/mL to about 100 µg/mL.

26. The aqueous liquid composition of claim 1, wherein the concentration of AVE0010 is about 33 µg/mL to about 50 µg/mL.

27. The aqueous liquid composition of claim 1, wherein the concentration of AVE0010 is about 0.01 mg/mL to about 0.5 mg/mL.

28. The aqueous liquid composition of claim 1, wherein the concentration of AVE0010 is about 33 µg/mL.

29. The aqueous liquid composition of claim 1, wherein the concentration of AVE0010 is about 50 µg/mL.

30. The aqueous liquid composition of claim 1, wherein the concentration of AVE0010 is about 100 µg/mL.

* * * * *